United States Patent
Braughler et al.

(10) Patent No.: US 9,675,642 B2
(45) Date of Patent: Jun. 13, 2017

(54) ENGINEERED DENDRITIC CELLS AND USES FOR THE TREATMENT OF CANCER

(71) Applicants: Intrexon Corporation, Blacksburg, VA (US); University Of Pittsburgh—Of The Commonwealth System Of Higher Education, Pittsburgh, PA (US)

(72) Inventors: J. Mark Braughler, Pittsburgh, PA (US); Prasanna Kumar, Collegeville, PA (US); Walter J Storkus, Glenshaw, PA (US); Hideho Okada, Pittsburgh, PA (US)

(73) Assignees: University Of Pittsburgh—Of The Commonwealth System Of Higher Education, Pittsburgh; Intrexon Corporation, Blacksburg ( * ) Notice: Subject to any disclaimer, the term of this patent is extended or adjusted under 35 U.S.C. 154(b) by 16 days.

(21) Appl. No.: 13/737,316

(22) Filed: Jan. 9, 2013

(65) Prior Publication Data

US 2013/0149290 A1    Jun. 13, 2013

Related U.S. Application Data

(62) Division of application No. 12/247,738, filed on Oct. 8, 2008.

(60) Provisional application No. 61/019,089, filed on Jan. 4, 2008, provisional application No. 60/991,807, filed on Dec. 3, 2007, provisional application No. 60/990,689, filed on Nov. 28, 2007, provisional application No. 60/990,167, filed on Nov. 26, 2007, provisional application No. 60/979,485, filed on Oct. 12, 2007, provisional application No. 60/979,480, filed on Oct. 12, 2007, provisional application No. 60/978,509, filed on Oct. 9, 2007, provisional application No. 60/978,394, filed on Oct. 8, 2007, provisional application No. 60/978,224, filed on Oct. 8, 2007.

(51) Int. Cl.
| | |
|---|---|
| A61K 48/00 | (2006.01) |
| C07H 21/04 | (2006.01) |
| A61K 35/15 | (2015.01) |
| A61K 31/00 | (2006.01) |
| A61K 31/166 | (2006.01) |
| A61K 31/4245 | (2006.01) |
| A61K 45/06 | (2006.01) |
| C07K 14/54 | (2006.01) |
| C12N 5/0784 | (2010.01) |
| G01N 33/68 | (2006.01) |
| A01K 67/00 | (2006.01) |
| A61K 38/00 | (2006.01) |

(52) U.S. Cl.
CPC .......... *A61K 35/15* (2013.01); *A61K 31/00* (2013.01); *A61K 31/166* (2013.01); *A61K 31/4245* (2013.01); *A61K 45/06* (2013.01); *C07K 14/5434* (2013.01); *C12N 5/0639* (2013.01); *G01N 33/6866* (2013.01); *A61K 38/00* (2013.01); *C07K 2319/715* (2013.01); *C12N 2501/23* (2013.01); *C12N 2501/24* (2013.01); *C12N 2510/00* (2013.01); *C12N 2710/10343* (2013.01); *C12N 2830/002* (2013.01); *C12N 2840/203* (2013.01); *G01N 2333/57* (2013.01); *G01N 2800/52* (2013.01)

(58) Field of Classification Search
CPC .......... A61K 5/15; C07K 14/5434; C07K 2319/715; C12N 5/0639; C12N 2840/203; C12N 2501/2312; C12N 2830/002
USPC .......................... 424/93.21; 536/23.5, 24.1
See application file for complete search history.

(56) References Cited

U.S. PATENT DOCUMENTS

| | | | | |
|---|---|---|---|---|
| 5,573,764 | A * | 11/1996 | Sykes ............... | C07K 14/5434 424/85.2 |
| 6,482,405 | B1 * | 11/2002 | Tahara et al. ............. | 424/93.21 |
| 7,091,038 | B2 * | 8/2006 | Palli .................. | C12N 15/1055 435/320.1 |
| 7,833,754 | B2 * | 11/2010 | Felber ............... | C07K 14/5434 435/320.1 |
| 2002/0182698 | A1 * | 12/2002 | O'Malley et al. ............ | 435/199 |

OTHER PUBLICATIONS

Karzenowski et al. Inducible control of transgene expression with ecdysone receptor: gene switches with high sensitivity, robust expression, and reduced size. BioTechniques 39:191-200, 2005.*
Tatsumi et al. Intratumoral delivery of dendritic cells engineered to secrete both interleukin (IL)-12 and IL-18 effectively treates local and distant disease in assoicateion with broadly reactive Tc1-type immunity. Cancer Res. 63:6378-6386, 2003.*
Tsugawa et al. Sequential delivery of interferon-alpha gene and DCs to intracranial gliomas promotes an effective antitumor response. Gene Therapy 11:1551-1558, 2004.*

* cited by examiner

*Primary Examiner* — Quang Nguyen
(74) *Attorney, Agent, or Firm* — Sterne, Kessler, Goldstein and Fox, P.L.L.C.

(57) ABSTRACT

This invention provides the field of therapeutics. Most specifically present invention provides methods of generating in vitro engineered dendritic cells conditionally expressing interleukin-12 (IL-12) under the control of a gene expression modulation system in the presence of activating ligand and uses for therapeutic purposes in animals including human.

7 Claims, 21 Drawing Sheets

ON/OFF Response of mIL-12 Expression to the Presence/Absence of RG-115932 in HT1080 Cells Transduced with Ad-RTS-mIL-12

CD8+ T cell Response Correlates with Antitumor Response

ENGINEERED DENDRITIC CELLS AND USES FOR THE TREATMENT OF CANCER

CROSS-REFERENCE TO RELATED APPLICATIONS

The present application claims the benefit of the filing date of U.S. Provisional Application No. 61/019,089, filed Jan. 4, 2008; U.S. Provisional Application No. 60/991,807, filed Dec. 3, 2007; U.S. Provisional Application No. 60/990,689, filed Nov. 28, 2007; U.S. Provisional Application No. 60/990,167, filed Nov. 26, 2007, U.S. Provisional Application No. 60/979,485, filed Oct. 12, 2007; U.S. Provisional Application No. 60/979,480, filed Oct. 12, 2007; U.S. Provisional Application No. 60/978,509, filed Oct. 9, 2007; U.S. Provisional Application No. 60/978,394, filed Oct. 8, 2007; and U.S. Provisional Application No. 60/978,224, filed Oct. 8, 2007, all of which are incorporated herein by reference in their entireties.

REFERENCE TO SEQUENCE LISTING SUBMITTED ELECTRONICALLY VIA EFS-WEB

The content of the electronically submitted sequence listing (Name: Seq_List.ascii.txt; Size: 62,000 bytes; and Date of Creation: Oct. 8, 2008) filed herewith the application is incorporated herein by reference in its entirety.

BACKGROUND OF THE INVENTION

Field of the Invention

This invention relates to the field of gene therapy for the treatment of cancer. In one embodiment, the invention relates to the engineering of dendritic cells to conditionally express interleukin-12 (IL-12) and use of the cells for therapeutics. In another embodiment, the invention relates to the engineering of dendritic cells to conditionally express interleukin-12 (IL-12) and/or interferon-alpha (IFN-alpha) and use of the cells for therapeutics.

Background

Various patents, patent applications, and publications are cited herein, the disclosures of which are incorporated by reference in their entireties. However, the citation of any reference herein should not be construed as an admission that such reference is available as "Prior Art" to the present application.

Interleukin-12 (IL-12) is a member of the type I cytokine family involved in contributing to a number of biological processes including, but not limited to, protective immune response and suppression of tumorigenesis (Abdi et al., 2006; Adorini, 1999; Adorini, 2001; Adorini et al., 2002; Adorini et al., 1996; Akhtar et al., 2004; Akiyama et al., 2000; Al-Mohanna et al., 2002; Aliberti et al., 1996; Allavena et al., 1994; Alli and Khar, 2004; Aizona et al., 1996; Amemiya et al., 2006; Araujo et al., 2001; Arulanandam et al., 1999; Athie et al., 2000; Athie-Morales et al., 2004; Bertagnolli et al., 1992; Bhardwaj et al., 1996; Biedermann et al., 2006; Brunda and Gately, 1994; Buchanan et al., 1995; Romani et al., 1997; Rothe et al., 1996; Satoskar et al., 2000; Schopf et al., 1999; Thomas et al., 2000; Tsung et al., 1997; Wolf et al., 1994; Yuminamochi et al., 2007). A growing body of evidence suggests that IL-12 may be a promising target to control human diseases (e.g., cancer).

Despite the fact that IL-12 remains promising as a cancer therapeutic agent based on its potent supportive activity on Type-1 anti-tumor NK cells, CD4$^+$ T cells and CD8$^+$ T cells (Trinchieri, 2003), the reported toxicity of recombinant human IL-12 (rhIL-12) in patients (Atkins et al., 1997), together with limited sources of GMP-grade rhIL-12 for clinical application, have prevented successful IL-12-based therapeutic approaches. Thus it seems reasonable that gene therapy approaches may represent safer, more tenable treatment options. Indeed, phase I clinical trials implementing intra- or peri-tumoral delivery of recombinant viral- (Sangro et al., 2004; Triozzi et al., 2005) or plasmid-based IL-12 cDNA (Heinzerling et al., 2005), or IL-12 gene modified autologous fibroblasts (Kang et al., 2001) have been found safe and well-tolerated.

However, objective clinical responses in patients with melanoma or a diverse range of carcinomas receiving these gene therapies have been rare, variable, transient and largely focused at the site of treatment (Heinzerling et al., 2005; Kang et al., 2001; Sangro et al., 2004; Triozzi et al., 2005). In cases where disease resolution was partial or complete, increased frequencies of tumor-infiltrating lymphocytes (Heinzerling et al., 2005; Sangro et al., 2004) and elevated levels of circulating tumor-specific CD8$^+$ T cells (Heinzerling et al., 2005) have been noted, consistent with the improved cross-priming of antigen-specific T cells in these patients.

In addition, there raised several residual concerns, e.g., unanticipated toxicities associated with DC-based IL-12 gene therapy and potential IL-12-dependent limitations in therapeutic DC.IL12 migration after intratumoral administration. Furthermore, there are further concerns regarding a timing of IL-12 production in transduced DC most important for therapeutic efficacy (Murphy et al, 2005)

Since the cross-priming of specific T cells is best accomplished by dendritic cells (DC) that serve as a natural but regulated source of IL-12 (Berard et al., 2000), recent reports of the superior pre-clinical efficacy of DC-based IL-12 gene therapy have been of great interest (Satoh et al., 2002; Tatsumi et al., 2003; Yamanaka et al., 2002). For example, it was shown that intratumoral (i.t.) injection of DC engineered to produce IL-12p70 (via recombinant adenovirus infection) results in the dramatically improved cross-priming of a broadly-reactive, tumor-specific CD8$^+$ T cell repertoire in concert with tumor rejection in murine models (Tatsumi et al., 2003). Given the previous use of a recombinant adenovirus encoding mIL-12 under a CMV-based promoter (rAd.cIL12, (Tatsumi et al., 2003)), engineered DC production of IL-12 was constitutive, hence the immunologic impact of this cytokine early within the tumor lesion and later within tumor-draining lymph nodes could not be resolved with regards to therapeutic outcome. Thus, a need exists for DC engineered for conditional expression of IL-12. The invention provides a promising therapeutic outcome for the use of such cells.

SUMMARY OF THE INVENTION

The invention provides a recombinant vector encoding a protein having the function of IL-12 under the control of a conditional promoter. In one embodiment, the vector is an adenovirus vector encoding IL-12p70 driven off a promoter that can be conditionally activated by provision of a soluble small molecule ligand such as a diacylhyrdazine, e.g., RG-115819, RG-115830 or RG-115932. This vector allows for the control of expression of IL-12 from DC (rAD.RheoIL12).

In one embodiment, the invention provides a vector for conditionally expressing a protein having the function of IL-12 comprising a polynucleotide encoding a gene switch, said gene switch comprising at least one transcription factor sequence, wherein said at least one transcription factor sequence encodes a ligand-dependent transcription factor, operably linked to a promoter, and (2) a polynucleotide encoding a protein having the function of IL-12 linked to a promoter which is activated by said ligand-dependent transcription factor. In another embodiment, the invention relates to a vector for conditionally expressing proteins having the function of IL-12 and/or IFN-alpha comprising a polynucleotide encoding a gene switch, said gene switch comprising at least one transcription factor sequence, wherein said at least one transcription factor sequence encodes a ligand-dependent transcription factor, operably linked to a promoter, and (2) a polynucleotide encoding a protein having the function of IL-12, and/or a polynucleotide encoding a protein having the function of IFN-alpha linked to a promoter which is activated by said ligand-dependent transcription factor.

For example, the invention provides a vector for conditionally expressing a protein having the function of IL-12 comprising a polynucleotide encoding a gene switch, wherein the polynucleotide comprises (1) at least one transcription factor sequence operably linked to a promoter, wherein said at least one transcription factor sequence encodes a ligand-dependent transcription factor, and (2) a polynucleotide encoding a protein having the function of IL-12 linked to a promoter which is activated by said ligand-dependent transcription factor. The invention also provides a vector for conditionally expressing proteins having the function of IL-12 and/or IFN-alpha comprising a polynucleotide encoding a gene switch, wherein the polynucleotide comprises (1) at least one transcription factor sequence operably linked to a promoter, wherein said at least one transcription factor sequence encodes a ligand-dependent transcription factor, and (2) a polynucleotide encoding a protein having the function of IL-12, and/or a polynucleotide encoding a protein having the function of IFN-alpha linked to a promoter which is activated by said ligand-dependent transcription factor.

The invention further provides a method of producing a population of DC conditionally expressing a protein having the function of IL-12 by modifying the DC with a recombinant vector conditionally expressing a protein having the function of IL-12, e.g., rAd.RheoIL12. In another embodiment, the invention provides a method of producing a population of DC conditionally expressing proteins having the function of IL-12 and/or IFN-alpha by modifying the DC with a recombinant vector conditionally expressing proteins having the function of IL-12 and/or IFN-alpha.

In one embodiment, the invention provides a method of producing a population of dendritic cells conditionally expressing a protein having the function of IL-12, comprising modifying at least a portion of dendritic cells by introducing into said dendritic cells a vector comprising a polynucleotide encoding a gene switch, said gene switch comprising at least one transcription factor sequence, wherein said at least one transcription factor sequence encodes a ligand-dependent transcription factor, operably linked to a promoter, and (2) a polynucleotide encoding a protein having the function of IL-12 linked to a promoter which is activated by said ligand-dependent transcription factor. In another embodiment, the invention provides a method of producing a population of dendritic cells conditionally expressing proteins having the function of IL-12 and/or IFN-alpha, comprising modifying at least a portion of dendritic cells by introducing into said dendritic cells a vector comprising a polynucleotide encoding a gene switch, said gene switch comprising at least one transcription factor sequence, wherein said at least one transcription factor sequence encodes a ligand-dependent transcription factor, operably linked to a promoter, and (2) a polynucleotide encoding a protein having the function of IL-12, and/or a polynucleotide encoding a protein having the function of IFN-alpha linked to a promoter which is activated by said ligand-dependent transcription factor.

For example, the invention provides a method of producing a population of dendritic cells conditionally expressing a protein having the function of IL-12, comprising modifying at least a portion of dendritic cells by introducing into said dendritic cells a vector comprising a polynucleotide encoding a gene switch, wherein the polynucleotide comprises (1) at least one transcription factor sequence operably linked to a promoter, wherein said at least one transcription factor sequence encodes a ligand-dependent transcription factor, and (2) a polynucleotide encoding a protein having the function of IL-12 linked to a promoter which is activated by said ligand-dependent transcription factor. The invention provides a method of producing a population of dendritic cells conditionally expressing proteins having the function of IL-12 and/or IFN-alpha, comprising modifying at least a portion of dendritic cells by introducing into said dendritic cells a vector comprising a polynucleotide encoding a gene switch, wherein the polynucleotide comprises (1) at least one transcription factor sequence operably linked to a promoter, wherein said at least one transcription factor sequence encodes a ligand-dependent transcription factor, and (2) a polynucleotide encoding a protein having the function of IL-12, and/or a polynucleotide encoding a protein having the function of IFN-alpha linked to a promoter which is activated by said ligand-dependent transcription factor.

The invention also provides a population of DC modified to conditionally express a protein having the function of IL-12 with a recombinant vector conditionally expressing a protein having the function of IL-12, e.g., the rAd.RheoIL12 vector. It has been found that DC infected with rAd.RheoIL12 produced elevated levels of IL-12 only after provision of an activating ligand. Another embodiment provides a population of DC modified to conditionally express a protein having the function of IL-12 and/or a protein having the function of IFN-alpha with a recombinant vector conditionally expressing a protein having the function of IL-12 and/or the function of IFN-alpha. Useful ligands include, but are not limited to RG-115830, RG-115932, RG-115819, RSL1, and other diacylhydrazines.

In one embodiment, the invention provides an in vitro engineered dendritic cell comprising a vector comprising a polynucleotide encoding a gene switch, said gene switch comprising at least one transcription factor sequence, wherein said at least one transcription factor sequence encodes a ligand-dependent transcription factor, operably linked to a promoter, and (2) a polynucleotide encoding a protein having the function of IL-12 linked to a promoter which is activated by said ligand-dependent transcription factor. In another embodiment, the invention provides an in vitro engineered dendritic cell comprising a vector comprising a polynucleotide encoding a gene switch, said gene switch comprising at least one transcription factor sequence, wherein said at least one transcription factor sequence encodes a ligand-dependent transcription factor, operably linked to a promoter, and (2) a polynucleotide encoding a protein having the function of IL-12, and/or a polynucleotide encoding a protein having the function of IFN-alpha linked to a promoter which is activated by said ligand-dependent transcription factor.

For example, the invention provides an in vitro engineered dendritic cell comprising a vector comprising a polynucleotide encoding a gene switch, wherein the polynucleotide comprises (1) at least one transcription factor sequence operably linked to a promoter, wherein said at least one transcription factor sequence encodes a ligand-dependent transcription factor, and (2) a polynucleotide encoding a protein having the function of IL-12 linked to a promoter which is activated by said ligand-dependent transcription factor. The invention provides an in vitro engineered dendritic cell comprising a vector comprising a polynucleotide encoding a gene switch, wherein the polynucleotide comprises (1) at least one transcription factor sequence operably linked to a promoter, wherein said at least one transcription factor sequence encodes a ligand-dependent transcription factor, and (2) a polynucleotide encoding a protein having the function of IL-12, and/or a polynucleotide encoding a protein having the function of IFN-alpha linked to a promoter which is activated by said ligand-dependent transcription factor.

The current invention also provides a pharmaceutical composition comprising a population of DC modified to conditionally express a protein having the function of IL-12 with a recombinant vector conditionally expressing a protein having the function of IL-12, e.g., the rAd.RheoIL12 vector. In another embodiment, the invention provides a pharmaceutical composition comprising a population of DC modified to conditionally express a protein having the function of IL-12 and/or a protein having the function of IFN-alpha with a recombinant vector conditionally expressing a protein having the function of IL-12 and/or a protein having the function of IFN-alpha.

The invention also provides a treatment of cancer, such as melanoma tumors or glioma tumors. IL-12 gene therapy has demonstrated anti-tumor efficacy in animal model studies when applied as a recombinant cDNA vector (Faure et al., 1998; Sangro et al., 2005), but even more so, when applied in the context of gene-modified DC (Satoh et al., 2002; Svane et al., 1999; Tatsumi et al., 2003; Yamanaka et al., 2002). To date, however, human phase I trials of IL-12 gene therapy implementing plasmids or viral vectors have failed to achieve durable, objective clinical responses in the cancer setting (Heinzerling et al., 2005; Kang et al., 2001; Sangro et al., 2004; Triozzi et al., 2005). DC-based IL-12 gene therapy (with or without MN-alpha) described herein provides a promising therapeutic modality.

In one embodiment, the invention provides a method for treating a tumor in a mammal, comprising (a) administering intratumorally to tumor microenvironments a population of an in vitro engineered dendritic cells, wherein said dendritic cells comprise a vector comprising a polynucleotide encoding a gene switch, wherein the polynucleotide comprises (1) at least one transcription factor sequence operably linked to a promoter, wherein said at least one transcription factor sequence encodes a ligand-dependent transcription factor, and (2) a polynucleotide encoding a protein having the function of IL-12 linked to a promoter which is activated by said ligand-dependent transcription factor and (b) administering to said mammal an effective amount of a ligand, which activates the ligand-dependent transcription factor; thereby inducing expression of a protein having the function of IL-12 and treating said tumor.

For example, the invention provides a method for treating a tumor in a mammal, comprising the steps of:
(a) engineering dendritic cells in vitro to conditionally express a protein having the function of IL-12;
(b) administering intratumorally to tumor microenvironments said in vitro engineered dendritic cells; and
(c) administering to said mammal a therapeutically effective amount of an activating ligand;
thereby inducing expression of a protein having the function of IL-12 and treating said tumor.

In further embodiments, the invention provides a method for treating a tumor in a mammal, comprising (a) administering intratumorally to tumor microenvironments an in vitro engineered dendritic cells, wherein said dendritic cells comprise a vector comprising a polynucleotide encoding a gene switch, wherein the polynucleotide comprises (1) at least one transcription factor sequence operably linked to a promoter, wherein said at least one transcription factor sequence encodes a ligand-dependent transcription factor, and (2) a polynucleotide encoding a protein having the function of IL-12 and/or a protein having the function of IFN-alpha, linked to a promoter activated by said ligand-dependent transcription factor and (b) administering to said mammal a therapeutically effective amount of an activating ligand; thereby inducing expression of a protein having the function of IL-12 and/or a protein having the function of IFN-alpha and treating said tumor.

For example, the invention provides a method for treating a tumor in a mammal, comprising the steps of:
(a) engineering dendritic cells in vitro to conditionally express a protein having the function of IL-12 and/or a protein having the function of IFN-alpha;
(b) administering intratumorally to tumor microenvironments said in vitro engineered dendritic cells; and
(c) administering to said mammal a therapeutically effective amount of an activating ligand;
thereby inducing expression of a protein having the function of IL-12 and/or a protein having the function of IFN-alpha and treating said tumor.

The invention also provides a method for determining the efficacy of engineered DC-based therapy by measuring the level of expression or activity of IFN-γ in a patient before the start of therapy, thereby generating a control level, followed by the administration of DC engineered to conditionally express a protein having the function of IL-12 and an effective amount of an activating ligand and then measuring the level of expression of IFN-γ to generate a test level, and comparing the control level to the test level to determine if the therapeutic regime is effective.

In one embodiment, the invention provides a method for determining the efficacy of an in vitro engineered dendritic cell based therapeutic regime in a patient comprising:
(a) measuring the level of expression or the level of activity or both of interferon-gamma (IFN-γ) in a first biological sample obtained from said patient in need thereof before administration of in vitro engineered dendritic cells, thereby generating a control level;
(b) administering to a patient in need thereof, in vitro engineered dendritic cells engineered to conditionally express a protein having the function of IL-12;
(c) administering to said patient in need thereof an effective amount of an activating ligand;
(d) measuring the level of expression or the level of activity or both of IFN-γ in a second biological sample obtained from said patient in need thereof following administration of in vitro engineered DC and activating ligand, thereby generating a test level; and
(e) comparing the control level to the test level of IFN-γ, wherein an increase in the test level of expression, activity or both of IFN-γ relative to the control level indicates that the therapeutic regime is effective in said patient in need thereof.

In another embodiment, the invention provides a method of inducing conditional expression of a protein having the function of interleukin-12 (IL-12) in a dendritic cell comprising: (1) administering to a mammal in need thereof an effective amount of a population of the in vitro engineered dendritic cells of the invention; and (2) administering to said mammal in need thereof an effective amount of a ligand, which activates the ligand-dependent transcription factor.

In advance of clinical implementation, previous studies performed in a CMS4 sarcoma model in BALB/c mice were extended and it was observed that intratumoral delivery of syngenic bone marrow-derived DC pre-infected with Ad.cIL12 (constitutive expression), resulted in effective tumor rejection (Tatsumi et al., 2003). Rejection was associated with systemic CD8+ T cell-mediated immunity against CMS4 tumors, (Tatsumi et al., 2003).

DETAILED DESCRIPTION OF DRAWINGS

Figure 3A:
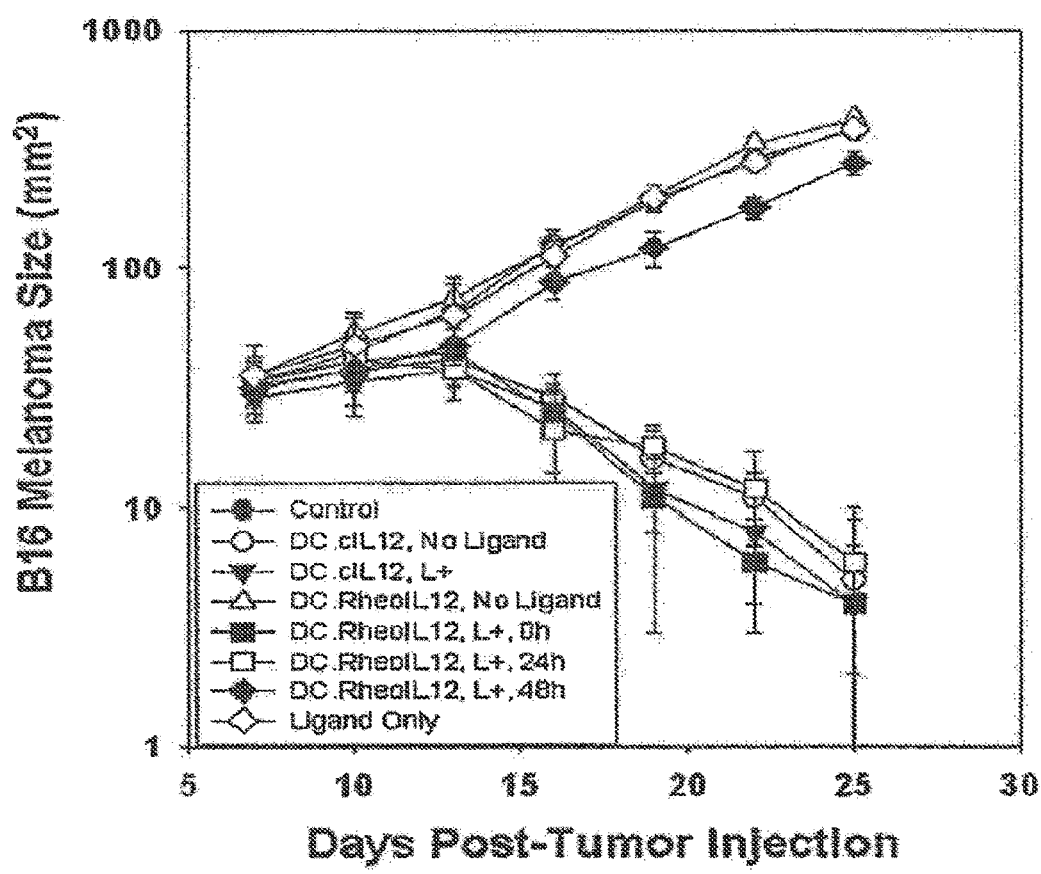
Figure 4:
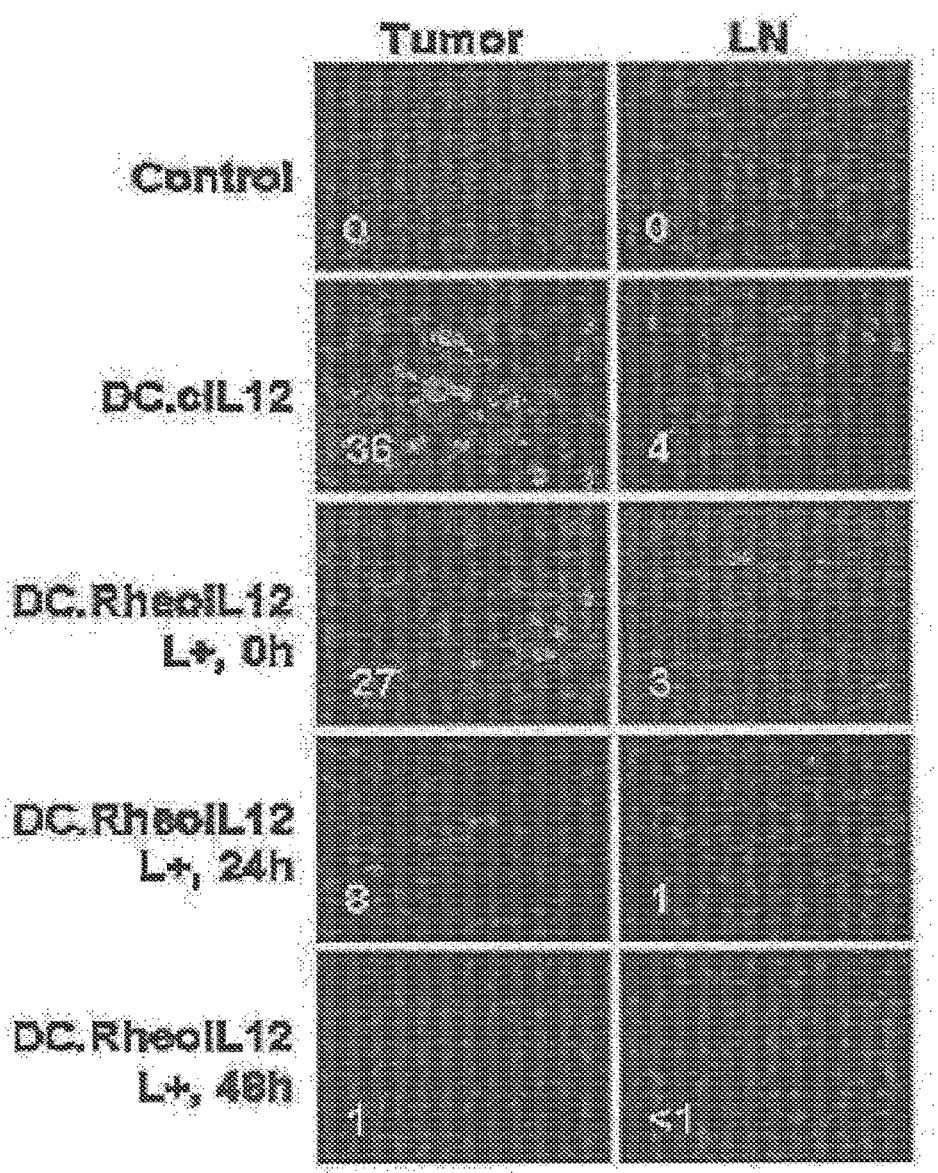

FIG. 3A: shows engineered DC administered into melanoma tumor microenvironments cause tumor regression when RG-115830 is intraperitoneally injected into C57Bl/6 mice bearing established 7 day B16 subcutaneous tumors within 24 hours of DC injection 3B-3C: tumor regression occurred when RG-115830 was administered from days 1 to 5, but not when administered only on days 1 to 2 or 1 to 3 post-DC injection FIG. 4 shows that engineered DC exhibit prolonged survival in tumor and tumor-draining lymph node after intraperitoneal injection of the activating ligand within 24 hours after DC injection, much less survival and no survival of DC by ligand at 48 hours and 72 hours respectively.

Figure 5A:
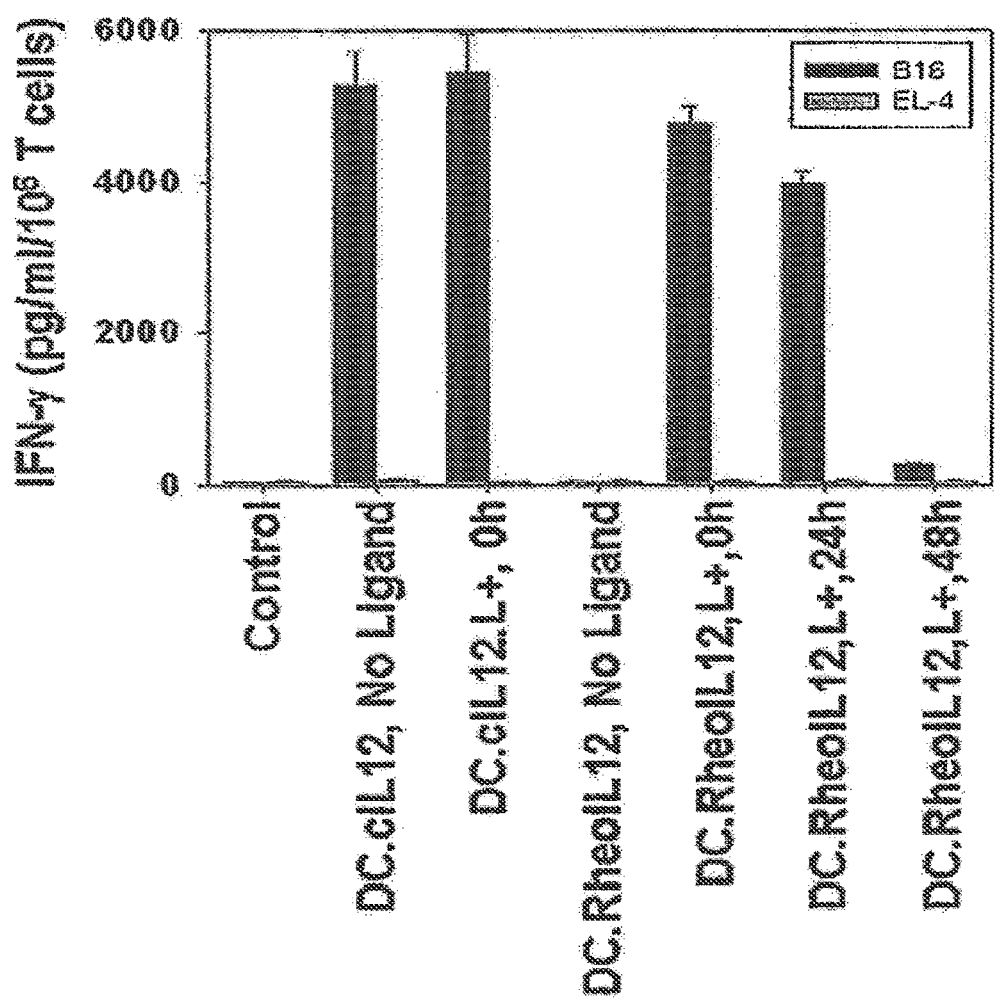
Figure 5B:
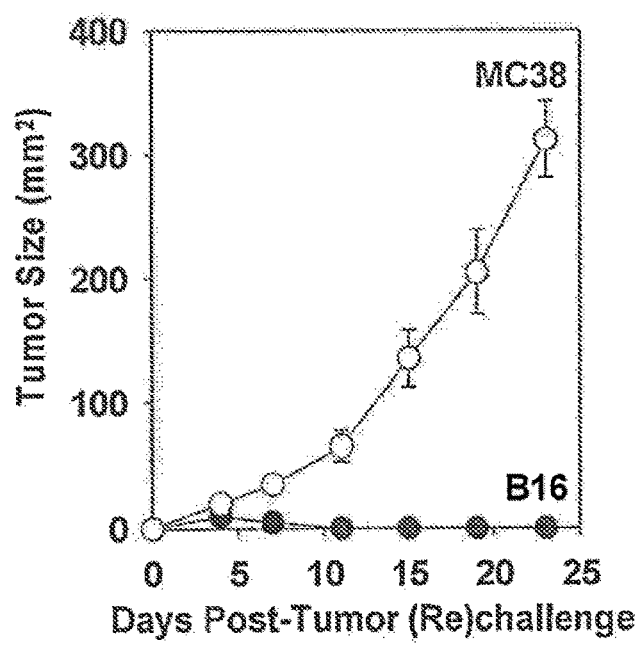

FIG. 5 A shows that engineered DC promote strong peripheral activation of anti-B16 CD8+ T cells if activating ligand is provided within 24 hours of engineered DC injection. FIG. 5B shows that all mice previously cured of their melanoma exhibited specific protection against B16 tumor cells but not against MC38 colon carcinoma cells when tumor-free animals were rechallenged with relevant B16 melanoma cells or MC38 colon carcinoma cells on day 45 (post-initial B16 challenge).

Figure 6:
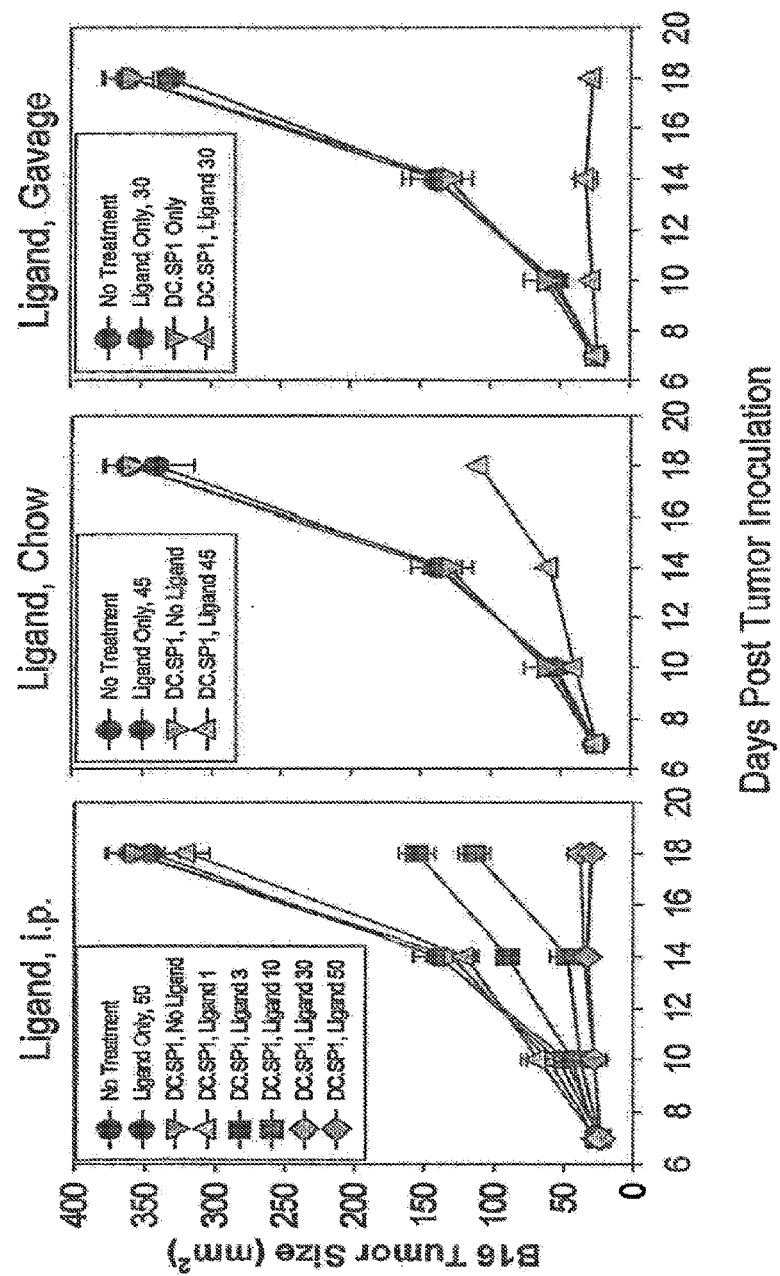

FIG. 6 shows the therapeutic benefit induced by administration of ligand by intraperitoneal or oral routes.

Figure 7:
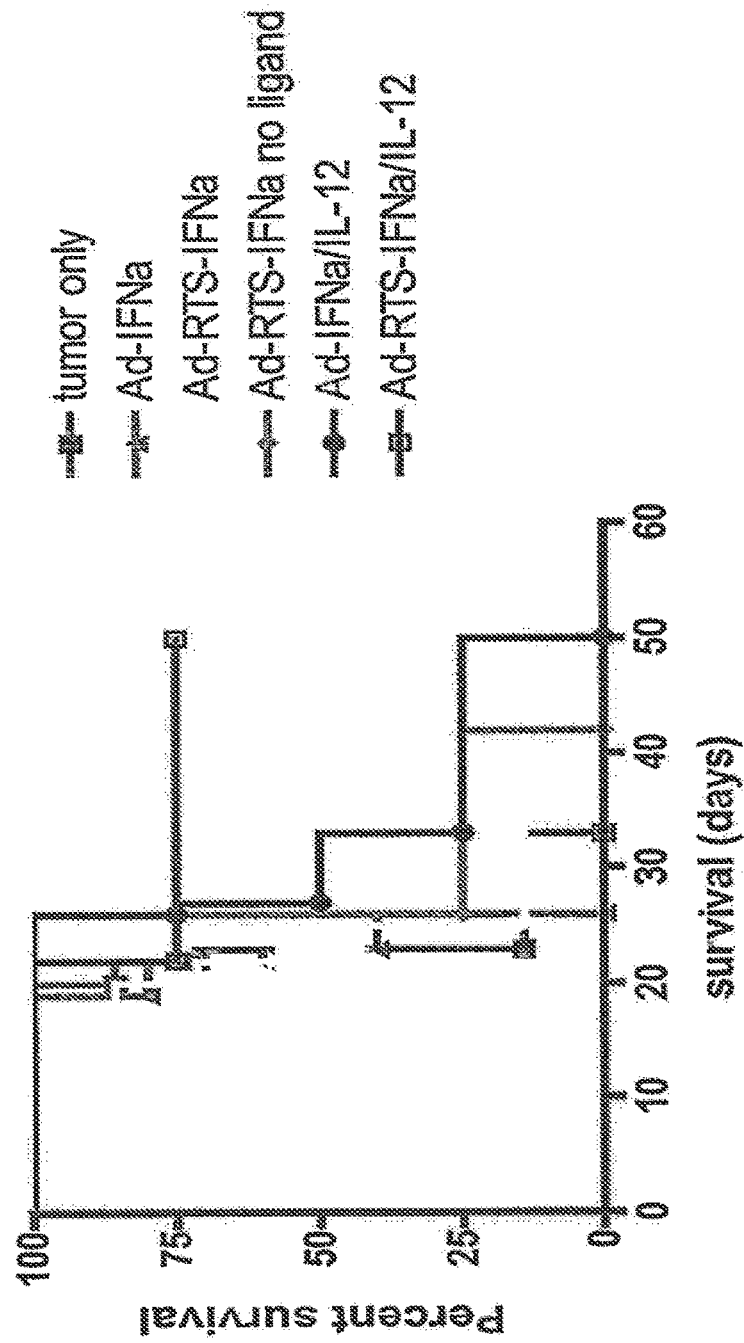

FIG. 7 shows the Kaplan-Meier plots of the survival of mice as a result of intratumoral injection of mouse glioma (GL261) with dendritic cells transduced with polynucleotides encoding IL-12 and/or IFN-alpha under the control of RTS. Abbreviations in this figure are as follows: Ad-IFNa is Adenoviral vector constitutively expressing IFN-alpha; Ad-RTS-IFNa is Adenoviral vector encoding IFN-alpha under RTS control; Ad-RTS-IFNa no ligand is Adenoviral vector containing RTS and IFN-alpha where no activator ligand was present; Ad-IFNa/IL-12 corresponds to DC transduced with Adenoviral vectors encoding IFN-alpha and IL-12; and Ad-RTS-IFNa/IL-12 corresponds to DC transduced with two Adenoviral vectors encoding IFN-alpha and IL-12 under RTS control.

Figure 8:
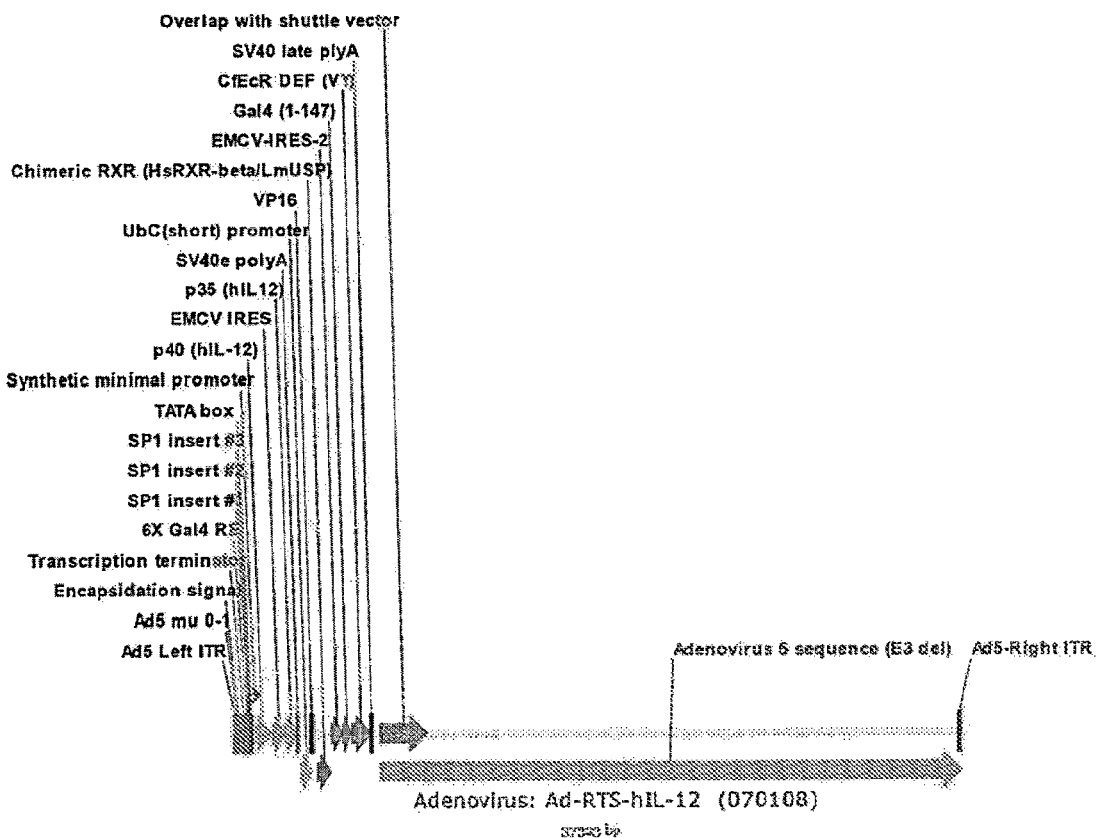

FIG. 8 shows a map for the adenoviral vector Ad-RTS-hIL-12.

Figure 9:
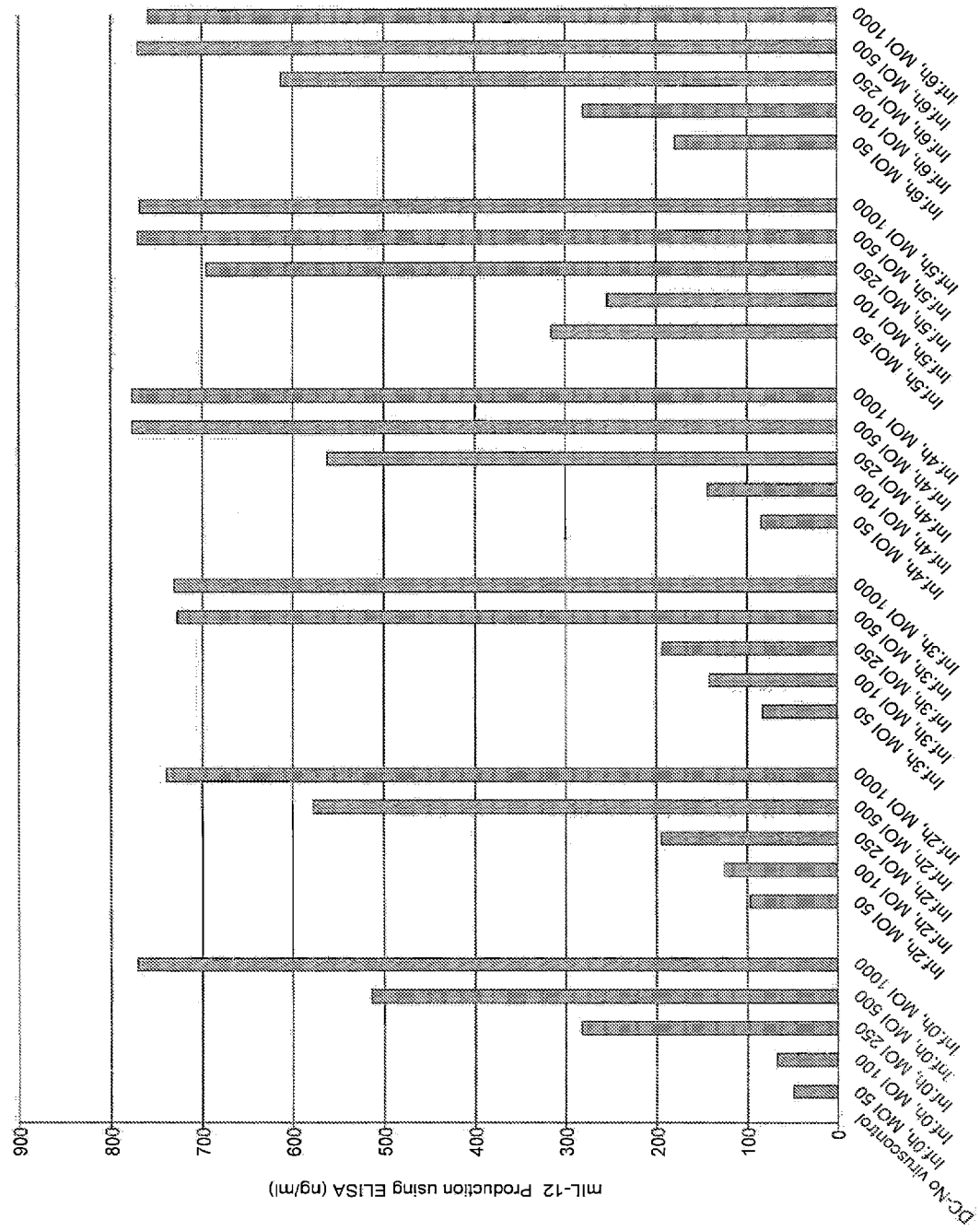

FIG. 9 shows IL-12 production by human dendritic cells transduced with adenoviral vector Ad-RTS-mIL-12 at different MOI and duration of viral adsorption. Adenoviral transduction of human DCs at different MOI and for different duration of viral adsorption showed efficient transduction of these cells by 3 hour viral adsorption at MOI of 500. The activator drug ("AD" or "activating ligand") induced IL-12 expression in these transduced human dendritic cells.

Figure 10:
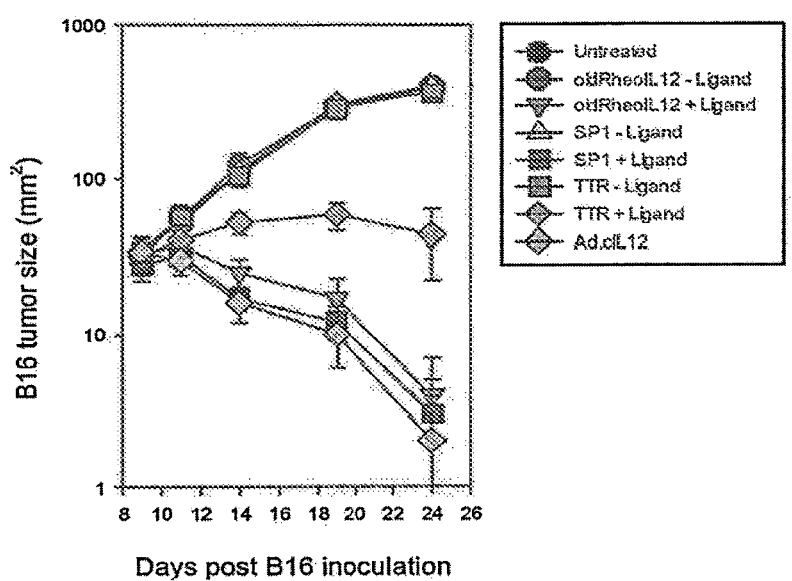

FIG. 10 shows a comparison of the effects of different IL-12-containing adenoviral vectors. The SP1-RheoIL-12 variant was the most effective of the Rheoswitch-containing variants. Sp1-RheoIL-12 differs from oldRheoIL-12 in that it replaced an AdEasy-1 vector backbone with the RAPAd vector backbone (ViraQuest). Similarly, TTR-RheoIL-12 differs from oldRheoIL-12 in that it contains a TTR minimal promoter downstream of the Gal4 binding sites, replacing the synthetic minimal promoter and the Sp1 binding sites, and the vector backbone is RAPAd (ViraQuest). As FIG. 10 illustrates, Sp1-RheoIL-12 was comparable to oldRheoIL-12 and more effective than TTR-RheoIL-12 in reducing B16 melanoma tumor size.

Figure 11:
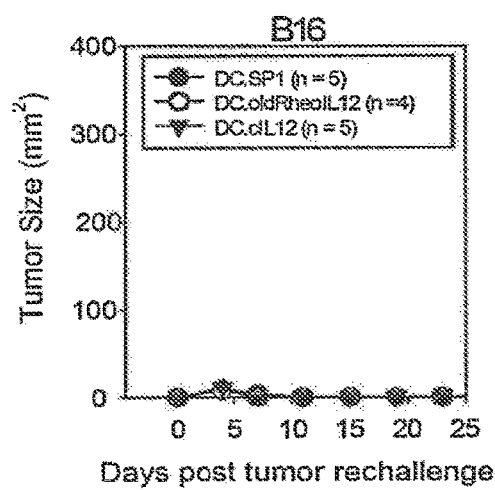

FIG. 11 shows lack of B16 melanoma tumor formation after rechallenge of mice previously treated with dendritic cells containing recombinant adenoviral Rheoswitch inducible IL-12. This shows that B16 melanoma tumors were prevented from growing for up to 25 days when B16 immune mice were re-inoculated 45 days after the first inoculation with B16 cells. Murine dendritic cells were generated from bone marrow of B6 mice by 7 day culture in complete media (RPMI-1640, 10% FBS) containing rmIL-4 plus rmGM-CSF. CD11c positive dendritic cells were then isolated using specific MACS beads per manufacturer's protocol (Miltenyi Biotech) and infected at MOI of 100 using rAd.IL-12 (RheoIL-12 vs. SP1 vs. TTR) for 24 hours prior to injection of 10E6 DC into established day 9 s.c. B16 melanoma tumors (5 mice per group, tumor on right flank). Mice were treated or not with daily i.p. injections of the activating ligand RG-115830 (30 mg/kg in 50 microliter DMSO) on days 6-4 post DC injection. Tumor size was monitored every 3-4 days and is reported in mm$^2$ as product of orthogonal diameters. To evaluate the specificity of therapy-associated protection, all tumor-free animals were rechallenged with 10E5 B16 melanoma cells on the left flank versus MC38 colon carcinoma cells on the right flank on day 45 post initial B16 tumor challenge. MC38 tumors formed but B16 tumors did not form.

Figure 12:
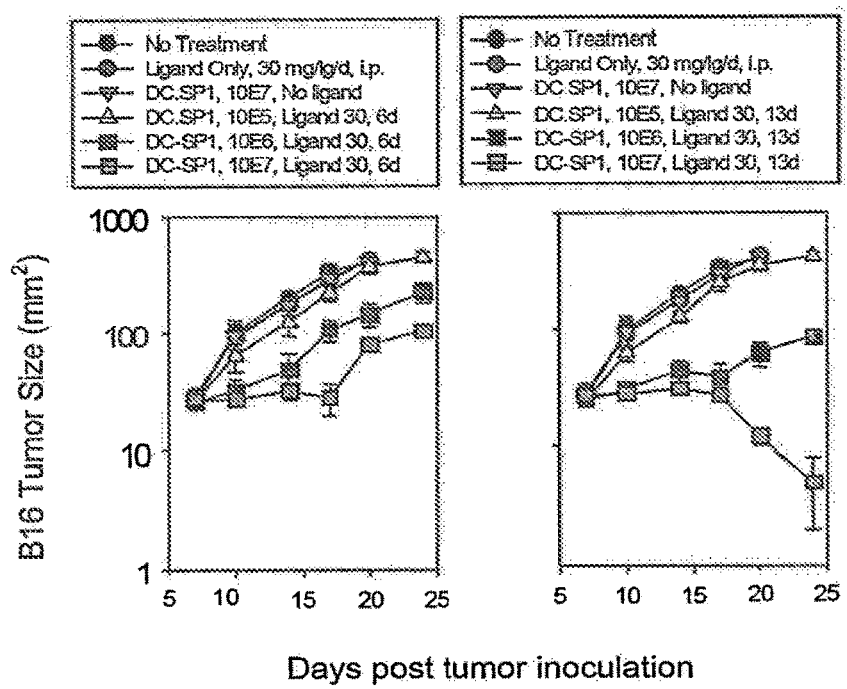

FIG. 12 shows a comparison among numbers of dendritic cells injected into the B16 tumor (10E5, 10E6, 10E7) and length of time of ligand administration (6 days or 13 days) and the resulting tumor regression in B16 melanoma tumor mouse model Ligand administered daily for 13 days in combination with 10E7 dendritic cells was most effective in causing tumor regression over a 25 day period.

Figure 13:
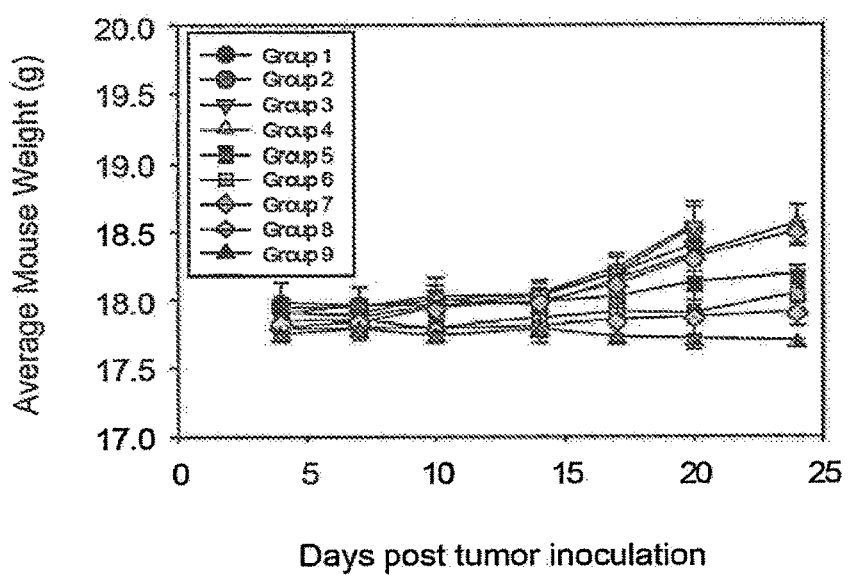

FIG. 13 shows that the therapy described herein was not associated with untoward loss in animal weight due to wasting. Wasting and weight loss is often associated with high levels of interferon-gamma and TNF-alpha which are known to be upregulated in response to IL-12.

Figure 14:
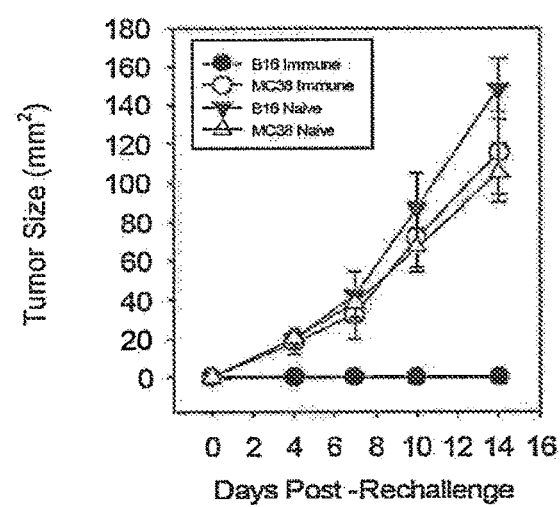

FIG. 14 shows lack of B16 melanoma tumor formation after rechallenge of mice previously treated with dendritic cells containing recombinant adenoviral Rheoswitch® inducible IL-12 and activator ligand RG-115932. B16 melanomas were established s.c. for 7 days in the right flanks of 5 syngeneic B6 mice. On day 7, DC.SP1-IL-12 (bone marrow derived DC infected at an MOI of 100 using the SP1 optimal switch) were injected intratumorally (i.t.) at doses of $10^5$, $10^6$ or $10^7$. RG-115932 was provided by i.p. injection beginning on the day of DC injection (and daily thereafter for either 6 days or 13 days). Each cohort contained 5 animals, with tumor growth monitored every 3-4 days and reported as mean size (mm squared based on the product of orthogonal measurements). Individual animal weights were also assessed at the time of tumor measurements (FIG. 13). All animals rendered free of disease by any therapy were rechallenged on day 50 (post-initial B16 tumor inoculation) with $10^5$ B16 melanoma cells on the opposite flank (left flank) of the original tumor and with $10^5$ MC38 colon carcinoma cells on the right flank. Tumor growth was monitored every 3-4 days and compared against growth observed in naïve (untreated) animals (see FIG. 12). FIG. 14 therefore shows that B16 melanoma tumors were prevented from growing for up to 24 days when B16 immune mice were re-inoculated with B16 cells. FIG. 14 also illustrates that B16 naïve mice were not protected from tumor formation, as were MC38 immune mice and MC38 naïve mice. MC38 is a colon carcinoma known in the art. This demonstrates the specificity of immunization caused by the original B16 tumor injection with dendritic cells containing recombinant adenoviral Rheoswitch® inducible IL-12.

Figure 15:
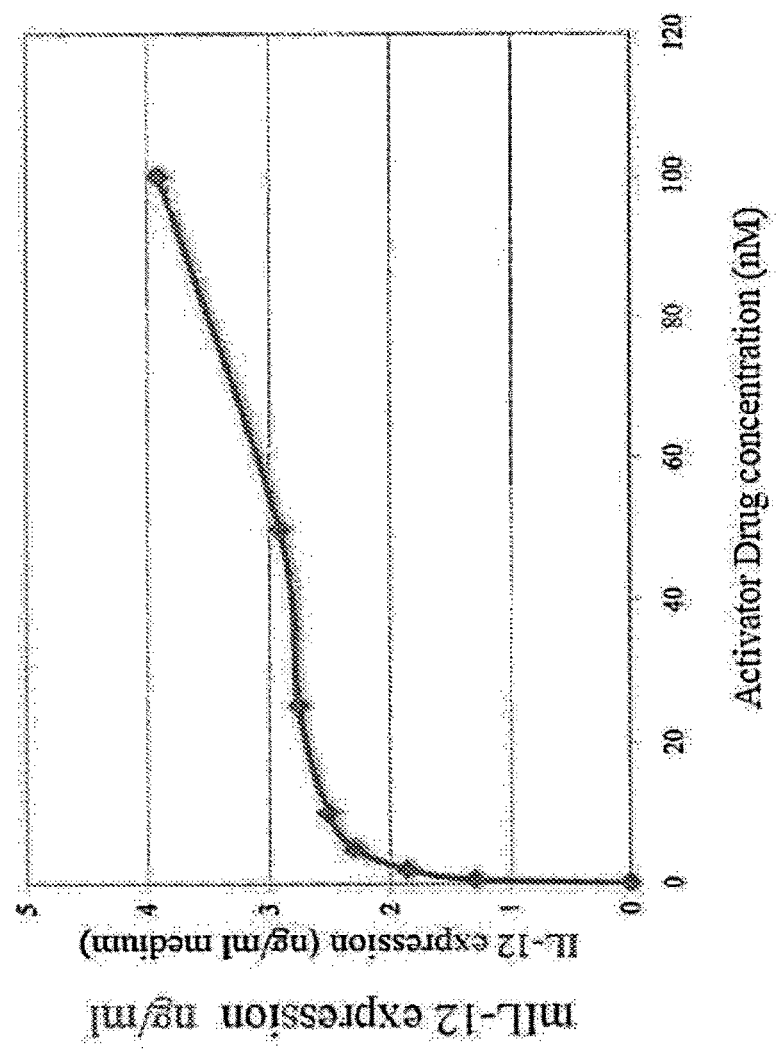

FIG. 15 shows Activator Drug (RG-115932) dose-dependent IL-12 expression in mouse dendritic cells transduced with Ad-RTS-mIL-12.

Figure 16:
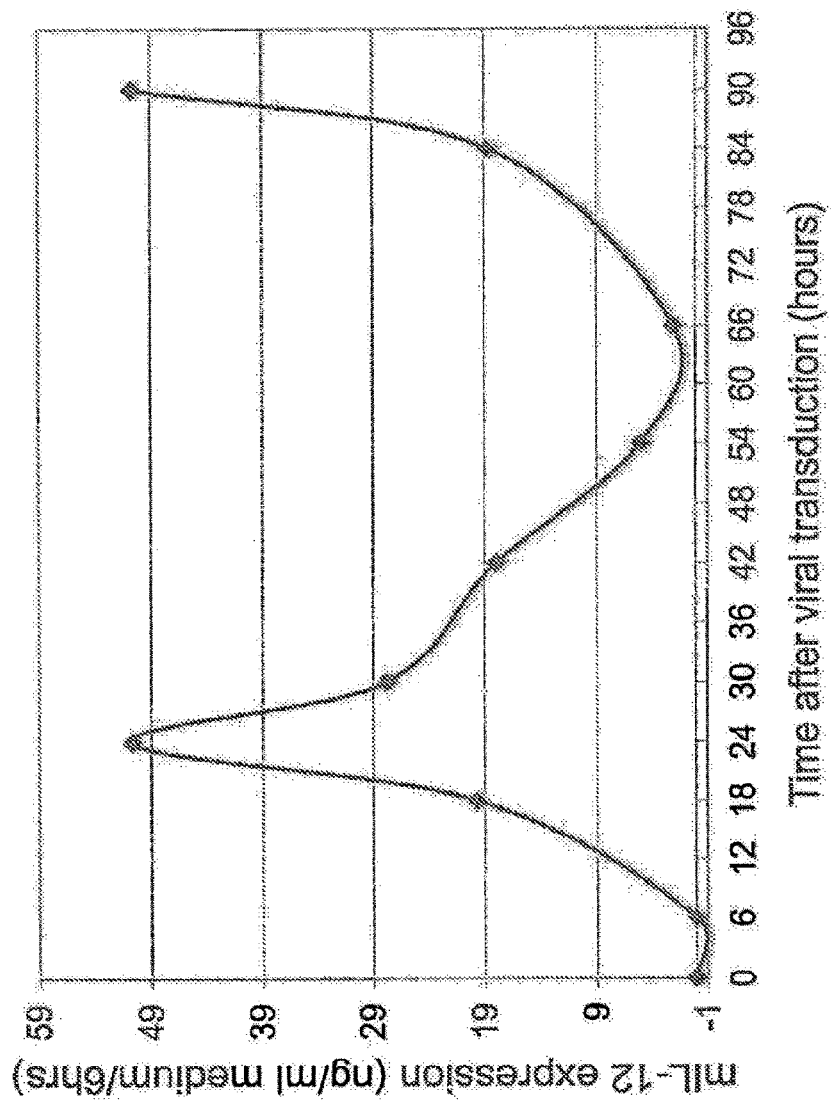

FIG. 16 shows On/Off response of mIL-12 expression to the presence or absence of RG-115932 in HT1080 cells transduced with Ad-RTS-mIL-12.

Figure 17:
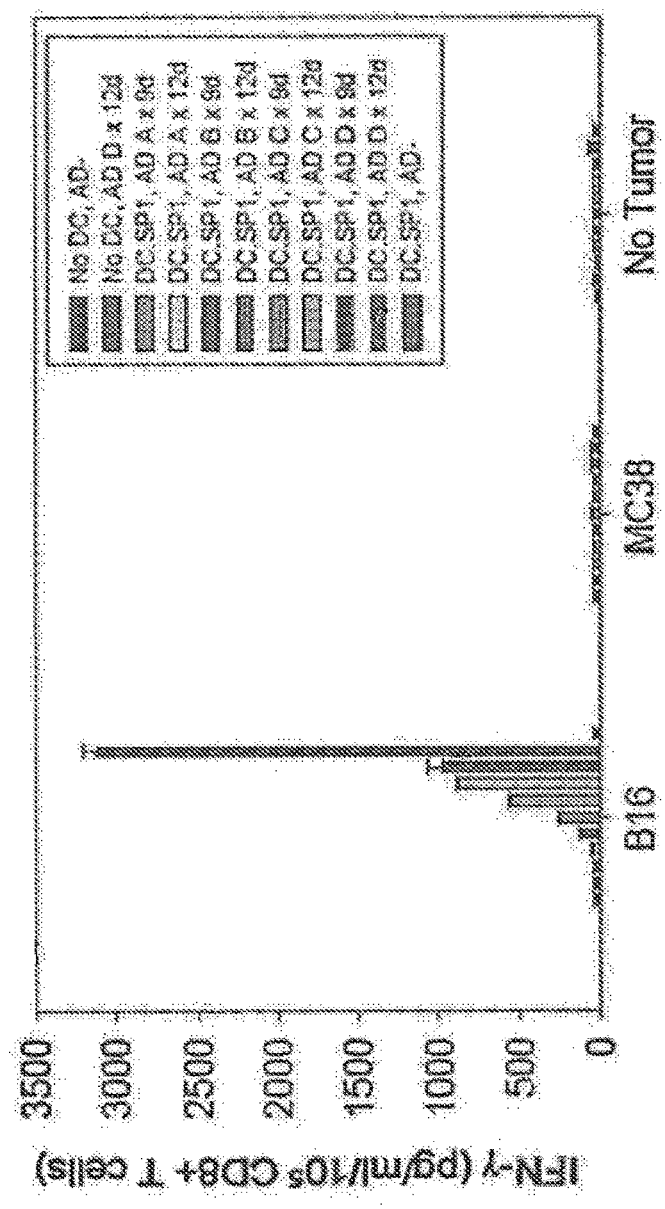

FIG. 17 shows that CD8+ T cell response to immunization by intratumoral injection of adenoviral transduced DC in the presence or absence of the Activating Drug (AD) corresponds with antitumor response.

Figure 18:
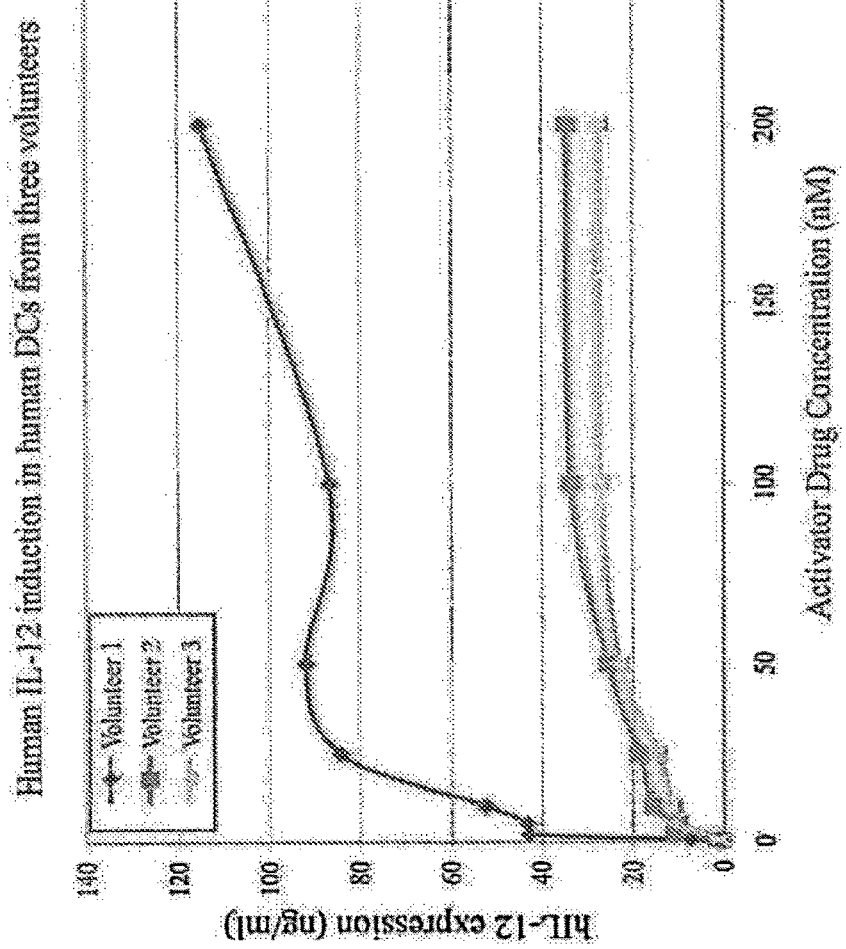

FIG. 18 shows human IL-12 induction in human DCs from three volunteers transduced with the adenoviral vector cencoding the human IL-12 under RTS control.

DETAILED DESCRIPTION OF SEQUENCES

SEQ ID NO: 1 is a full length nucleotide sequence of wild type mouse IL-12 p35 gene.
SEQ ID NO: 2 is a full length nucleotide sequence of wild type mouse IL-12 p40 gene.
SEQ ID NO: 3 is a full length nucleotide sequence of wild type human IL-12 p35 gene.
SEQ ID NO: 4 is a full length nucleotide sequence of wild type human IL-12 p40 gene.
SEQ ID NO: 5 is a full length polypeptide sequence of wild type mouse IL-12 p35 protein.
SEQ ID NO: 6 is a full length amino acid sequence of wild type mouse IL-12 p40 protein.
SEQ ID NO: 7 is a full length amino acid sequence of wild type human IL-12 p35 protein.
SEQ ID NO: 8 is a full length amino acid sequence of wild type human IL-12 p40 protein.
SEQ ID NO: 9 is a DNA sequence for an ecdysone response element found in *Drosophila*.
SEQ ID NO: 10 is a DNA sequence for an ecdysone response element found in *Drosophila melanogaster*.
SEQ ID NO: 11 is a DNA sequence for an ecdysone response element found in *Drosophila melanogaster*.
SEQ ID NO: 12 is 1-SceI restriction site in a homing endonuclease (HE) enzyme.
SEQ ID NO: 13 is a DNA sequence of adenovirus vector comprising human IL-12 coding sequence: Ad-RTS-hIL-12 (SP1-RheoIL-12).

The amino acid sequence of interferon alpha (IFN-alpha) is available from public databases as accession number AAA52724, the sequence of which is incorporated by reference herein. See also Capon et al., *Mol. Cell. Biol.* 5, 768-779 (1985).

DETAILED DESCRIPTION OF INVENTION

Unless otherwise defined, all terms of art, notations and other scientific terms or terminology used herein are intended to have the meanings commonly understood by those of skill in the art to which this invention pertains. In some cases, terms with commonly understood meanings are defined herein for clarity and/or for ready reference and understanding, and the inclusion of such definitions herein should not necessarily be construed to mean a substantial difference over what is generally understood in the art. Commonly understood definitions of molecular biology terms and/or methods and/or protocols can be found in Rieger et al., Glossary of Genetics: Classical and Molecular, 5th edition, Springer-Verlag: New York, 1991; Lewin, Genes V, Oxford University Press: New York, 1994; Sambrook et al., Molecular Cloning, A Laboratory Manual (3d ed. 2001) and Ausubel et al., Current Protocols in Molecular Biology (1994). As appropriate, procedures involving the use of commercially available kits and/or reagents are generally carried out in accordance with manufacturer's guidance and/or protocols and/or parameters unless otherwise noted.

The term "isolated" for the purposes of the invention designates a biological material (cell, nucleic acid or protein) that has been removed from its original environment (the environment in which it is naturally present). For example, a polynucleotide present in the natural state in a plant or an animal is not isolated, however the same polynucleotide separated from the adjacent nucleic acids in which it is naturally present, is considered "isolated."

The term "purified," as applied to biological materials does not require the material to be present in a form exhibiting absolute purity, exclusive of the presence of other compounds. It is rather a relative definition.

"Nucleic acid," "nucleic acid molecule," "oligonucleotide," and "polynucleotide" are used interchangeably and refer to the phosphate ester polymeric form of ribonucleosides (adenosine, guanosine, uridine or cytidine; "RNA molecules") or deoxyribonucleosides (deoxyadenosine, deoxyguanosine, deoxythymidine, or deoxycytidine; "DNA molecules"), or any phosphoester analogs thereof, such as phosphorothioates and thioesters, in either single stranded form, or a double-stranded helix. Double stranded DNA-DNA, DNA-RNA and RNA-RNA helices are possible. The term nucleic acid molecule, and in particular DNA or RNA molecule, refers only to the primary and secondary structure of the molecule, and does not limit it to any particular tertiary forms. Thus, this term includes double-stranded DNA found, inter alia, in linear or circular DNA molecules (e.g., restriction fragments), plasmids, supercoiled DNA and chromosomes. In discussing the structure of particular double-stranded DNA molecules, sequences may be described herein according to the normal convention of giving only the sequence in the 5' to 3' direction along the non-transcribed strand of DNA (i.e., the strand having a sequence homologous to the mRNA). A "recombinant DNA molecule" is a DNA molecule that has undergone a molecular biological manipulation. DNA includes, but is not limited to, cDNA, genomic DNA, plasmid DNA, synthetic DNA, and semi-synthetic DNA.

The term "fragment," as applied to polynucleotide sequences, refers to a nucleotide sequence of reduced length relative to the reference nucleic acid and comprising, over the common portion, a nucleotide sequence identical to the reference nucleic acid. Such a nucleic acid fragment according to the invention may be, where appropriate, included in a larger polynucleotide of which it is a constituent. Such fragments comprise, or alternatively consist of, oligonucleotides ranging in length from at least 6, 8, 9, 10, 12, 15, 18, 20, 21, 22, 23, 24, 25, 30, 39, 40, 42, 45, 48, 50, 51, 54, 57, 60, 63, 66, 70, 75, 78, 80, 90, 100, 105, 120, 135, 150, 200, 300, 500, 720, 900, 1000, 1500, 2000, 3000, 4000, 5000, or more consecutive nucleotides of a nucleic acid according to the invention.

As used herein, an "isolated nucleic acid fragment" refers to a polymer of RNA or DNA that is single- or double-stranded, optionally containing synthetic, non-natural or altered nucleotide bases. An isolated nucleic acid fragment in the form of a polymer of DNA may be comprised of one or more segments of cDNA, genomic DNA or synthetic DNA.

A "gene" refers to a polynucleotide comprising nucleotides that encode a functional molecule, including functional molecules produced by transcription only (e.g., a bioactive RNA species) or by transcription and translation (e.g., a polypeptide). The term "gene" encompasses cDNA and genomic DNA nucleic acids. "Gene" also refers to a nucleic acid fragment that expresses a specific RNA, protein or polypeptide, including regulatory sequences preceding (5' non-coding sequences) and following (3' non-coding sequences) the coding sequence. "Native gene" refers to a gene as found in nature with its own regulatory sequences. "Chimeric gene" refers to any gene that is not a native gene, comprising regulatory and/or coding sequences that are not found together in nature. Accordingly, a chimeric gene may comprise regulatory sequences and coding sequences that are derived from different sources, or regulatory sequences and coding sequences derived from the same source, but arranged in a manner different than that found in nature. A chimeric gene may comprise coding sequences derived from different sources and/or regulatory sequences derived from different sources. "Endogenous gene" refers to a native gene in its natural location in the genome of an organism. A "foreign" gene or "heterologous" gene refers to a gene not normally found in the host organism, but that is introduced into the host organism by gene transfer. Foreign genes can comprise native genes inserted into a non-native organism, or chimeric genes. A "transgene" is a gene that has been introduced into the genome by a transformation procedure. For example, the interleukin-12 (IL-12) gene encodes the IL-12 protein. IL-12 is a heterodimer of a 35-kD subunit (p35) and a 40-kD subunit (p40) linked through a disulfide linkage to make fully functional IL-12p70. The IL-12 gene encodes both the p35 and p40 subunits.

"Heterologous DNA" refers to DNA not naturally located in the cell, or in a chromosomal site of the cell. The heterologous DNA may include a gene foreign to the cell.

The term "genome" includes chromosomal as well as mitochondrial, chloroplast and viral DNA or RNA.

A nucleic acid molecule is "hybridizable" to another nucleic acid molecule, such as a cDNA, genomic DNA, or RNA, when a single stranded form of the nucleic acid molecule can anneal to the other nucleic acid molecule under the appropriate conditions of temperature and solution ionic strength. Hybridization and washing conditions are well known and exemplified in Sambrook et al. in *Molecular Cloning: A Laboratory Manual*, Second Edition, Cold Spring Harbor Laboratory Press, Cold Spring Harbor (1989), particularly Chapter 11 and Table 11.1 therein. The conditions of temperature and ionic strength determine the "stringency" of the hybridization.

Stringency conditions can be adjusted to screen for moderately similar fragments, such as homologous sequences from distantly related organisms, to highly similar fragments, such as genes that duplicate functional enzymes from closely related organisms. For preliminary screening for homologous nucleic acids, low stringency hybridization conditions, corresponding to a $T_m$ of 55°, can be used, e.g., 5×SSC, 0.1% SDS, 0.25% milk, and no formamide; or 30% formamide, 5×SSC, 0.5% SDS. Moderate stringency hybridization conditions correspond to a higher $T_m$, e.g., 40% formamide, with 5× or 6×SSC. High stringency hybridization conditions correspond to the highest $T_m$, e.g., 50% formamide, 5× or 6×SSC.

Hybridization requires that the two nucleic acids contain complementary sequences, although depending on the stringency of the hybridization, mismatches between bases are possible. The term "complementary" is used to describe the relationship between nucleotide bases that are capable of hybridizing to one another. For example, with respect to DNA, adenosine is complementary to thymine and cytosine is complementary to guanine. Accordingly, the invention also includes isolated nucleic acid fragments that are complementary to the complete sequences as disclosed or used herein as well as those substantially similar nucleic acid sequences.

In one embodiment of the invention, polynucleotides are detected by employing hybridization conditions comprising a hybridization step at $T_m$ of 55° C., and utilizing conditions as set forth above. In other embodiments, the $T_m$ is 60° C., 63° C., or 65° C.

Post-hybridization washes also determine stringency conditions. One set of conditions uses a series of washes starting with 6×SSC, 0.5% SDS at room temperature for 15 minutes (min), then repeated with 2×SSC, 0.5% SDS at 45° C. for 30 min, and then repeated twice with 0.2×SSC, 0.5% SDS at 50° C. for 30 min. A preferred set of stringent conditions uses higher temperatures in which the washes are identical to those above except for the temperature of the final two 30 min washes in 0.2×SSC, 0.5% SDS is increased to 60° C. Another preferred set of highly stringent conditions uses two final washes in 0.1×SSC, 0.1% SDS at 65° C.

The appropriate stringency for hybridizing nucleic acids depends on the length of the nucleic acids and the degree of complementation, variables well known in the art. The greater the degree of similarity or homology between two nucleotide sequences, the greater the value of $T_m$ for hybrids of nucleic acids having those sequences. The relative stability (corresponding to higher $T_m$) of nucleic acid hybridizations decreases in the following order: RNA:RNA, DNA:RNA, DNA:DNA. For hybrids of greater than 100 nucleotides in length, equations for calculating $T_n$, have been derived (see Sambrook et al., supra, 9.50-0.51). For hybridization with shorter nucleic acids, i.e., oligonucleotides, the position of mismatches becomes more important, and the length of the oligonucleotide determines its specificity (see Sambrook et al., supra, 11.7-11.8).

In one embodiment of the invention, polynucleotides are detected by employing hybridization conditions comprising a hybridization step in less than 500 mM salt and at least 37° C., and a washing step in 2×SSPE at a temperature of at least 63° C. In another embodiment, the hybridization conditions comprise less than 200 mM salt and at least 37° C. for the hybridization step. In a further embodiment, the hybridization conditions comprise 2×SSPE and 63° C. for both the hybridization and washing steps.

In another embodiment, the length for a hybridizable nucleic acid is at least about 10 nucleotides. Preferably a minimum length for a hybridizable nucleic acid is at least about 15 nucleotides; e.g., at least about 20 nucleotides; e.g., at least 30 nucleotides. Furthermore, the skilled artisan will recognize that the temperature and wash solution salt concentration may be adjusted as necessary according to factors such as length of the probe.

The term "probe" refers to a single-stranded nucleic acid molecule that can base pair with a complementary single stranded target nucleic acid to form a double-stranded molecule.

As used herein, the term "oligonucleotide" refers to a short nucleic acid that is hybridizable to a genomic DNA molecule, a cDNA molecule, a plasmid DNA or an mRNA molecule. Oligonucleotides can be labeled, e.g., with $^{32}$P-nucleotides or nucleotides to which a label, such as biotin, has been covalently conjugated. A labeled oligonucleotide can be used as a probe to detect the presence of a nucleic acid. Oligonucleotides (one or both of which may be labeled) can be used as PCR primers, either for cloning full length or a fragment of a nucleic acid, for DNA sequencing, or to detect the presence of a nucleic acid. An oligonucleotide can also be used to form a triple helix with a DNA molecule. Generally, oligonucleotides are prepared synthetically, preferably on a nucleic acid synthesizer. Accordingly, oligonucleotides can be prepared with non-naturally occurring phosphoester analog bonds, such as thioester bonds, etc.

A "primer" refers to an oligonucleotide that hybridizes to a target nucleic acid sequence to create a double stranded nucleic acid region that can serve as an initiation point for DNA synthesis under suitable conditions. Such primers may be used in a polymerase chain reaction or for DNA sequencing.

"Polymerase chain reaction" is abbreviated PCR and refers to an in vitro method for enzymatically amplifying specific nucleic acid sequences. PCR involves a repetitive series of temperature cycles with each cycle comprising three stages: denaturation of the template nucleic acid to separate the strands of the target molecule, annealing a single stranded PCR oligonucleotide primer to the template nucleic acid, and extension of the annealed primer(s) by DNA polymerase. PCR provides a means to detect the presence of the target molecule and, under quantitative or semi-quantitative conditions, to determine the relative amount of that target molecule within the starting pool of nucleic acids.

"Reverse transcription-polymerase chain reaction" is abbreviated RT-PCR and refers to an in vitro method for enzymatically producing a target cDNA molecule or molecules from an RNA molecule or molecules, followed by enzymatic amplification of a specific nucleic acid sequence or sequences within the target cDNA molecule or molecules as described above. RT-PCR also provides a means to detect the presence of the target molecule and, under quantitative or semi-quantitative conditions, to determine the relative amount of that target molecule within the starting pool of nucleic acids.

A DNA "coding sequence" refers to a double-stranded DNA sequence that encodes a polypeptide and can be transcribed and translated into a polypeptide in a cell in vitro or in vivo when placed under the control of suitable regulatory sequences. "Suitable regulatory sequences" refers to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include promoters, translation leader sequences, introns, polyadenylation recognition sequences, RNA processing sites, effector binding sites and stem-loop structures. The boundaries of the coding sequence are determined by a start codon at the 5' (amino) terminus and a translation stop codon at the 3' (carboxyl) terminus. A coding sequence can include, but is not limited to, prokaryotic sequences, cDNA from mRNA, genomic DNA sequences, and even synthetic DNA sequences. If the coding sequence is intended for expression in an eukaryotic cell, a polyadenylation signal and transcription termination sequence will usually be located 3' to the coding sequence.

"Open reading frame" is abbreviated ORF and refers to a length of nucleic acid sequence, either DNA, cDNA or RNA, that comprises a translation start signal or initiation codon, such as an ATG or AUG, and a termination codon and can be potentially translated into a polypeptide sequence.

The term "head-to-head" is used herein to describe the orientation of two polynucleotide sequences in relation to each other. Two polynucleotides are positioned in a head-to-head orientation when the 5' end of the coding strand of one polynucleotide is adjacent to the 5' end of the coding strand of the other polynucleotide, whereby the direction of transcription of each polynucleotide proceeds away from the 5' end of the other polynucleotide. The term "head-to-head" may be abbreviated (5')-to-(5') and may also be indicated by the symbols (← →) or (3'←5'5'→3').

The term "tail-to-tail" is used herein to describe the orientation of two polynucleotide sequences in relation to each other. Two polynucleotides are positioned in a tail-to-tail orientation when the 3' end of the coding strand of one polynucleotide is adjacent to the 3' end of the coding strand of the other polynucleotide, whereby the direction of transcription of each polynucleotide proceeds toward the other polynucleotide. The term "tail-to-tail" may be abbreviated (3')-to-(3') and may also be indicated by the symbols (→ ←) or (5'→3'3'←5').

The term "head-to-tail" is used herein to describe the orientation of two polynucleotide sequences in relation to each other. Two polynucleotides are positioned in a head-to-tail orientation when the 5' end of the coding strand of one polynucleotide is adjacent to the 3' end of the coding strand of the other polynucleotide, whereby the direction of transcription of each polynucleotide proceeds in the same direction as that of the other polynucleotide. The term "head-to-tail" may be abbreviated (5')-to-(3') and may also be indicated by the symbols (→ →) or (5'→3'5'→3').

The term "downstream" refers to a nucleotide sequence that is located 3' to a reference nucleotide sequence. In particular, downstream nucleotide sequences generally relate to sequences that follow the starting point of transcription. For example, the translation initiation codon of a gene is located downstream of the start site of transcription.

The term "upstream" refers to a nucleotide sequence that is located 5' to a reference nucleotide sequence. In particular, upstream nucleotide sequences generally relate to sequences that are located on the 5' side of a coding sequence or starting point of transcription. For example, most promoters are located upstream of the start site of transcription.

The terms "restriction endonuclease" and "restriction enzyme" are used interchangeably and refer to an enzyme that binds and cuts within a specific nucleotide sequence within double stranded DNA.

"Homologous recombination" refers to the insertion of a foreign DNA sequence into another DNA molecule, e.g., insertion of a vector in a chromosome. Preferably, the vector targets a specific chromosomal site for homologous recombination. For specific homologous recombination, the vector will contain sufficiently long regions of homology to sequences of the chromosome to allow complementary binding and incorporation of the vector into the chromosome. Longer regions of homology, and greater degrees of sequence similarity, may increase the efficiency of homologous recombination.

Several methods known in the art may be used to propagate a polynucleotide according to the invention. Once a suitable host system and growth conditions are established, recombinant expression vectors can be propagated and prepared in quantity. As described herein, the expression vectors which can be used include, but are not limited to, the following vectors or their derivatives: human or animal viruses such as vaccinia virus or adenovirus; insect viruses such as baculovirus; yeast vectors; bacteriophage vectors (e.g., lambda), and plasmid and cosmid DNA vectors, to name but a few.

A "vector" refers to any vehicle for the cloning of and/or transfer of a nucleic acid into a host cell. A vector may be a replicon to which another DNA segment may be attached so as to bring about the replication of the attached segment. A "replicon" refers to any genetic element (e.g., plasmid, phage, cosmid, chromosome, virus) that functions as an autonomous unit of DNA replication in vivo, i.e., capable of replication under its own control. The term "vector" includes both viral and nonviral vehicles for introducing the nucleic acid into a cell in vitro, ex vivo or in vivo. A large number of vectors known in the art may be used to manipulate nucleic acids, incorporate response elements and promoters into genes, etc. Possible vectors include, for example, plasmids or modified viruses including, for example bacteriophages such as lambda derivatives, or plasmids such as pBR322 or pUC plasmid derivatives, or the Bluescript vector. Another example of vectors that are useful in the invention is the UltraVector™ Production System (Intrexon Corp., Blacksburg, Va.) as described in WO 2007/038276. For example, the insertion of the DNA fragments corresponding to response elements and promoters into a suitable vector can be accomplished by ligating the appropriate DNA fragments into a chosen vector that has complementary cohesive termini. Alternatively, the ends of the DNA molecules may be enzymatically modified or any site may be produced by ligating nucleotide sequences (linkers) into the DNA termini. Such vectors may be engineered to contain selectable marker genes that provide for the selection of cells that have incorporated the marker into the cellular genome. Such markers allow identification and/or selection of host cells that incorporate and express the proteins encoded by the marker.

Viral vectors, and particularly retroviral vectors, have been used in a wide variety of gene delivery applications in cells, as well as living animal subjects. Viral vectors that can be used include, but are not limited to, retrovirus, adeno-associated virus, pox, baculovirus, vaccinia, herpes simplex, Epstein-Barr, adenovirus, geminivirus, and caulimovirus vectors. Non-viral vectors include plasmids, liposomes, electrically charged lipids (cytofectins), DNA-protein complexes, and biopolymers. In addition to a nucleic acid, a vector may also comprise one or more regulatory regions, and/or selectable markers useful in selecting, measuring, and monitoring nucleic acid transfer results (transfer to which tissues, duration of expression, etc.).

The term "plasmid" refers to an extra-chromosomal element often carrying a gene that is not part of the central metabolism of the cell, and usually in the form of circular double-stranded DNA molecules. Such elements may be autonomously replicating sequences, genome integrating sequences, phage or nucleotide sequences, linear, circular, or supercoiled, of a single- or double-stranded DNA or RNA, derived from any source, in which a number of nucleotide sequences have been joined or recombined into a unique construction which is capable of introducing a promoter fragment and DNA sequence for a selected gene product along with appropriate 3' untranslated sequence into a cell.

A "cloning vector" refers to a "replicon," which is a unit length of a nucleic acid, preferably DNA, that replicates sequentially and which comprises an origin of replication, such as a plasmid, phage or cosmid, to which another nucleic acid segment may be attached so as to bring about the replication of the attached segment. Cloning vectors may be capable of replication in one cell type and expression in another ("shuttle vector"). Cloning vectors may comprise one or more sequences that can be used for selection of cells comprising the vector and/or one or more multiple cloning sites for insertion of sequences of interest.

The term "expression vector" refers to a vector, plasmid or vehicle designed to enable the expression of an inserted nucleic acid sequence following transformation into the host. The cloned gene, i.e., the inserted nucleic acid sequence, is usually placed under the control of control elements such as a promoter, a minimal promoter, an enhancer, or the like. Initiation control regions or promoters, which are useful to drive expression of a nucleic acid in the desired host cell are numerous and familiar to those skilled in the art. Virtually any promoter capable of driving expression of these genes can be used in an expression vector, including but not limited to, viral promoters, bacterial promoters, animal promoters, mammalian promoters, synthetic promoters, constitutive promoters, tissue specific promoters, pathogenesis or disease related promoters, developmental specific promoters, inducible promoters, light regulated promoters; CYC1, HIS3, GAL1, GAL4, GAL10, ADH1, PGK, PHO5, GAPDH, ADC1, TRP1, URA3, LEU2, ENO, TPI, alkaline phosphatase promoters (useful for expression in *Saccharomyces*); AOX1 promoter (useful for expression in *Pichia*); β-lactamase, lac, ara, tet, trp, $IP_L$, $IP_R$, T7, tac, and trc promoters (useful for expression in *Escherichia coli*); light regulated-, seed specific-, pollen specific-, ovary specific-, cauliflower mosaic virus 35S, CMV 35S minimal, cassava vein mosaic virus (CsVMV), chlorophyll a/b binding protein, ribulose 1,5-bisphosphate carboxylase, shoot-specific, root specific, chitinase, stress inducible, rice tungro bacilliform virus, plant super-promoter, potato leucine aminopeptidase, nitrate reductase, mannopine synthase, nopaline synthase, ubiquitin, zein protein, and anthocyanin promoters (useful for expression in plant cells); animal and mammalian promoters known in the art including, but are not limited to, the SV40 early (SV40e) promoter region, the promoter contained in the 3' long terminal repeat (LTR) of Rous sarcoma virus (RSV), the promoters of the E1A or major late promoter (MLP) genes of adenoviruses (Ad), the cytomegalovirus (CMV) early promoter, the herpes simplex virus (HSV) thymidine kinase (TK) promoter, a baculovirus IE1 promoter, an elongation factor 1 alpha (EF1) promoter, a phosphoglycerate kinase (PGK) promoter, a ubiquitin (Ubc) promoter, an albumin promoter, the regulatory sequences of the mouse metallothionein-L promoter and transcriptional control regions, the ubiquitous promoters (HPRT, vimentin, α-actin, tubulin and the like), the promoters of the intermediate filaments (desmin, neurofilaments, keratin, GFAP, and the like), the promoters of therapeutic genes (of the MDR, CFTR or factor VIII type, and the like), pathogenesis or disease related-promoters, and promoters that exhibit tissue specificity and have been utilized in transgenic animals, such as the elastase I gene control region which is active in pancreatic acinar cells; insulin gene control region active in pancreatic beta cells, immunoglobulin gene control region active in lymphoid cells, mouse mammary tumor virus control region active in testicular, breast, lymphoid and mast cells; albumin gene, Apo AI and Apo AII control regions active in liver, alpha-fetoprotein gene control region active in liver, alpha 1-antitrypsin gene control region active in the liver, beta-globin gene control region active in myeloid cells, myelin basic protein gene control region active in oligodendrocyte cells in the brain, myosin light chain-2 gene control region active in skeletal muscle, and gonadotropic releasing hormone gene control region active in the hypothalamus, pyruvate kinase promoter, villin promoter, promoter of the fatty acid binding intestinal protein, promoter of the smooth muscle cell α-actin, and the like. In addition, these expression sequences may be modified by addition of enhancer or regulatory sequences and the like.

Vectors may be introduced into the desired host cells by methods known in the art, e.g., transfection, electroporation, microinjection, transduction, cell fusion, DEAE dextran, calcium phosphate precipitation, lipofection (lysosome fusion), use of a gene gun, or a DNA vector transporter (see, e.g., Wu et al., *J. Biol. Chem.* 267:963 (1992); Wu et al., *J. Biol. Chem.* 263:14621 (1988); and Hartmut et al., Canadian Patent Application No. 2,012,311).

A polynucleotide according to the invention can also be introduced in vivo by lipofection. For the past decade, there has been increasing use of liposomes for encapsulation and transfection of nucleic acids in vitro. Synthetic cationic lipids designed to limit the difficulties and dangers encountered with liposome-mediated transfection can be used to prepare liposomes for in vivo transfection of a gene encoding a marker (Feigner et al., *Proc. Natl. Acad. Sci. USA.* 84:7413 (1987); Mackey et al., *Proc. Natl. Acad. Sci. USA* 85:8027 (1988); and Ulmer et al., *Science* 259:1745 (1993)). The use of cationic lipids may promote encapsulation of negatively charged nucleic acids, and also promote fusion with negatively charged cell membranes (Feigner et al., *Science* 337:387 (1989)). Particularly useful lipid compounds and compositions for transfer of nucleic acids are described in WO95/18863, WO96/17823 and U.S. Pat. No. 5,459,127. The use of lipofection to introduce exogenous genes into the specific organs in vivo has certain practical advantages. Molecular targeting of liposomes to specific cells represents one area of benefit. It is clear that directing transfection to particular cell types would be particularly preferred in a tissue with cellular heterogeneity, such as pancreas, liver, kidney, and the brain. Lipids may be chemically coupled to other molecules for the purpose of targeting (Mackey et al. 1988, supra). Targeted peptides, e.g., hormones or neurotransmitters, and proteins such as antibodies, or non-peptide molecules could be coupled to liposomes chemically.

Other molecules are also useful for facilitating transfection of a nucleic acid in vivo, such as a cationic oligopeptide (e.g., WO95/21931), peptides derived from DNA binding proteins (e.g., WO96/25508), or a cationic polymer (e.g., WO95/21931).

It is also possible to introduce a vector in vivo as a naked DNA plasmid (see U.S. Pat. Nos. 5,693,622, 5,589,466 and 5,580,859). Receptor-mediated DNA delivery approaches can also be used (Curiel et al., *Hum. Gene Ther.* 3:147 (1992); and Wu et al., *J. Biol. Chem.* 262:4429 (1987)).

The term "transfection" refers to the uptake of exogenous or heterologous RNA or DNA by a cell. A cell has been "transfected" by exogenous or heterologous RNA or DNA when such RNA or DNA has been introduced inside the cell. A cell has been "transformed" by exogenous or heterologous RNA or DNA when the transfected RNA or DNA effects a phenotypic change. The transforming RNA or DNA can be integrated (covalently linked) into chromosomal DNA making up the genome of the cell.

"Transformation" refers to the transfer of a nucleic acid fragment into the genome of a host organism, resulting in genetically stable inheritance. Host organisms containing the transformed nucleic acid fragments are referred to as "transgenic" or "recombinant" or "transformed" organisms.

In addition, the recombinant vector comprising a polynucleotide according to the invention may include one or more origins for replication in the cellular hosts in which their amplification or their expression is sought, markers or selectable markers.

The term "selectable marker" refers to an identifying factor, usually an antibiotic or chemical resistance gene, that is able to be selected for based upon the marker gene's effect, i.e., resistance to an antibiotic, resistance to a herbicide, colorimetric markers, enzymes, fluorescent markers, and the like, wherein the effect is used to track the inheritance of a nucleic acid of interest and/or to identify a cell or organism that has inherited the nucleic acid of interest. Examples of selectable marker genes known and used in the art include: genes providing resistance to ampicillin, streptomycin, gentamycin, kanamycin, hygromycin, bialaphos herbicide, sulfonamide, and the like; and genes that are used as phenotypic markers, i.e., anthocyanin regulatory genes, isopentanyl transferase gene, and the like.

The term "reporter gene" refers to a nucleic acid encoding an identifying factor that is able to be identified based upon the reporter gene's effect, wherein the effect is used to track the inheritance of a nucleic acid of interest, to identify a cell or organism that has inherited the nucleic acid of interest, and/or to measure gene expression induction or transcription. Examples of reporter genes known and used in the art include: luciferase (Luc), green fluorescent protein (GFP), chloramphenicol acetyltransferase (CAT), β-galactosidase (LacZ), β-glucuronidase (Gus), and the like. Selectable marker genes may also be considered reporter genes.

"Promoter" and "promoter sequence" are used interchangeably and refer to a DNA sequence capable of controlling the expression of a coding sequence or functional RNA. In general, a coding sequence is located 3' to a promoter sequence. Promoters may be derived in their entirety from a native gene, or be composed of different elements derived from different promoters found in nature, or even comprise synthetic DNA segments. It is understood by those skilled in the art that different promoters may direct the expression of a gene in different tissues or cell types, or at different stages of development, or in response to different environmental or physiological conditions. Promoters that cause a gene to be expressed in most cell types at most times are commonly referred to as "constitutive promoters." Promoters that cause a gene to be expressed in a specific cell type are commonly referred to as "cell-specific promoters" or "tissue-specific promoters." Promoters that cause a gene to be expressed at a specific stage of development or cell differentiation are commonly referred to as "developmentally-specific promoters" or "cell differentiation-specific promoters." Promoters that are induced and cause a gene to be expressed following exposure or treatment of the cell with an agent, biological molecule, chemical, ligand, light, or the like that induces the promoter are commonly referred to as "inducible promoters" or "regulatable promoters." It is further recognized that since in most cases the exact boundaries of regulatory sequences have not been completely defined, DNA fragments of different lengths may have identical promoter activity.

The promoter sequence is typically bounded at its 3' terminus by the transcription initiation site and extends upstream (5' direction) to include the minimum number of bases or elements necessary to initiate transcription at levels detectable above background. Within the promoter sequence will be found a transcription initiation site (conveniently defined for example, by mapping with nuclease S1), as well as protein binding domains (consensus sequences) responsible for the binding of RNA polymerase.

A coding sequence is "under the control" of transcriptional and translational control sequences in a cell when RNA polymerase transcribes the coding sequence into mRNA, which is then trans-RNA spliced (if the coding sequence contains introns) and translated into the protein encoded by the coding sequence.

"Transcriptional and translational control sequences" refer to DNA regulatory sequences, such as promoters, enhancers, terminators, and the like, that provide for the expression of a coding sequence in a host cell. In eukaryotic cells, polyadenylation signals are control sequences.

The term "response element" refers to one or more cis-acting DNA elements which confer responsiveness on a promoter mediated through interaction with the DNA-binding domains of a transcription factor. This DNA element may be either palindromic (perfect or imperfect) in its sequence or composed of sequence motifs or half sites separated by a variable number of nucleotides. The half sites can be similar or identical and arranged as either direct or inverted repeats or as a single half site or multimers of adjacent half sites in tandem. The response element may comprise a minimal promoter isolated from different organisms depending upon the nature of the cell or organism into which the response element will be incorporated. The DNA binding domain of the transcription factor binds, in the presence or absence of a ligand, to the DNA sequence of a response element to initiate or suppress transcription of downstream gene(s) under the regulation of this response element. Examples of DNA sequences for response elements of the natural ecdysone receptor include: RRGG/TTCANTGAC/ACYY (SEQ ID NO: 9) (see Cherbas et. al., Genes Dev. 5:120 (1991)); AGGTCAN$_{(n)}$AGGTCA, where N$_{(n)}$ can be one or more spacer nucleotides (SEQ ID NO: 10) (see D'Avino et al., Mol. Endocrinol. 113:1 (1995)); and GGGTTGAATGAATTT (SEQ ID NO: 11) (see Antoniewski et al., Mol. Cell Biol. 14:4465 (1994)).

The term "operably linked" refers to the association of nucleic acid sequences on a single nucleic acid fragment so that the function of one is affected by the other. For example, a promoter is operably linked with a coding sequence when it is capable of affecting the expression of that coding sequence (i.e., that coding sequence is under the transcriptional control of the promoter). Coding sequences can be operably linked to regulatory sequences in sense or antisense orientation.

The term "expression" as used herein refers to the transcription and stable accumulation of sense (mRNA) or antisense RNA derived from a nucleic acid or polynucleotide. Expression may also refer to translation of mRNA into a protein or polypeptide.

The terms "cassette," "expression cassette" and "gene expression cassette" refer to a segment of DNA that can be inserted into a nucleic acid or polynucleotide at specific restriction sites or by homologous recombination. The segment of DNA comprises a polynucleotide that encodes a polypeptide of interest, and the cassette and restriction sites are designed to ensure insertion of the cassette in the proper reading frame for transcription and translation. "Transformation cassette" refers to a specific vector comprising a polynucleotide that encodes a polypeptide of interest and having elements in addition to the polynucleotide that facilitate transformation of a particular host cell. Cassettes, expression cassettes, gene expression cassettes and transformation cassettes of the invention may also comprise elements that allow for enhanced expression of a polynucleotide encoding a polypeptide of interest in a host cell. These elements may include, but are not limited to: a promoter, a minimal promoter, an enhancer, a response element, a terminator sequence, a polyadenylation sequence, and the like.

For purposes of this invention, the term "gene switch" refers to the combination of a response element associated with a promoter, and a ligand-dependent transcription factor-based system which, in the presence of one or more ligands, modulates the expression of a gene into which the response element and promoter are incorporated. The term "a polynucleotide encoding a gene switch" refers to the combination of a response element associated with a promoter, and a polynucleotide encoding a ligand-dependent transcription factor-based system which, in the presence of one or more ligands, modulates the expression of a gene into which the response element and promoter are incorporated.

Figure 1:
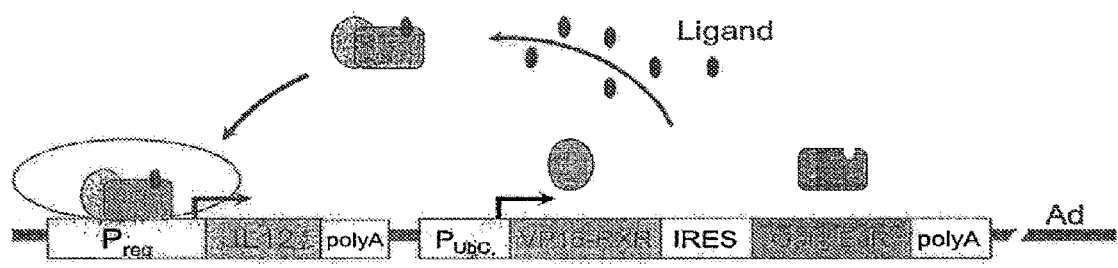
FIG. 1 shows the structure of the vector rAd.RheoIL12 in which the E1 and E3 regions have been deleted and the RheoSwitch® Therapeutic System (RTS)—IL-12 components replace the E1 region. The box labeled "IL12" represents the IL-12p40 and IL-12p35 coding sequences separated by IRES.

The term "ecdysone receptor-based," with respect to a gene switch, refers to a gene switch comprising at least a functional part of a naturally occurring or synthetic ecdysone receptor ligand binding domain and which regulates gene expression in response to a ligand that binds to the ecdysone receptor ligand binding domain. Examples of ecdysone-responsive systems are described in U.S. Pat. Nos. 7,091,038 and 6,258,603. In one embodiment, the system is the RheoSwitch® Therapeutic System (RTS), which contains two fusion proteins, the DEF domains of a mutagenized ecdysone receptor (EcR) fused with a Gal4 DNA binding domain and the EF domains of a chimeric RXR fused with a VP16 transcription activation domain, expressed under a constitutive promoter as illustrated in FIG. 1.

The terms "modulate" and "modulates" mean to induce, reduce or inhibit nucleic acid or gene expression, resulting in the respective induction, reduction or inhibition of protein or polypeptide production.

The polynucleotides or vectors according to the invention may further comprise at least one promoter suitable for driving expression of a gene in a host cell.

Enhancers that may be used in embodiments of the invention include but are not limited to: an SV40 enhancer, a cytomegalovirus (CMV) enhancer, an elongation factor 1 (EF1) enhancer, yeast enhancers, viral gene enhancers, and the like.

Termination control regions, i.e., terminator or polyadenylation sequences, may also be derived from various genes native to the preferred hosts. Optionally, a termination site may be unnecessary, however, it is most preferred if included. In one embodiment of the invention, the termination control region may be comprised or be derived from a synthetic sequence, synthetic polyadenylation signal, an SV40 late polyadenylation signal, an SV40 polyadenylation signal, a bovine growth hormone (BGH) polyadenylation signal, viral terminator sequences, or the like.

The terms "3' non-coding sequences" or "3' untranslated region (UTR)" refer to DNA sequences located downstream (3') of a coding sequence and may comprise polyadenylation [poly(A)] recognition sequences and other sequences encoding regulatory signals capable of affecting mRNA processing or gene expression. The polyadenylation signal is usually characterized by affecting the addition of polyadenylic acid tracts to the 3' end of the mRNA precursor.

"Regulatory region" refers to a nucleic acid sequence that regulates the expression of a second nucleic acid sequence. A regulatory region may include sequences which are naturally responsible for expressing a particular nucleic acid (a homologous region) or may include sequences of a different origin that are responsible for expressing different proteins or even synthetic proteins (a heterologous region). In particular, the sequences can be sequences of prokaryotic, eukaryotic, or viral genes or derived sequences that stimulate or repress transcription of a gene in a specific or non-specific manner and in an inducible or non-inducible manner. Regulatory regions include origins of replication, RNA splice sites, promoters, enhancers, transcriptional termination sequences, and signal sequences which direct the polypeptide into the secretory pathways of the target cell.

A regulatory region from a "heterologous source" refers to a regulatory region that is not naturally associated with the expressed nucleic acid. Included among the heterologous regulatory regions are regulatory regions from a different species, regulatory regions from a different gene, hybrid regulatory sequences, and regulatory sequences which do not occur in nature, but which are designed by one having ordinary skill in the art.

"RNA transcript" refers to the product resulting from RNA polymerase-catalyzed transcription of a DNA sequence. When the RNA transcript is a perfect complementary copy of the DNA sequence, it is referred to as the primary transcript or it may be a RNA sequence derived from post-transcriptional processing of the primary transcript and is referred to as the mature RNA. "Messenger RNA (mRNA)" refers to the RNA that is without introns and that can be translated into protein by the cell. "cDNA" refers to a double-stranded DNA that is complementary to and derived from mRNA. "Sense" RNA refers to RNA transcript that includes the mRNA and so can be translated into protein by the cell. "Antisense RNA" refers to a RNA transcript that is complementary to all or part of a target primary transcript or mRNA and that blocks the expression of a target gene. The complementarity of an antisense RNA may be with any part of the specific gene transcript, i.e., at the 5' non-coding sequence, 3' non-coding sequence, or the coding sequence. "Functional RNA" refers to antisense RNA, ribozyme RNA, or other RNA that is not translated yet has an effect on cellular processes.

"Polypeptide," "peptide" and "protein" are used interchangeably and refer to a polymeric compound comprised of covalently linked amino acid residues.

An "isolated polypeptide," "isolated peptide" or "isolated protein" refer to a polypeptide or protein that is substantially free of those compounds that are normally associated therewith in its natural state (e.g., other proteins or polypeptides, nucleic acids, carbohydrates, lipids). "Isolated" is not meant to exclude artificial or synthetic mixtures with other compounds, or the presence of impurities which do not interfere with biological activity, and which may be present, for example, due to incomplete purification, addition of stabilizers, or compounding into a pharmaceutically acceptable preparation.

A "substitution mutant polypeptide" or a "substitution mutant" will be understood to mean a mutant polypeptide comprising a substitution of at least one wild-type or naturally occurring amino acid with a different amino acid relative to the wild-type or naturally occurring polypeptide. A substitution mutant polypeptide may comprise only one wild-type or naturally occurring amino acid substitution and may be referred to as a "point mutant" or a "single point mutant" polypeptide. Alternatively, a substitution mutant polypeptide may comprise a substitution of two or more wild-type or naturally occurring amino acids with two or more amino acids relative to the wild-type or naturally occurring polypeptide. According to the invention, a Group H nuclear receptor ligand binding domain polypeptide comprising a substitution mutation comprises a substitution of at least one wild-type or naturally occurring amino acid with a different amino acid relative to the wild-type or naturally occurring Group H nuclear receptor ligand binding domain polypeptide.

When the substitution mutant polypeptide comprises a substitution of two or more wild-type or naturally occurring amino acids, this substitution may comprise either an equivalent number of wild-type or naturally occurring amino acids deleted for the substitution, i.e., 2 wild-type or naturally occurring amino acids replaced with 2 non-wild-type or non-naturally occurring amino acids, or a non-equivalent number of wild-type amino acids deleted for the substitution, i.e., 2 wild-type amino acids replaced with 1 non-wild-type amino acid (a substitution+deletion mutation), or 2 wild-type amino acids replaced with 3 non-wild-type amino acids (a substitution+insertion mutation).

Substitution mutants may be described using an abbreviated nomenclature system to indicate the amino acid residue and number replaced within the reference polypeptide sequence and the new substituted amino acid residue. For example, a substitution mutant in which the twentieth ($20^{th}$) amino acid residue of a polypeptide is substituted may be abbreviated as "x20z", wherein "x" is the amino acid to be replaced, "20" is the amino acid residue position or number within the polypeptide, and "z" is the new substituted amino acid. Therefore, a substitution mutant abbreviated interchangeably as "E20A" or "Glu20Ala" indicates that the mutant comprises an alanine residue (commonly abbreviated in the art as "A" or "Ala") in place of the glutamic acid (commonly abbreviated in the art as "E" or "Glu") at position 20 of the polypeptide.

A substitution mutation may be made by any technique for mutagenesis known in the art, including but not limited to, in vitro site-directed mutagenesis (Hutchinson et al., *J. Biol. Chem.* 253:6551 (1978); Zoller et al., DNA 3:479 (1984); Oliphant et al., *Gene* 44:177 (1986); Hutchinson et al., *Proc. Natl. Acad. Sci. USA* 83:710 (1986)), use of TAB® linkers (Pharmacia), restriction endonuclease digestion/fragment deletion and substitution, PCR-mediated/oligonucleotide-directed mutagenesis, and the like. PCR-based techniques are preferred for site-directed mutagenesis (see Higuchi, 1989, "Using PCR to Engineer DNA", in *PCR Technology: Principles and Applications for DNA Amplification*, H. Erlich, ed., Stockton Press, Chapter 6, pp. 61-70).

The term "fragment," as applied to a polypeptide, refers to a polypeptide whose amino acid sequence is shorter than that of the reference polypeptide and which comprises, over the entire portion with these reference polypeptides, an identical amino acid sequence. Such fragments may, where appropriate, be included in a larger polypeptide of which they are a part. Such fragments of a polypeptide according to the invention may have a length of at least 2, 3, 4, 5, 6, 8, 10, 13, 14, 15, 16, 17, 18, 19, 20, 21, 22, 25, 26, 30, 35, 40, 45, 50, 100, 200, 240, or 300 or more amino acids.

A "variant" of a polypeptide or protein refers to any analogue, fragment, derivative, or mutant which is derived from a polypeptide or protein and which retains at least one biological property of the polypeptide or protein. Different variants of the polypeptide or protein may exist in nature. These variants may be allelic variations characterized by differences in the nucleotide sequences of the structural gene coding for the protein, or may involve differential splicing or post-translational modification. The skilled artisan can produce variants having single or multiple amino acid substitutions, deletions, additions, or replacements. These variants may include, inter alia: (a) variants in which one or more amino acid residues are substituted with conservative or non-conservative amino acids, (b) variants in which one or more amino acids are added to the polypeptide or protein, (c) variants in which one or more of the amino acids includes a substituent group, and (d) variants in which the polypeptide or protein is fused with another polypeptide such as serum albumin. The techniques for obtaining these variants, including genetic (suppressions, deletions, mutations, etc.), chemical, and enzymatic techniques, are known to persons having ordinary skill in the art. In one embodiment, a variant polypeptide comprises at least about 14 amino acids.

The term "homology" refers to the percent of identity between two polynucleotide or two polypeptide moieties. The correspondence between the sequence from one moiety to another can be determined by techniques known to the art. For example, homology can be determined by a direct comparison of the sequence information between two polypeptide molecules by aligning the sequence information and using readily available computer programs. Alternatively, homology can be determined by hybridization of polynucleotides under conditions that form stable duplexes between homologous regions, followed by digestion with single-stranded-specific nuclease(s) and size determination of the digested fragments.

As used herein, the term "homologous" in all its grammatical forms and spelling variations refers to the relationship between proteins that possess a "common evolutionary origin," including proteins from superfamilies (e.g., the immunoglobulin superfamily) and homologous proteins from different species (e.g., myosin light chain, etc.) (Reeck et al., Cell 50:667 (1987)). Such proteins (and their encoding genes) have sequence homology, as reflected by their high degree of sequence similarity. However, in common usage and in the application, the term "homologous," when modified with an adverb such as "highly," may refer to sequence similarity and not a common evolutionary origin.

Accordingly, the term "sequence similarity" in all its grammatical forms refers to the degree of identity or correspondence between nucleic acid or amino acid sequences of proteins that may or may not share a common evolutionary origin (see Reeck et al., Cell 50:667 (1987)). In one embodiment, two DNA sequences are "substantially homologous" or "substantially similar" when at least about 50% (e.g., at least about 75%, 90%, or 95%) of the nucleotides match over the defined length of the DNA sequences. Sequences that are substantially homologous can be identified by comparing the sequences using standard software available in sequence data banks, or in a Southern hybridization experiment under, for example, stringent conditions as defined for that particular system. Defining appropriate hybridization conditions is within the skill of the art (see e.g., Sambrook et al., 1989, supra).

As used herein, "substantially similar" refers to nucleic acid fragments wherein changes in one or more nucleotide bases results in substitution of one or more amino acids, but do not affect the functional properties of the protein encoded by the DNA sequence. "Substantially similar" also refers to nucleic acid fragments wherein changes in one or more nucleotide bases do not affect the ability of the nucleic acid fragment to mediate alteration of gene expression by antisense or co-suppression technology. "Substantially similar" also refers to modifications of the nucleic acid fragments of the invention such as deletion or insertion of one or more nucleotide bases that do not substantially affect the functional properties of the resulting transcript. It is therefore understood that the invention encompasses more than the specific exemplary sequences. Each of the proposed modifications is well within the routine skill in the art, as is determination of retention of biological activity of the encoded products.

Moreover, the skilled artisan recognizes that substantially similar sequences encompassed by this invention are also defined by their ability to hybridize, under stringent conditions (0.1×SSC, 0.1% SDS, 65° C. and washed with 2×SSC, 0.1% SDS followed by 0.1×SSC, 0.1% SDS), with the sequences exemplified herein. Substantially similar nucleic acid fragments of the invention are those nucleic acid fragments whose DNA sequences are at least about 70%, 80%, 90% or 95% identical to the DNA sequence of the nucleic acid fragments reported herein.

Two amino acid sequences are "substantially homologous" or "substantially similar" when greater than about 40% of the amino acids are identical, or greater than 60% are similar (functionally identical). Preferably, the similar or homologous sequences are identified by alignment using, for example, the GCG (Genetics Computer Group, Program Manual for the GCG Package, *Version* 7, Madison, Wis.) pileup program.

The term "corresponding to" is used herein to refer to similar or homologous sequences, whether the exact position is identical or different from the molecule to which the similarity or homology is measured. A nucleic acid or amino acid sequence alignment may include spaces. Thus, the term "corresponding to" refers to the sequence similarity, and not the numbering of the amino acid residues or nucleotide bases.

A "substantial portion" of an amino acid or nucleotide sequence comprises enough of the amino acid sequence of a polypeptide or the nucleotide sequence of a gene to putatively identify that polypeptide or gene, either by manual evaluation of the sequence by one skilled in the art, or by computer-automated sequence comparison and identification using algorithms such as BLAST (Basic Local Alignment Search Tool; Altschul et al., *J. Mol. Biol.* 215:403 (1993)); available at ncbi.nlm.nih.gov/BLAST/). In general, a sequence of ten or more contiguous amino acids or thirty or more nucleotides is necessary in order to putatively identify a polypeptide or nucleic acid sequence as homologous to a known protein or gene. Moreover, with respect to nucleotide sequences, gene specific oligonucleotide probes comprising 20-30 contiguous nucleotides may be used in sequence-dependent methods of gene identification (e.g., Southern hybridization) and isolation (e.g., in situ hybridization of bacterial colonies or bacteriophage plaques). In addition, short oligonucleotides of 12-15 bases may be used as amplification primers in PCR in order to obtain a particular nucleic acid fragment comprising the primers.

Accordingly, a "substantial portion" of a nucleotide sequence comprises enough of the sequence to specifically identify and/or isolate a nucleic acid fragment comprising the sequence.

The term "percent identity," as known in the art, is a relationship between two or more polypeptide sequences or two or more polynucleotide sequences, as determined by comparing the sequences. In the art, "identity" also means the degree of sequence relatedness between polypeptide or polynucleotide sequences, as the case may be, as determined by the match between strings of such sequences. "Identity" and "similarity" can be readily calculated by known methods, including but not limited to those described in: *Computational Molecular Biology* (Lesk, A. M., ed.) Oxford University Press, New York (1988); *Biocomputing: Informatics and Genome Projects* (Smith, D. W., ed.) Academic Press, New York (1993); *Computer Analysis of Sequence Data, Part I* (Griffin, A. M., and Griffin, H. G., eds.) Humana Press, New Jersey (1994); *Sequence Analysis in Molecular Biology* (von Heinje, G., ed.) Academic Press (1987); and *Sequence Analysis Primer* (Gribskov, M. and Devereux, J., eds.) Stockton Press, New York (1991). Preferred methods to determine identity are designed to give the best match between the sequences tested. Methods to determine identity and similarity are codified in publicly available computer programs. Sequence alignments and percent identity calculations may be performed using sequence analysis software such as the Megalign program of the LASERGENE bioinformatics computing suite (DNASTAR Inc., Madison, Wis.). Multiple alignment of the sequences may be performed using the Clustal method of alignment (Higgins et al., *CABIOS*. 5:151 (1989)) with the default parameters (GAP PENALTY=10, GAP LENGTH PENALTY=10). Default parameters for pairwise alignments using the Clustal method may be selected: KTUPLE 1, GAP PENALTY=3, WINDOW=5 and DIAGONALS SAVED=5.

The term "sequence analysis software" refers to any computer algorithm or software program that is useful for the analysis of nucleotide or amino acid sequences. "Sequence analysis software" may be commercially available or independently developed. Typical sequence analysis software includes, but is not limited to, the GCG suite of programs (Wisconsin Package Version 9.0, Genetics Computer Group (GCG), Madison, Wis.), BLASTP, BLASTN, BLASTX (Altschul et al., *J. Mol. Biol.* 215:403 (1990)), and DNASTAR (DNASTAR, Inc. 1228 S. Park St. Madison, Wis. 53715 USA). Within the context of this application it will be understood that where sequence analysis software is used for analysis, that the results of the analysis will be based on the "default values" of the program referenced, unless otherwise specified. As used herein "default values" will mean any set of values or parameters which originally load with the software when first initialized.

"Chemically synthesized," as related to a sequence of DNA, means that the component nucleotides were assembled in vitro. Manual chemical synthesis of DNA may be accomplished using well-established procedures, or automated chemical synthesis can be performed using one of a number of commercially available machines. Accordingly, the genes can be tailored for optimal gene expression based on optimization of nucleotide sequence to reflect the codon bias of the host cell. The skilled artisan appreciates the likelihood of successful gene expression if codon usage is biased towards those codons favored by the host. Determination of preferred codons can be based on a survey of genes derived from the host cell where sequence information is available.

As used herein, two or more individually operable gene regulation systems are said to be "orthogonal" when; a) modulation of each of the given systems by its respective ligand, at a chosen concentration, results in a measurable change in the magnitude of expression of the gene of that system, and b) the change is statistically significantly different than the change in expression of all other systems simultaneously operable in the cell, tissue, or organism, regardless of the simultaneity or sequentially of the actual modulation. Preferably, modulation of each individually operable gene regulation system effects a change in gene expression at least 2-fold greater than all other operable systems in the cell, tissue, or organism, e.g., at least 5-fold, 10-fold, 100-fold, or 500-fold greater. Ideally, modulation of each of the given systems by its respective ligand at a chosen concentration results in a measurable change in the magnitude of expression of the gene of that system and no measurable change in expression of all other systems operable in the cell, tissue, or organism. In such cases the multiple inducible gene regulation system is said to be "fully orthogonal." Useful orthogonal ligands and orthogonal receptor-based gene expression systems are described in US 2002/0110861 A.

The term "exogenous gene" means a gene foreign to the subject, that is, a gene which is introduced into the subject through a transformation process, an unmutated version of an endogenous mutated gene or a mutated version of an endogenous unmutated gene. The method of transformation is not critical to this invention and may be any method suitable for the subject known to those in the art. Exogenous genes can be either natural or synthetic genes which are introduced into the subject in the form of DNA or RNA which may function through a DNA intermediate such as by reverse transcriptase. Such genes can be introduced into target cells, directly introduced into the subject, or indirectly introduced by the transfer of transformed cells into the subject.

The term "therapeutic product" refers to a therapeutic polypeptide or therapeutic polynucleotide which imparts a beneficial function to the host cell in which such product is expressed. Therapeutic polypeptides may include, without limitation, peptides as small as three amino acids in length, single- or multiple-chain proteins, and fusion proteins. Therapeutic polynucleotides may include, without limitation, antisense oligonucleotides, small interfering RNAs, ribozymes, and RNA external guide sequences. The therapeutic product may comprise a naturally occurring sequence, a synthetic sequence or a combination of natural and synthetic sequences.

The term "ecdysone receptor complex" generally refers to a heterodimeric protein complex having at least two members of the nuclear receptor family, ecdysone receptor ("EcR") and ultraspiracle ("USP") proteins (see Yao et al., *Nature* 366:476 (1993)); Yao et al., *Cell* 71:63 (1992)). The functional EcR complex may also include additional protein(s) such as immunophilins. Additional members of the nuclear receptor family of proteins, known as transcriptional factors (such as DHR38, betaFTZ-1 or other insect homologs), may also be ligand dependent or independent partners for EcR and/or USP. The EcR complex can also be a heterodimer of EcR protein and the vertebrate homolog of ultraspiracle protein, retinoic acid-X-receptor ("RXR") protein or a chimera of USP and RXR. The term EcR complex also encompasses homodimer complexes of the EcR protein or USP.

An EcR complex can be activated by an active ecdysteroid or non-steroidal ligand bound to one of the proteins of the complex, inclusive of EcR, but not excluding other proteins of the complex. As used herein, the term "ligand," as applied to EcR-based gene switches, describes small and soluble molecules having the capability of activating a gene switch to stimulate expression of a polypeptide encoded therein. Examples of ligands include, without limitation, an ecdysteroid, such as ecdysone, 20-hydroxyecdysone, ponasterone A, muristerone A, and the like, 9-cis-retinoic acid, synthetic analogs of retinoic acid, N,N'-diacylhydrazines such as those disclosed in U.S. Pat. Nos. 6,013,836; 5,117,057; 5,530,028; and 5,378,726 and U.S. Published Application Nos. 2005/0209283 and 2006/0020146; oxadiazolines as described in U.S. Published Application No. 2004/0171651; dibenzoylalkyl cyanohydrazines such as those disclosed in European Application No. 461,809; N-alkyl-N, N'-diaroylhydrazines such as those disclosed in U.S. Pat. No. 5,225,443; N-acyl-N-alkylcarbonylhydrazines such as those disclosed in European Application No. 234,994; N-aroyl-N-alkyl-N'-aroylhydrazines such as those described in U.S. Pat. No. 4,985,461; amidoketones such as those described in U.S. Published Application No. 2004/0049037; and other similar materials including 3,5-di-tert-butyl-4-hydroxy-N-isobutyl-benzamide, 8-O-acetylharpagide, oxysterols, 22(R) hydroxycholesterol, 24(S) hydroxycholesterol, 25-epoxycholesterol, T0901317, 5-alpha-6-alpha-epoxycholesterol-3-sulfate (ECHS), 7-ketocholesterol-3-sulfate, farnesol, bile acids, 1,1-biphosphonate esters, juvenile hormone III, and the like. Examples of diacylhydrazine ligands useful in the invention include RG-115819 (3,5-Dimethyl-benzoic acid N-(1-ethyl-2,2-dimethyl-propyl)-N'-(2-methyl-3-methoxy-benzoyl)-hydrazide), RG-115932 ((R)-3,5-Dimethyl-benzoic acid N-(1-tert-butyl-butyl)-N'-(2-ethyl-3-methoxy-benzoyl)-hydrazide), and RG-115830 (3,5-Dimethyl-benzoic acid N-(1-tert-butyl-butyl)-N'-(2-ethyl-3-methoxy-benzoyl)-hydrazide). See U.S. application Ser. No. 12/155,111, filed May 29, 2008, and PCT/US2008/006757 filed May 29, 2008, for additional diacylhydrazines that are useful in the practice of the invention.

The EcR complex includes proteins which are members of the nuclear receptor superfamily wherein all members are characterized by the presence of an amino-terminal transactivation domain ("TA"), a DNA binding domain ("DBD"), and a ligand binding domain ("LBD") separated by a hinge region. Some members of the family may also have another transactivation domain on the carboxy-terminal side of the LBD. The DBD is characterized by the presence of two cysteine zinc fingers between which are two amino acid motifs, the P-box and the D-box, which confer specificity for ecdysone response elements. These domains may be either native, modified, or chimeras of different domains of heterologous receptor proteins.

The DNA sequences making up the exogenous gene, the response element, and the EcR complex may be incorporated into archaebacteria, procaryotic cells such as *Escherichia coli, Bacillus subtilis*, or other enterobacteria, or eucaryotic cells such as plant or animal cells. However, because many of the proteins expressed by the gene are processed incorrectly in bacteria, eucaryotic cells are preferred. The cells may be in the form of single cells or multicellular organisms. The nucleotide sequences for the exogenous gene, the response element, and the receptor complex can also be incorporated as RNA molecules, preferably in the form of functional viral RNAs such as tobacco mosaic virus. Of the eucaryotic cells, vertebrate cells are preferred because they naturally lack the molecules which confer responses to the ligands of this invention for the EcR. As a result, they are "substantially insensitive" to the ligands of this invention. Thus, the ligands useful in this invention will have negligible physiological or other effects on transformed cells, or the whole organism. Therefore, cells can grow and express the desired product, substantially unaffected by the presence of the ligand itself.

EcR ligands, when used with the EcR complex which in turn is bound to the response element linked to an exogenous gene (e.g., IL-12), provide the means for external temporal regulation of expression of the exogenous gene. The order in which the various components bind to each other, that is, ligand to receptor complex and receptor complex to response element, is not critical. Typically, modulation of expression of the exogenous gene is in response to the binding of the EcR complex to a specific control, or regulatory, DNA element. The EcR protein, like other members of the nuclear receptor family, possesses at least three domains, a transactivation domain, a DNA binding domain, and a ligand binding domain. This receptor, like a subset of the nuclear receptor family, also possesses less well-defined regions responsible for heterodimerization properties. Binding of the ligand to the ligand binding domain of EcR protein, after heterodimerization with USP or RXR protein, enables the DNA binding domains of the heterodimeric proteins to bind to the response element in an activated form, thus resulting in expression or suppression of the exogenous gene. This mechanism does not exclude the potential for ligand binding to either EcR or USP, and the resulting formation of active homodimer complexes (e.g. EcR+EcR or USP+USP). In one embodiment, one or more of the receptor domains can be varied producing a chimeric gene switch. Typically, one or more of the three domains may be chosen from a source different than the source of the other domains so that the chimeric receptor is optimized in the chosen host cell or organism for transactivating activity, complementary binding of the ligand, and recognition of a specific response element. In addition, the response element itself can be modified or substituted with response elements for other DNA binding protein domains such as the GAL-4 protein from yeast (see Sadowski et al., *Nature* 335:563 (1988) or LexA protein from *E. coli* (see Brent et al., *Cell* 43:729 (1985)) to accommodate chimeric EcR complexes. Another advantage of chimeric systems is that they allow choice of a promoter used to drive the exogenous gene according to a desired end result. Such double control can be particularly important in areas of gene therapy, especially when cytotoxic proteins are produced, because both the timing of expression as well as the cells wherein expression occurs can be controlled. When exogenous genes, operatively linked to a suitable promoter, are introduced into the cells of the subject, expression of the exogenous genes is controlled by the presence of the ligand of this invention. Promoters may be constitutively or inducibly regulated or may be tissue-specific (that is, expressed only in a particular type of cell) or specific to certain developmental stages of the organism.

Numerous genomic and cDNA nucleic acid sequences coding for a variety of polypeptides, such as transcription factors and reporter proteins, are well known in the art. Those skilled in the art have access to nucleic acid sequence information for virtually all known genes and can either obtain the nucleic acid molecule directly from a public depository, the institution that published the sequence, or employ routine methods to prepare the molecule. See for example the description of the sequence accession numbers, infra.

The gene switch may be any gene switch system that regulates gene expression by addition or removal of a specific ligand. In one embodiment, the gene switch is one in which the level of gene expression is dependent on the level of ligand that is present. Examples of ligand-dependent transcription factors that may be used in the gene switches of the invention include, without limitation, members of the nuclear receptor superfamily activated by their respective ligands (e.g., glucocorticoid, estrogen, progestin, retinoid, ecdysone, and analogs and mimetics thereof) and rTTA activated by tetracycline. In one aspect of the invention, the gene switch is an EcR-based gene switch. Examples of such systems include, without limitation, the systems described in U.S. Pat. Nos. 6,258,603, 7,045,315, U.S. Published Patent Application Nos. 2006/0014711, 2007/0161086, and International Published Application No. WO 01/70816. Examples of chimeric ecdysone receptor systems are described in U.S. Pat. No. 7,091,038, U.S. Published Patent Application Nos. 2002/0110861, 2004/0033600, 2004/0096942, 2005/0266457, and 2006/0100416, and International Published Application Nos. WO 01/70816, WO 02/066612, WO 02/066613, WO 02/066614, WO 02/066615, WO 02/29075, and WO 2005/108617. An example of a non-steroidal ecdysone agonist-regulated system is the RheoSwitch® Mammalian Inducible Expression System (New England Biolabs, Ipswich, Mass.).

In one embodiment, a polynucleotide encoding the gene switch comprises a single transcription factor sequence encoding a ligand-dependent transcription factor under the control of a promoter. The transcription factor sequence may encode a ligand-dependent transcription factor that is a naturally occurring or an artificial transcription factor. An artificial transcription factor is one in which the natural sequence of the transcription factor has been altered, e.g., by mutation of the sequence or by the combining of domains from different transcription factors. In one embodiment, the transcription factor comprises a Group H nuclear receptor ligand binding domain (LBD). In one embodiment, the Group H nuclear receptor LBD is from an EcR, a ubiquitous receptor, an orphan receptor 1, a NER-1, a steroid hormone nuclear receptor 1, a retinoid X receptor interacting protein-15, a liver X receptor β, a steroid hormone receptor like protein, a liver X receptor, a liver X receptor α, a farnesoid X receptor, a receptor interacting protein 14, or a farnesol receptor. In another embodiment, the Group H nuclear receptor LBD is from an ecdysone receptor.

The EcR and the other Group H nuclear receptors are members of the nuclear receptor superfamily wherein all members are generally characterized by the presence of an amino-terminal transactivation domain (TD), a DNA binding domain (DBD), and a LBD separated from the DBD by a hinge region. As used herein, the term "DNA binding domain" comprises a minimal polypeptide sequence of a DNA binding protein, up to the entire length of a DNA binding protein, so long as the DNA binding domain functions to associate with a particular response element. Members of the nuclear receptor superfamily are also characterized by the presence of four or five domains: A/B, C, D, E, and in some members F (see U.S. Pat. No. 4,981,784 and Evans, *Science* 240:889 (1988)). The "A/B" domain corresponds to the transactivation domain, "C" corresponds to the DNA binding domain, "D" corresponds to the hinge region, and "E" corresponds to the ligand binding domain. Some members of the family may also have another transactivation domain on the carboxy-terminal side of the LBD corresponding to "F".

The DBD is characterized by the presence of two cysteine zinc fingers between which are two amino acid motifs, the P-box and the D-box, which confer specificity for response elements. These domains may be either native, modified, or chimeras of different domains of heterologous receptor proteins. The EcR, like a subset of the nuclear receptor family, also possesses less well-defined regions responsible for heterodimerization properties. Because the domains of nuclear receptors are modular in nature, the LBD, DBD, and TD may be interchanged.

In another embodiment, the transcription factor comprises a TD, a DBD that recognizes a response element associated with the exogenous gene whose expression is to be modulated; and a Group H nuclear receptor LBD. In certain embodiments, the Group H nuclear receptor LBD comprises a substitution mutation.

In other embodiments, a polynucleotide encoding the gene switch comprises a first transcription factor sequence under the control of a first promoter and a second transcription factor sequence under the control of a second promoter, wherein the proteins encoded by said first transcription factor sequence and said second transcription factor sequence interact to form a protein complex which functions as a ligand-dependent transcription factor, i.e., a "dual switch"- or "two-hybrid"-based gene switch. The first and second promoters may be the same or different.

A polynucleotide encoding a gene switch may also comprise a first transcription factor sequence and a second transcription factor sequence under the control of one promoter, wherein the proteins encoded by the first transcription factor sequence and the second transcription factor sequence interact to form a protein complex which functions as a ligand-dependent transcription factor, i.e., a "single gene switch." The first transcription factor sequence and the second transcription factor sequence may be connected by an internal ribosomal entry site, e.g., EMCV IRES.

In one embodiment, the first transcription factor sequence encodes a polypeptide comprising a TD, a DBD that recognizes a response element associated with the exogenous gene whose expression is to be modulated; and a Group H nuclear receptor LBD, and the second transcription factor sequence encodes a transcription factor comprising a nuclear receptor LBD selected from a vertebrate RXR LBD, an invertebrate RXR LBD, an ultraspiracle protein LBD, and a chimeric LBD comprising two polypeptide fragments, wherein the first polypeptide fragment is from a vertebrate RXR LBD, an invertebrate RXR LBD, or an ultraspiracle protein LBD, and the second polypeptide fragment is from a different vertebrate RXR LBD, invertebrate RXR LBD, or ultraspiracle protein LBD.

In another embodiment, the gene switch comprises a first transcription factor sequence encoding a first polypeptide comprising a nuclear receptor LBD and a DBD that recognizes a response element associated with the exogenous gene whose expression is to be modulated, and a second transcription factor sequence encoding a second polypeptide comprising a TD and a nuclear receptor LBD, wherein one of the nuclear receptor LBDs is a Group H nuclear receptor LBD. In a preferred embodiment, the first polypeptide is substantially free of a TD and the second polypeptide is substantially free of a DBD. For purposes of the invention, "substantially free" means that the protein in question does not contain a sufficient sequence of the domain in question to provide activation or binding activity.

In another aspect of the invention, the first transcription factor sequence encodes a protein comprising a heterodimer partner and a TD and the second transcription factor sequence encodes a protein comprising a DBD and a LBD.

When only one nuclear receptor LBD is a Group H LBD, the other nuclear receptor LBD may be from any other nuclear receptor that forms a dimer with the Group H LBD. For example, when the Group H nuclear receptor LBD is an EcR LBD, the other nuclear receptor LBD "partner" may be from an EcR, a vertebrate RXR, an invertebrate RXR, an ultraspiracle protein (USP), or a chimeric nuclear receptor comprising at least two different nuclear receptor LBD polypeptide fragments selected from a vertebrate RXR, an invertebrate RXR, and a USP (see WO 01/70816 A2, International Patent Application No. PCT/US02/05235 and US 2004/0096942 A1. The "partner" nuclear receptor ligand binding domain may further comprise a truncation mutation, a deletion mutation, a substitution mutation, or another modification.

In one embodiment, the vertebrate RXR LBD is from a human *Homo sapiens*, mouse *Mus musculus*, rat *Rattus norvegicus*, chicken *Gallus gallas*, pig *Sus scrofa* domestica, frog *Xenopus laevis*, zebrafish *Danio rerio*, tunicate *Polyandrocarpa misakiensis*, or jellyfish *Tripedalia cysophora* RXR.

In one embodiment, the invertebrate RXR ligand binding domain is from a locust *Locusta migratoria* ultraspiracle polypeptide ("LmUSP"), an ixodid tick *Amblyomma americanum* RXR homolog 1 ("AmaRXR1"), an ixodid tick *Amblyomma americanum* RXR homolog 2 ("AmaRXR2"), a fiddler crab *Celuca pugilator* RXR homolog ("CpRXR"), a beetle *Tenebrio molitor* RXR homolog ("TmRXR"), a honeybee *Apis mellifera* RXR homolog ("AmRXR"), an aphid *Myzus persicae* RXR homolog ("MpRXR"), or a non-Dipteran/non-Lepidopteran RXR homolog.

In one embodiment, the chimeric RXR LBD comprises at least two polypeptide fragments selected from a vertebrate species RXR polypeptide fragment, an invertebrate species RXR polypeptide fragment, and a non-Dipteran/non-Lepidopteran invertebrate species RXR homolog polypeptide fragment. A chimeric RXR ligand binding domain for use in the invention may comprise at least two different species RXR polypeptide fragments, or when the species is the same, the two or more polypeptide fragments may be from two or more different isoforms of the species RXR polypeptide fragment.

In one embodiment, the chimeric RXR ligand binding domain comprises at least one vertebrate species RXR polypeptide fragment and one invertebrate species RXR polypeptide fragment.

In another embodiment, the chimeric RXR ligand binding domain comprises at least one vertebrate species RXR polypeptide fragment and one non-Dipteran/non-Lepidopteran invertebrate species RXR homolog polypeptide fragment.

The ligand, when combined with the LBD of the nuclear receptor(s), which in turn are bound to the response element linked to the exogenous gene, provides external temporal regulation of expression of the exogenous gene. The binding mechanism or the order in which the various components of this invention bind to each other, that is, for example, ligand to LBD, DBD to response element, TD to promoter, etc., is not critical.

In a specific example, binding of the ligand to the LBD of a Group H nuclear receptor and its nuclear receptor LBD partner enables expression of the exogenous gene. This mechanism does not exclude the potential for ligand binding to the Group H nuclear receptor (GHNR) or its partner, and the resulting formation of active homodimer complexes (e.g. GHNR+GHNR or partner+partner). Preferably, one or more of the receptor domains is varied producing a hybrid gene switch. Typically, one or more of the three domains, DBD, LBD, and TD, may be chosen from a source different than the source of the other domains so that the hybrid genes and the resulting hybrid proteins are optimized in the chosen host cell or organism for transactivating activity, complementary binding of the ligand, and recognition of a specific response element. In addition, the response element itself can be modified or substituted with response elements for other DNA binding protein domains such as the GAL-4 protein from yeast (see Sadowski et al., *Nature* 335:563 (1988)) or LexA protein from *Escherichia coli* (see Brent et al., *Cell* 43:729 (1985)), or synthetic response elements specific for targeted interactions with proteins designed, modified, and selected for such specific interactions (see, for example, Kim et al., *Proc. Natl. Acad. Sci. USA*, 94:3616 (1997)) to accommodate hybrid receptors.

The functional EcR complex may also include additional protein(s) such as immunophilins. Additional members of the nuclear receptor family of proteins, known as transcriptional factors (such as DHR38 or betaFTZ-1), may also be ligand dependent or independent partners for EcR, USP, and/or RXR. Additionally, other cofactors may be required such as proteins generally known as coactivators (also termed adapters or mediators). These proteins do not bind sequence-specifically to DNA and are not involved in basal transcription. They may exert their effect on transcription activation through various mechanisms, including stimulation of DNA-binding of activators, by affecting chromatin structure, or by mediating activator-initiation complex interactions. Examples of such coactivators include RIP140, TIF1, RAP46/Bag-1, ARA70, SRC-1/NCoA-1, TIF2/GRIP/NCoA-2, ACTR/A1B1/RAC3/pCIP as well as the promiscuous coactivator C response element B binding protein, CBP/p300 (for review see Glass et al., *Curr. Opin. Cell Biol.* 9:222 (1997)). Also, protein cofactors generally known as corepressors (also known as repressors, silencers, or silencing mediators) may be required to effectively inhibit transcriptional activation in the absence of ligand. These corepressors may interact with the unliganded EcR to silence the activity at the response element. Current evidence suggests that the binding of ligand changes the conformation of the receptor, which results in release of the corepressor and recruitment of the above described coactivators, thereby abolishing their silencing activity. Examples of corepressors include N-CoR and SMRT (for review, see Horwitz et al., *Mol Endocrinol.* 10:1167 (1996)). These cofactors may either be endogenous within the cell or organism, or may be added exogenously as transgenes to be expressed in either a regulated or unregulated fashion.

The exogenous gene is operably linked to a promoter comprising at least one response element that is recognized by the DBD of the ligand-dependent transcription factor encoded by the gene switch. In one embodiment, the promoter comprises 1, 2, 3, 4, 5, 6, 7, 8, 9, 10, or more copies of the response element. Promoters comprising the desired response elements may be naturally occurring promoters or artificial promoters created using techniques that are well known in the art, e.g., one or more response elements operably linked to a minimal promoter.

To introduce the polynucleotides into the cells, a vector can be used. The vector may be, for example, a plasmid vector or a single- or double-stranded RNA or DNA viral vector. Such vectors may be introduced into cells by well-known techniques for introducing DNA and RNA into cells. Viral vectors may be replication competent or replication defective. In the latter case, viral propagation generally will occur only in complementing host cells. As used herein, the term "host cell" or "host" is used to mean a cell of the invention that is harboring one or more polynucleotides of the invention.

Thus, at a minimum, the vectors must include the polynucleotides of the invention. Other components of the vector may include, but are not limited to, selectable markers, chromatin modification domains, additional promoters driving expression of other polypeptides that may also be present on the vector (e.g., a lethal polypeptide), genomic integration sites, recombination sites, and molecular insertion pivots. The vectors may comprise any number of these additional elements, either within or not within the polynucleotides, such that the vector can be tailored to the specific goals of the therapeutic methods desired.

In one embodiment of the invention, the vectors that are introduced into the cells further comprise a "selectable marker gene" which, when expressed, indicates that the gene switch construct of the invention has been integrated into the genome of the host cell. In this manner, the selector gene can be a positive marker for the genome integration. While not critical to the methods of the invention, the presence of a selectable marker gene allows the practitioner to select for a population of live cells where the vector construct has been integrated into the genome of the cells. Thus, certain embodiments of the invention comprise selecting cells where the vector has successfully been integrated. As used herein, the term "select" or variations thereof, when used in conjunction with cells, is intended to mean standard, well-known methods for choosing cells with a specific genetic make-up or phenotype. Typical methods include, but are not limited to, culturing cells in the presence of antibiotics, such as G418, neomycin and ampicillin. Other examples of selectable marker genes include, but are not limited to, genes that confer resistance to dihydrofolate reductase, hygromycin, or mycophenolic acid. Other methods of selection include, but are not limited to, a selectable marker gene that allows for the use of thymidine kinase, hypoxanthine-guanine phosphoribosyltransferase or adenine phosphoribosyltransferase as selection agents. Cells comprising a vector construct comprising an antibiotic resistance gene or genes would then be capable of tolerating the antibiotic in culture. Likewise, cells not comprising a vector construct comprising an antibiotic resistance gene or genes would not be capable of tolerating the antibiotic in culture.

As used herein, a "chromatin modification domain" (CMD) refers to nucleotide sequences that interact with a variety of proteins associated with maintaining and/or altering chromatin structure, such as, but not limited to, DNA insulators. See Ciavatta et al., *Proc. Nat'l Acad. Sci. U.S.A.*, 103:9958 (2006). Examples of CMDs include, but are not limited to, the chicken β-globulin insulator and the chicken hypersensitive site 4 (cHS4). The use of different CMD sequences between one or more gene programs (i.e., a promoter, coding sequence, and 3' regulatory region), for example, can facilitate the use of the differential CMD DNA sequences as "mini homology arms" in combination with various microorganism or in vitro recombineering technologies to "swap" gene programs between existing multigenic and monogenic shuttle vectors. Other examples of chromatin modification domains are known in the art or can be readily identified.

Particular vectors for use with the invention are expression vectors that code for proteins or polynucleotides. Generally, such vectors comprise cis-acting control regions effective for expression in a host operatively linked to the polynucleotide to be expressed. Appropriate trans-acting factors are supplied by the host, supplied by a complementing vector or supplied by the vector itself upon introduction into the host.

A great variety of expression vectors can be used to express proteins or polynucleotides. Such vectors include chromosomal, episomal and virus-derived vectors, e.g., vectors derived from bacterial plasmids, from bacteriophage, from yeast episomes, from yeast chromosomal elements, from viruses such as adeno-associated viruses, lentiviruses, baculoviruses, papova viruses, such as SV40, vaccinia viruses, adenoviruses, fowl pox viruses, pseudorabies viruses and retroviruses, and vectors derived from combinations thereof, such as those derived from plasmid and bacteriophage genetic elements, such as cosmids and phagemids. All may be used for expression in accordance with this aspect of the invention. Generally, any vector suitable to maintain, propagate or express polynucleotides or proteins in a host may be used for expression in this regard.

The polynucleotide sequence in the expression vector is operatively linked to appropriate expression control sequence(s) including, for instance, a promoter to direct mRNA transcription. Representatives of additional promoters include, but are not limited to, constitutive promoters and tissue specific or inducible promoters. Examples of constitutive eukaryotic promoters include, but are not limited to, the promoter of the mouse metallothionein I gene (Hamer et al., *J. Mol. Appl. Gen.* 1:273 (1982)); the TK promoter of Herpes virus (McKnight, *Cell* 31:355 (1982)); the SV40 early promoter (Benoist et al., *Nature* 290:304 (1981)); and the vaccinia virus promoter. Additional examples of the promoters that could be used to drive expression of a protein or polynucleotide include, but are not limited to, tissue-specific promoters and other endogenous promoters for specific proteins, such as the albumin promoter (hepatocytes), a proinsulin promoter (pancreatic beta cells) and the like. In general, expression constructs will contain sites for transcription, initiation and termination and, in the transcribed region, a ribosome binding site for translation. The coding portion of the mature transcripts expressed by the constructs may include a translation initiating AUG at the beginning and a termination codon (UAA, UGA or UAG) appropriately positioned at the end of the polypeptide to be translated.

In addition, the constructs may contain control regions that regulate, as well as engender expression. Generally, such regions will operate by controlling transcription, such as repressor binding sites and enhancers, among others.

Examples of eukaryotic vectors include, but are not limited to, pW-LNEO, pSV2CAT, pOG44, pXT1 and pSG available from Stratagene; pSVK3, pBPV, pMSG and pSVL available from Amersham Pharmacia Biotech; and pCM-VDsRed2-express, pIRES2-DsRed2, pDsRed2-Mito, and pCMV-EGFP available from Clontech. Many other vectors are well-known and commercially available.

Particularly useful vectors, which comprise molecular insertion pivots for rapid insertion and removal of elements of gene programs, are described in United States Published Patent Application No. 2004/0185556, U.S. patent application Ser. No. 11/233,246 and International Published Application Nos. WO 2005/040336 and WO 2005/116231. An example of such vectors is the UltraVector™ Production System (Intrexon Corp., Blacksburg, Va.), as described in WO 2007/038276. As used herein, a "gene program" is a combination of genetic elements comprising a promoter (P), an expression sequence (E) and a 3' regulatory sequence (3), such that "PE3" is a gene program. The elements within the gene program can be easily swapped between molecular pivots that flank each of the elements of the gene program. A molecular pivot, as used herein, is defined as a polynucleotide comprising at least two non-variable rare or uncommon restriction sites arranged in a linear fashion. In one embodiment, the molecular pivot comprises at least three non-variable rare or uncommon restriction sites arranged in a linear fashion. Typically any one molecular pivot would not include a rare or uncommon restriction site of any other molecular pivot within the same gene program. Cognate sequences of greater than 6 nucleotides upon which a given restriction enzyme acts are referred to as "rare" restriction sites. There are, however, restriction sites of 6 bp that occur more infrequently than would be statistically predicted, and these sites and the endonucleases that cleave them are referred to as "uncommon" restriction sites. Examples of either rare or uncommon restriction enzymes include, but are not limited to, AsiS I, Pac I, Sbf I, Fse I, Asc I, Mlu I, SnaB I, Not I, Sal I, Swa I, Rsr II, BSiW I, Sfo I, Sgr AI, AflIII, Pvu I, Ngo MW, Ase I, Flp I, Pme I, Sda I, Sgf I, Srf I, and Sse8781 I.

The vector may also comprise restriction sites for a second class of restriction enzymes called homing endonuclease (HE) enzymes. HE enzymes have large, asymmetric restriction sites (12-40 base pairs), and their restriction sites are infrequent in nature. For example, the HE known as I-SceI has an 18 bp restriction site (5TAGGGATAACA-GGGTAAT3' (SEQ ID NO:12)), predicted to occur only once in every 7×10$^{10}$ base pairs of random sequence. This rate of occurrence is equivalent to only one site in a genome that is 20 times the size of a mammalian genome. The rare nature of HE sites greatly increases the likelihood that a genetic engineer can cut a gene program without disrupting the integrity of the gene program if HE sites were included in appropriate locations in a cloning vector plasmid.

Selection of appropriate vectors and promoters for expression in a host cell is a well-known procedure, and the requisite techniques for vector construction and introduction into the host, as well as its expression in the host are routine skills in the art.

The introduction of the polynucleotides into the cells can be a transient transfection, stable transfection, or can be a locus-specific insertion of the vector. Transient and stable transfection of the vectors into the host cell can be effected by calcium phosphate transfection, DEAE-dextran mediated transfection, cationic lipid-mediated transfection, electroporation, transduction, infection, or other methods. Such methods are described in many standard laboratory manuals, such as Davis et al., Basic Methods in Molecular Biology (1986); Keown et al., 1990, Methods Enzymol. 185: 527-37; Sambrook et al., 2001, Molecular Cloning, A Laboratory Manual, Third Edition, Cold Spring Harbor Laboratory Press, N.Y. These stable transfection methods result in random insertion of the vector into the genome of the cell. Further, the copy number and orientation of the vectors are also, generally speaking, random.

In one embodiment of the invention, the vector is inserted into a bio-neutral site in the genome. A bio-neutral site is a site in the genome where insertion of the polynucleotides interferes very little, if any, with the normal function of the cell. Bio-neutral sites may be analyzed using available bioinformatics. Many bio-neutral sites are known in the art, e.g., the ROSA-equivalent locus. Other bio-neutral sites may be identified using routine techniques well known in the art. Characterization of the genomic insertion site(s) is performed using methods known in the art. To control the location, copy number and/or orientation of the polynucleotides when introducing the vector into the cells, methods of locus-specific insertion may be used. Methods of locus-specific insertion are well-known in the art and include, but are not limited to, homologous recombination and recombinase-mediated genome insertion. Of course, if locus-specific insertion methods are to be used in the methods of the invention, the vectors may comprise elements that aid in this locus-specific insertion, such as, but not limited to, homologous recombination. For example, the vectors may comprise one, two, three, four or more genomic integration sites (GISs). As used herein, a "genomic integration site" is defined as a portion of the vector sequence which nucleotide sequence is identical or nearly identical to portions of the genome within the cells that allows for insertion of the vector in the genome. In particular, the vector may comprise two genomic insertion sites that flank at least the polynucleotides. Of course, the GISs may flank additional elements, or even all elements present on the vector.

In another embodiment, locus-specific insertion may be carried out by recombinase-site specific gene insertion. Briefly, bacterial recombinase enzymes, such as, but not limited to, PhiC31 integrase can act on "pseudo" recombination sites within the human genome. These pseudo recombination sites can be targets for locus-specific insertion using the recombinases. Recombinase-site specific gene insertion is described in Thyagarajan et al., *Mol. Cell Biol.* 21:3926 (2001). Other examples of recombinases and their respective sites that may be used for recombinase-site specific gene insertion include, but are not limited to, serine recombinases such as R4 and TP901-1 and recombinases described in WO 2006/083253.

In a further embodiment, the vector may comprise a chemo-resistance gene, e.g., the multidrug resistance gene mdr1, dihydrofolate reductase, or O$^6$-alkylguanine-DNA alkyltransferase. The chemo-resistance gene may be under the control of a constitutive (e.g., CMV) or inducible (e.g., RheoSwitch®) promoter. In this embodiment, if it is desired to treat a disease in a subject while maintaining the modified cells within the subject, a clinician may apply a chemotherapeutic agent to destroy diseased cells while the modified cells would be protected from the agent due to expression of a suitable chemo-resistance gene and may continue to be used for treatment, amelioration, or prevention of a disease or disorder. By placing the chemo-resistance gene under an inducible promoter, the unnecessary expression of the chemo-resistance gene can be avoided, yet it will still be available in case continued treatment is needed. If the modified cells themselves become diseased, they could still be destroyed by inducing expression of a lethal polypeptide as described below.

The methods of the invention are carried out by introducing the polynucleotides encoding the gene switch and the exogenous gene into cells of a subject. Any method known for introducing a polynucleotide into a cell known in the art, such as those described above, can be used.

When the polynucleotides are to be introduced into cells ex vivo, the cells may be obtained from a subject by any technique known in the art, including, but not limited to, biopsies, scrapings, and surgical tissue removal. The isolated cells may be cultured for a sufficient amount of time to allow the polynucleotides to be introduced into the cells, e.g., 2, 4, 6, 8, 10, 12, 18, 24, 36, 48, hours or more. Methods for culturing primary cells for short periods of time are well known in the art. For example, cells may be cultured in plates (e.g., in microwell plates) either attached or in suspension.

For ex vivo therapeutic methods, cells are isolated from a subject and cultured under conditions suitable for introducing the polynucleotides into the cells. Once the polynucleotides have been introduced into the cells, the cells are incubated for a sufficient period of time to allow the ligand-dependent transcription factor to be expressed, e.g., 0.5, 1, 2, 3, 4, 5, 6, 7, 8, 9, 10, 12, 18, or 24 hours or more. At some point after the introduction of the polynucleotides into the cells (either before or after significant levels of the ligand-dependent transcription factor is expressed), the cells are introduced back into the subject. Reintroduction may be carried out by any method known in the art, e.g., intravenous infusion or direct injection into a tissue or cavity. In one embodiment, the presence of the polynucleotides in the cells is determined prior to introducing the cells back into the subject. In another embodiment, cells containing the polynucleotides are selected (e.g., based on the presence of a selectable marker in the polynucleotides) and only those cells containing the polynucleotides are reintroduced into the subject. After the cells are reintroduced to the subject, ligand is administered to the subject to induce expression of the therapeutic polypeptide or therapeutic polynucleotide. In an alternative embodiment, the ligand may be added to the cells even before the cells are reintroduced to the subject such that the therapeutic polypeptide or therapeutic polynucleotide is expressed prior to reintroduction of the cells. The ligand may be administered by any suitable method, either systemically (e.g., orally, intravenously) or locally (e.g., intraperitoneally, intrathecally, intraventricularly, direct injection into the tissue or organ where the cells were reintroduced, for example, intratumorally). The optimal timing of ligand administration can be determined for each type of cell and disease or disorder using only routine techniques.

The in vivo therapeutic methods of the invention involve direct in vivo introduction of the polynucleotides into the cells of the subject. The polynucleotides may be introduced into the subject systemically or locally (e.g., at the site of the disease or disorder). Once the polynucleotides have been introduced to the subject, the ligand may be administered to induce expression of the therapeutic polypeptide or therapeutic polynucleotide. The ligand may be administered by any suitable method, either systemically (e.g., orally, intravenously) or locally (e.g., intraperitoneally, intrathecally, intraventricularly, or direct injection into the tissue or organ where the disease or disorder is occurring, for example, intratumorally). The optimal timing of ligand administration can be determined for each type of cell and disease or disorder using only routine techniques.

For in vivo use, the ligands described herein may be taken up in pharmaceutically acceptable carriers, such as, for example, solutions, suspensions, tablets, capsules, ointments, elixirs, and injectable compositions. Pharmaceutical compositions may contain from 0.01% to 99% by weight of the ligand. Compositions may be either in single or multiple dose forms. The amount of ligand in any particular pharmaceutical composition will depend upon the effective dose, that is, the dose required to elicit the desired gene expression or suppression.

Suitable routes of administering the pharmaceutical preparations include oral, rectal, topical (including dermal, buccal and sublingual), vaginal, parenteral (including subcutaneous, intramuscular, intravenous, intradermal, intrathecal, intratumoral, and epidural) and by naso-gastric tube. It will be understood by those skilled in the art that the preferred route of administration will depend upon the condition being treated and may vary with factors such as the condition of the recipient.

As used herein, the term "rAD.RheoIL12" refers to an adenoviral polynucleotide vector harboring the IL-12 gene under the control of a gene switch of the RheoSwitch® Therapeutic System (RTS), which is capable of producing IL-12 protein in the presence of activating ligand.

As used herein, the term "IL-12p70" refers to IL-12 protein, which naturally has two subunits commonly referred to as p40 and p35. The term IL-12p70 encompasses fusion proteins comprising the two subunits of IL-12 (p40 and p35), wherein the fusion protein may include linker amino acids between subunits.

As used herein, the term "a protein having the function of IL-12" refers to a protein that has at least 20% (e.g., at least 30%, 40%, 50%, 60%, 70%, 80%, 90%, 95%, 99%, or 100%) of any bioactivity of human IL-12. The bioactivities of IL-12 are well known in the art and include, without limitation, differentiation of naive T cells into Th1 cells, stimulation of the growth and function of T cells, production of interferon-gamma (IFN-γ) and tumor necrosis factor-alpha (TNF-α) from T and natural killer (NK) cells, reduction of IL-4 mediated suppression of IFN-γ, enhancement of the cytotoxic activity of NK cells and $CD8^+$ cytotoxic T lymphocytes, stimulation of the expression of IL-12R-131 and IL-12R-132, and anti-angiogenic activity. The term "a protein having the function of IL-12" encompasses mutants of a wild type IL-12 sequence, wherein the wild type sequence has been altering by one or more of addition, deletion, or substitution of amino acids, as well as non-IL-12 proteins that mimic one or more of the bioactivities of IL-12.

As used herein, the term "rAd.cIL12" refers to an adenoviral polynucleotide control vector containing the IL-12 gene under the control of a constitutive promoter.

As used herein, the terms "activating" or "activate" refer to any measurable increase in cellular activity of a gene switch, resulting in expression of a gene of interest (e.g., IL-12 protein).

As used herein, the terms "treating" or "treatment" of a disease refer to executing a protocol, which may include administering one or more drugs or in vitro engineered cells to a mammal (human or non-human), in an effort to alleviate signs or symptoms of the disease. Thus, "treating" or "treatment" should not necessarily be construed to require complete alleviation of signs or symptoms, does not require a cure, and specifically includes protocols that have only marginal effect on the subject.

As used herein, "immune cells" include dendritic cells, macrophages, neutrophils, mast cells, eosinophils, basophils, natural killer cells and lymphocytes (e.g., B and T cells).

As used herein, the terms "dendritic cells" and "DC" are interchangeably used.

As used herein, the term "therapy support cells" (TSC) are cells that can be modified (e.g., transfected) with the vector of the invention to deliver the one or more proteins having the function of an immunomodulator and, optionally, a protein having the function of IL-12, to tumor microenvironments. Such TSC include, but are not limited to, stem cells, fibroblasts, endothelial cells and keratinocytes.

As used herein, the terms "in vitro engineered dendritic cells" or "in vitro engineered population of dendritic cells" or "in vitro engineered DC" or "a population of engineered dendritic cells" or "DC expressing IL-12" or "DC.RheoIL12" refer to dendritic cells conditionally expressing IL-12 under the control of a gene switch, which can be activated by activating ligand.

As used herein, the terms "in vitro engineered TSC" or "in vitro engineered population of TSC" or "a population of engineered TSC" or "TSC expressing an immunomodulator" or "TSC expressing IL-12" refer to therapy support cells, e.g., stem cells, fibroblasts, endothelial cells and keratinocytes, conditionally expressing an immunomodulator and/or IL-12 as the case may be under the control of a gene switch, which can be activated by activating ligand.

As used herein, the terms "MOI" or "Multiplicity of Infection" refer to the average number of adenovirus particles that infect a single cell in a specific experiment (e.g., recombinant adenovirus or control adenovirus)

As used herein, the term "tumor" refers to all benign or malignant cell growth and proliferation either in vivo or in vitro, whether precancerous or cancerous cells and/or tissues.

Examples of cancers that can be treated according to the invention include breast cancer, prostate cancer, lymphoma, skin cancer, pancreatic cancer, colon cancer, melanoma, malignant melanoma, ovarian cancer, brain cancer, primary brain carcinoma, head-neck cancer, glioma, glioblastoma, liver cancer, bladder cancer, non-small cell lung cancer, head or neck carcinoma, breast carcinoma, ovarian carcinoma, lung carcinoma, small-cell lung carcinoma, Wilms' tumor, cervical carcinoma, testicular carcinoma, bladder carcinoma, pancreatic carcinoma, stomach carcinoma, colon carcinoma, prostatic carcinoma, genitourinary carcinoma, thyroid carcinoma, esophageal carcinoma, myeloma, multiple myeloma, adrenal carcinoma, renal cell carcinoma, endometrial carcinoma, adrenal cortex carcinoma, malignant pancreatic insulinoma, malignant carcinoid carcinoma, choriocarcinoma, mycosis fungoides, malignant hypercalcemia, cervical hyperplasia, leukemia, acute lymphocytic leukemia, chronic lymphocytic leukemia, acute myelogenous leukemia, chronic myelogenous leukemia, chronic granulocytic leukemia, acute granulocytic leukemia, hairy cell leukemia, neuroblastoma, rhabdomyosarcoma, Kaposi's sarcoma, polycythemia vera, essential thrombocytosis, Hodgkin's disease, non-Hodgkin's lymphoma, soft-tissue sarcoma, osteogenic sarcoma, primary macroglobulinemia, and retinoblastoma, and the like.

The invention provides engineering of DC to conditionally express a protein having the function of IL-12 and therapeutic uses and/or applications for the treatment of cancer or tumors or both. In vitro engineered DC that conditionally express a protein having the function of IL-12 are a safe improvement over constitutive production of IL-12 protein. Additionally, the ability to control the timing and level of IL-12 expression provides improved control of the efficacy of the treatment. Therefore, in vitro engineered DC may be formulated into pharmaceutical compositions as therapeutics for the treatment of a cancer or a tumor in a human or a non-human organism. Alternatively, in vitro engineered populations of DC or subsets thereof may be used as vehicles to conditionally deliver IL-12 protein production to a specific area (normal tissue, cancer, or tumor) in the body of a human or non-human organism. The engineered dendritic cells may also conditionally express IFN-alpha. The dendritic cells utilized may be autologous or non-autologous dendritic cells. The dendritic cells may be isolated from bone marrow or from peripheral blood circulation. In human patients, dendritic cell populations may be isolated via a leukophoresis procedure, where a white blood cell fraction is isolated and removed and other blood components are re-infused to the patient.

The invention also provides engineering of immune cells other than DC such as macrophages, neutrophils, mast cells, eosinophils, basophils, natural killer cells, and lymphocytes (e.g., B and T cells) to conditionally express a protein having the function of IL-12 and therapeutic uses and/or applications for the treatment of cancer or tumors or both. In vitro engineered immune cells other than DC, e.g., macrophages, neutrophils, mast cells, eosinophils, basophils, natural killer cells, and lymphocytes (e.g., B and T cells) that conditionally express a protein having the function of IL-12 are a safe improvement over constitutive production of IL-12 protein. Additionally, the ability to control the timing and level of IL-12 expression provides improved control of the efficacy of the treatment. Therefore, in vitro engineered immune cells other than DC, e.g., macrophages, neutrophils, mast cells, eosinophils, basophils, natural killer cells, and lymphocytes (e.g., B and T cells) may be formulated into pharmaceutical compositions as therapeutics for the treatment of a cancer or a tumor in a human or a non-human organism. Alternatively, in vitro engineered populations of immune cells other than DC, e.g., macrophages, neutrophils, mast cells, eosinophils, basophils, natural killer cells, and lymphocytes (e.g., B and T cells) or subsets thereof may be used as vehicles to conditionally deliver IL-12 protein production to a specific area (normal tissue, cancer, or tumor) in the body of a human or non-human organism. The engineered immune cells other than DC, e.g., macrophages, neutrophils, mast cells, eosinophils, basophils, natural killer cells, and lymphocytes (e.g., B and T cells) may also conditionally express IFN-alpha. The immune cells utilized may be autologous or non-autologous immune cells. The immune cells may be isolated from bone marrow or from peripheral blood circulation. In human patients, immune cell populations may be isolated via a leukophoresis procedure, where a white blood cell fraction is isolated and removed and other blood components are re-infused to the patient.

In another embodiment, the dendritic cells may be prepared by transfecting human hematopoietic stem cells with a vector of the invention expressing a protein having the function of IL-12, and differentiating the transfected stem cell to give a dendritic cell. See U.S. Pat. No. 6,734,014.

In one embodiment, a nucleic acid adenoviral vector (rAd.RheoIL12) containing a gene switch, wherein the coding sequences for VP 16-RXR and Gal4-EcR are separated by the EMCV internal ribosome entry site (IRES) sequence are inserted into the adenoviral shuttle vector under the control of the human ubiquitin C promoter. The coding sequences for the p40 and p35 subunits of IL12 separated by an IRES sequence, and placed under the control of a synthetic inducible promoter, are inserted upstream of the ubiquitin C promoter.

In another embodiment, the invention provides a shuttle vector carrying transcription units (VP16-RXR and Gal4-EcR) for the two fusion proteins and inducible IL-12 subunits recombined with the adenoviral backbone (AdEasy1) in *E. coli* BJ5183 cells. After verifying the recombinant clone, the plasmid carrying the rAd.RheoIL12 genome is grown in and purified from XL10-Gold cells, digested off the plasmid backbone and packaged by transfection into HEK 293 cells.

In a particular embodiment, the resulting primary viral stock is amplified by re-infection of HEK 293 cells and is purified by CsCl density-gradient centrifugation.

In one embodiment the IL-12 gene is a wild-type IL-12 gene sequence. In another embodiment, the IL-12 gene is a modified gene sequence, e.g., a chimeric sequence or a sequence that has been modified to use preferred codons.

In one embodiment, the IL-12 gene is the human wild type IL-12 sequence. In another embodiment, the sequence is at least 85% identical to wild type human IL-12 sequence, e.g., at least 90%, 95%, or 99% identical to wild type human IL-12. In a further embodiment, the IL-12 gene sequence encodes the human IL-12 polypeptide. In another embodiment, the gene encodes a polypeptide that is at least 85% identical to wild type human IL-12 e.g., at least 90%, 95%, or 99% identical to wild type human IL-12.

In one embodiment, the IL-12 gene is the wild type mouse IL-12 sequence. In another embodiment, the sequence is at least 85% identical to wild type mouse IL-12, e.g., at least 90%, 95%, or 99% identical to wild type mouse IL-12. In a further embodiment, the IL-12 gene sequence encodes the mouse IL-12 polypeptide. In another embodiment, the gene encodes a polypeptide that is at least 85% identical to wild type mouse IL-12, e.g., at least 90%, 95%, or 99% identical to wild type mouse IL-12.

The invention provides a method for producing a population of in vitro engineered DC conditionally expressing a protein having the function of IL-12, the method comprising the steps of (a) modifying at least a portion of DC, e.g., bone-marrow derived DC, by introducing into said DC a vector harboring a gene switch comprising a nucleic acid sequence encoding a protein having the function of IL-12, thereby producing said population of in vitro engineered DC that are capable of treating or preventing a disease.

In another embodiment, the invention provides a method for producing a population of in vitro engineered immune cells other than DC, e.g., macrophages, neutrophils, mast cells, eosinophils, basophils, natural killer cells and lymphocytes (e.g., B and T cells) or TSC conditionally expressing a protein having the function of IL-12, the method comprising the steps of: (a) modifying at least a portion of the immune cells other than DC or TSC by introducing into said immune cells other than DC or TSC a vector harboring a gene switch comprising a nucleic acid sequence encoding a protein having the function of IL-12, thereby producing said population of in vitro engineered immune cells other than DC or TSC that are capable of treating or preventing a disease.

In other embodiments, the invention provides isolation and enrichment of DC, immune cells other than DC or TSC. DC may be isolated from bone marrow from humans, mice, or other mammals. The dendritic cells may be isolated from the blood of humans, mice or other mammals. In human patients, dendritic cell populations may be isolated via a leukophoresis procedure as is known in the art, where a white blood cell fraction is isolated and removed and other blood components are re-infused to the patient. In one embodiment, DC are derived from murine bone marrow as previously described (Tatsumi et al., 2003). Briefly, wild-type or EGFP Tg mouse bone marrow (BM) is cultured in conditioned medium (CM) supplemented with 1000 units/ml recombinant murine granulocyte/macrophage colony-stimulating factor and recombinant mIL-4 (Peprotech, Rocky Hill, N.J.) at 37° C. in a humidified, 5% $CO_2$ incubator for 7 days. $CD11c^+$ DC are then isolated, e.g., using specific MACSTM beads, per the manufacturer's instructions (Miltenyi Biotec, Auburn, Calif.). $CD11c^+$ DC produced in this manner were >95% pure based on morphology and co-expression of the CD11b, CD40, CD80, and class I and class II MHC antigens.

One embodiment of the invention provides engineered DC conditionally expressing a protein having the function of IL-12 suitable for therapeutic applications for the treatment of cancer, or tumors or both as gene therapy in human or non-human organism. In another embodiment of the invention provides engineered DC conditionally expressing a protein having the function of IL-12 and/or a protein having the function of IFN-alpha suitable for therapeutic applications for the treatment of cancer, or tumors or both as gene therapy in human or non-human organism.

In an embodiment, the invention provides engineered DC containing a gene switch.

In another embodiment, the invention encompasses method of treating tumors in a mammal comprising administering an effective amount of a diacylhydrazine ligand.

In another embodiment, the invention encompasses method of treating tumors in a mammal comprising administering an effective amount of RG-115830 or RG-115932.

In another embodiment, the invention encompasses kits comprising dendritic cells engineered to contain a gene switch and comprising a ligand that activates the gene switch.

In another embodiment, the invention encompasses kits comprising dendritic cells engineered to contain a gene switch and comprising a composition containing RG-115830 or RG-115932.

In another embodiment, the invention provides engineered DC, immune cells other than DC, or TSC containing at least a portion of an ecdysone receptor. In another embodiment, the invention provides engineered DC, immune cells other than DC, or TSC containing an ecdysone receptor-based gene switch. In another embodiment, the invention provides engineered DC, immune cells other than DC, or TSC containing RheoSwitch. In another embodiment, the invention provides a kit comprising engineered DC, immune cells other than DC, or TSC containing a gene switch and a ligand that modulates the gene switch. In another embodiment, the kits further comprise a diacylhydrazine ligand. In another embodiment, the kit further comprises RG-115830 or RG-115932.

In one embodiment, the invention provides an engineered population of DC. Day 7 cultured DC were untreated, were infected with recombinant adenovirus encoding murine IL-12p70 driven off a constitutive (rAd.cIL12) or inducible (rAd.RheoIL12) promoter, or were infected with mock, control adenovirus vector (rAdψ5), over a range of multiplicity of infection (MOIs). After 48 h, infected DC were harvested and analyzed for phenotype and for production of IL-12p70 using a specific ELISA kit (BD-PharMingen, San Diego, Calif.), with a lower level of detection of 62.5 pg/ml.

In another embodiment, the invention provides in vitro engineered population of DC, immune cells other than DC, or TSC comprising a vector, e.g., a DNA vector, having a gene switch capable of conditionally expressing a protein having the function of IL-12, and further comprising activating ligand. In another embodiment, the invention provides in vitro engineered population of DC, immune cells other than DC, or TSC comprising a vector having a gene switch capable of conditionally expressing a protein having the function of IL-12 and/or a protein having the function of IFN-alpha, and further comprising activating ligand.

In a further embodiment, the invention provides a method of treating cancer, e.g., melanoma or glioma, by administering engineered DC, immune cells other than DC, or TSC to a patient and then administering an activating ligand, such as RG-115919, RG-115830 or RG-115932, to said patient. The patient may be a human or an animal with cancer. The treatment methods and products, engineered cells, kits, and ligands have application in human therapy and in veterinary animal therapy. Therefore, the products and methods are contemplated to be used for human and veterinary animal purposes.

The invention provides that conditional expression of IL-12 protein in DC (referred to as DC.RheoIL12), immune cells other than DC, or TSC can overcome the immunologic impact of IL-12 early within the tumor lesion and later within tumor-draining lymph nodes that could not be resolved with regards to therapeutic outcome with conventional gene therapy schemes. It has further been discovered that the timing of expression of IL-12 after administration of engineered DC, immune cells other than DC, or TSC is critical to the successful treatment of cancer.

In one aspect, the invention provides a pharmaceutical composition suitable for administration to a human or a non-human comprising a population of in vitro engineered DC, immune cells other than DC, or TSC conditionally expressing a protein having the function of IL-12, or conditionally expressing IL-12 and/or IFN-alpha, wherein the formulation is suitable for administration by intratumoral administration. The invention further provides a pharmaceutical composition comprising an activating ligand, such as RG-115830 or RG-115932, wherein the composition is suitable for administration by intraperitoneal, oral, or subcutaneous administration.

In the particular embodiment described herein, the invention provides a method for treating a tumor, comprising:
  a. administering intratumorally in a mammal the in vitro engineered DC described above; and
  b. administering to said mammal a therapeutically effective amount of an activating ligand.

For example, the invention provides a method for treating a tumor, comprising the steps in order of:
  a. providing in vitro engineered DC;
  b. administering intratumorally in a mammal said in vitro engineered DC; and
  c. administering to said mammal a therapeutically effective amount of an activating ligand.

In another embodiment, the invention provides a method for treating a tumor, comprising:
  a. administering intratumorally in a mammal the in vitro engineered immune cells other than dendritic cells, e.g., macrophages, neutrophils, mast cells, eosinophils, basophils, natural killer cells and lymphocytes (e.g., B and T cells) or therapy support cells, which are described above; and
  b. administering to said mammal a therapeutically effective amount of an activating ligand.

In one embodiment, the in vitro engineered DCs, immune cells other than DC or TSCs are administered once. In another embodiment, the DCs, immune cells other than DC or TSCs are administered more than once if the single administration is proved to be safe and well tolerated and additional injection(s) would benefit the patient. The retreatment criteria is that the subject's disease is stable or showing clinical (i.e., CT scans (regression of tumor(s)), serum chemistry, urinanalysis, hematology, vital signs, decrease in tumor diameter, etc.) or subjective signs (i.e., improved ECOG status, etc.) of improvement. The retreatment may be initiated at 1, 2, 3, or 4 weeks, 1, 2, 3, 4, 5, 6, 7, 8, 9, 10, 11, or 12 months, or 1, 2, 3, 4, or 5 years of the first treatment.

The efficacy and safety of multiple doses of the transgene may evaluated by fine needle aspiration biopsies of the tumor and associated draining lymph nodes. These may be collected on day −12 to −7 and day 14 of the retreatment period for in vivo assessment of transgene expression of hIL-12 and cellular immune response. Biopsies may be evaluated by standard light microscopy and immunohistochemistry to assess cellular infiltration of T cells into the tumor and draining lymph nodes, RT-PCR on RNA may be used with appropriately designed primers. Blood may be drawn for a serum cytokine profile on day −12 to −7, day 8 and day 14 of the retreatment period. A serum cytokine profile may be obtained to determine if the expression of other cytokines is affected by treatment with the hIL-12 transgene. Multiplex cytokine testing may be done in the serum by Luminex for IL-12, INF-gamma, IP-10, and other Th1/Th2 cytokine such as IL-1, TNF-alpha, IL-4, IL-5, and IL-10.

In one embodiment, the activating ligand is administered at substantially the same time as the in vitro engineered DC, immune cells other than DC, or TSC, e.g., within one hour before or after administration of the cells. In another embodiment, the activating ligand is administered at or less than about 24 hours after administration of the in vitro engineered DC, immune cells other than DC, or TSC. In still another embodiment, the activating ligand is administered at or less than about 48 hours after the in vitro engineered DC, immune cells other than DC, or TSC. In another embodiment, the ligand is RG-115932. In another embodiment, the ligand is administered at a dose of about 1 to 50 mg/kg/day. In another embodiment, the ligand is administered at a dose of about 30 mg/kg/day. In another embodiment, the ligand is administered daily for a period of 5 to 28 days. In another embodiment, the ligand is administered daily for a period of 14 days. In another embodiment, about $1 \times 10^6$ to $1 \times 10^8$ cells are administered. In another embodiment, about $5 \times 10^7$ cells are administered.

To demonstrate an effective IL-12-mediated gene therapy, a conditional IL-12 cDNA expression system is used that allows one to turn on IL-12 production by DC.RheoIL12 cells at various time points post-intratumoral injection. Based on the results in the aggressive B16 melanoma model in C57BL/6 mice, the following conclusions were made: 1) elevated levels of IL-12 are secreted from DC.RheoIL12 in the presence of the activating ligand RG-115830 but not in the absence of the ligand; 2) intratumoral DC.RheoIL12-based therapy is as effective as intratumoral DC.cIL12-based therapy as long as RG-115830 is administered to treated animals within 24 h of DC injection (and at later time points of ligand provision, RG-115830 therapy fails); 3) IL-12 expression in DC appears to prolong the survival of these cells in the tumor microenvironment and is associated with higher numbers of intratumorally-injected DC that migrate to tumor-draining lymph nodes; and 4) the strongest immune correlate to therapy outcome is the level of tumor-specific CD8$^+$ T cells cross-primed by the therapy and not the number of injected DC sustained in the tumor microenvironment. Overall, these data suggest that DC.IL12-based therapies likely succeed based on their positive influence on the afferent (cross-priming) of Type-1 CD8$^+$ T cell effectors and not on later efferent events, such as injected DC-mediated recruitment of anti-tumor T cells into the tumor microenvironment, etc.

Prior to intratumoral injection, the cells (immune cells or TSC) may be treated with a factor to stimulate the activity of the cells. For example, the cells may be treated with a co-stimulatory molecule such as positive co-stimulatory molecule including OX40L, 4-1BBL, CD40, CD40L, GITRL, CD70, LIGHT or ICOS-L or a negative co-stimulatory molecule such as anti-CTLA4, anti-PD-L1 or anti-PD-L2 antibodies. For example, the cells (e.g., DC, immune cells or TSC) may be incubated with a cell expressing one or more co-stimulatory molecule, e.g., J588 lymphoma cells expressing CD40 ligand molecule. In another embodiment, the cells (immune cells or TSC) may be treated with a counter immune suppressant molecule (tolerance inhibitor) such as anti-TGF-beta antibodies (for inhibiting TGF signaling within the microenvironment), anti-IL10 antibodies, TGF-beta RII DN (to inhibit TGF signaling within gene modified cells), IL-10R DN, dnFADD (to inhibit cell death pathways within the cells), anti-SOCS I antibodies, siRNA or decoy (to inhibit suppressive cytokine signaling within the cells), or anti-TGF-alpha antibodies.

IL-12 production from DC and other antigen presenting cells acts on $CD4^+$ and $CD8^+$ T cells to skew them into a Th1 or Tc1 type phenotype, respectively. Therefore, it is possible to measure the effect of IL-12 on a population of cells by measuring the level of expression or activity of the Th1/Tc1 type cytokine, IFN-γ in a biological sample from a patient.

For the purposes of the invention, the invention provides a method for determining the efficacy of an in vitro engineered DC-, immune cells other than DC- or TSC-based therapeutic regimen in a cancer patient, comprising:

a. measuring the level of expression or the level of activity or both of interferon-gamma (IFN-γ) in a first biological sample obtained from a human patient before administration of in vitro engineered DC, immune cells other than DCs, or TSC, thereby generating a control level;

b. administering intratumorally to said patient the in vitro engineered DC, immune cells other than DCs, or TSC;

c. administering to said patient an effective amount of activating ligand;

d. measuring the level of expression or the level of activity or both of IFN-γ in a second biological sample obtained from said patient at a time following administration of said activating ligand, thereby generating data for a test level; and e. comparing the control level to the test level of IFN-γ, wherein data showing an increase in the level of expression, activity, or both of IFN-γ in the test level relative to the control level indicates that the therapeutic treatment regimen is effective in said patient.

In one embodiment, the invention provides a method for determining the efficacy of an in vitro engineered immune cells other than DC or TSC-based therapeutic regimen in a cancer patient, comprising:

a. measuring the level of expression or the level of activity or both of interferon-gamma (IFN-γ) in a first biological sample obtained from a human patient before administration of in vitro engineered immune cells other than DC or TSC, thereby generating a control level;

b. administering intratumorally to said patient in vitro engineered immune cells other than DC or TSC;

c. administering to said patient an effective amount of activating ligand;

d. measuring the level of expression or the level of activity or both of IFN-γ in a second biological sample obtained from said patient at a time following administration of said activating ligand, thereby generating data for a test level; and e. comparing the control level to the test level of IFN-γ, wherein data showing an increase in the level of expression, activity, or both of IFN-γ in the test level relative to the control level indicates that the therapeutic treatment regimen is effective in said patient.

The term "subject" means an intact insect, plant or animal. It is also anticipated that the ligands will work equally well when the subject is a fungus or yeast. The term "subject" is meant any subject, particularly a mammalian subject, for whom diagnosis, prognosis, or therapy is desired. Mammal include, but are not limited to, humans, domestic animals, farm animals, zoo animals such as bears, sport animals, pet animals such as dogs, cats, guinea pigs, rabbits, rats, mice, horses, cattle, bears, cows; primates such as apes, monkeys, orangutans, and chimpanzees; canids such as dogs and wolves; felids such as cats, lions, and tigers; equids such as horses, donkeys, and zebras; food animals such as cows, pigs, and sheep; ungulates such as deer and giraffes; rodents such as mice, rats, hamsters and guinea pigs; and so on. In certain embodiments, the animal is a human subject.

The term "animal" is intended to encompass a singular "animal" as well as plural "animals" and comprises mammals and birds, as well as fish, reptiles, and amphibians. The term animal also encompasses model animals, e.g., disease model animals. In some embodiments, the term animal includes valuable animals, either economically or otherwise, e.g., economically important breeding stock, racing animals, show animals, heirloom animals, rare or endangered animals, or companion animals. In particular, the mammal can be a human subject, a food animal or a companion animal.

As used herein, an "mammal in need thereof" refers to a mammal for whom it is desirable to treat, i.e., to reduce the size of a tumor or eliminate a tumor.

The method of the invention depends on the tumor antigen capture by the intratumorally injected dendritic cells from the tumor environment and priming the T cells in the draining lymph nodes to develop a tumor-specific T cell response. Therefore, the DC should be at a state of high endocytotic activity at the time of intratumoral injection for optimal therapeutic benefit. It has been well established that the immature DCs prepared from CD14+ monocytes by treatment with GM-CSF and IL-4 for about 6-7 days are of immature phenotype and show high rate of endocytosis (Cella et al. 1999; Gilboan, 2007). Maturation of DCs is associated with suppression of the endocytic activity. IL-12 has been shown to act on the immature DCs and signal the expression of maturation inducing factors (Nagayama et al. 2000). Therefore, by using the RTS, it is possible to optimize the human therapeutic outcome by delaying the expression of IL-12 in the transduced DC till they are injected into the tumor. Since a constitutive expression system lacks this ability to temporally control the expression, the autocrine action of the IL-12 produced and the resultant course of maturation cannot be controlled (Mazzolini et al. 2005). In addition, the invention which will test the performance of a regulated gene expression system in human subjects can find the application of the system in other human gene therapy areas.

Without wishing to be bound by theory, it is expected that the invention will support the use of intratumorally administered in vitro engineered DC-, immune cells other than DC- or TSC-based gene therapy in the clinical setting, focusing on the objective clinical response as a primary study endpoint, and cross-primed anti-tumor $CD8^+$ T cells (producing IFN-γ) as a secondary study endpoint. Data reveals that the ability to turn the M-12 expression on and off in vivo adds an element of safety and therapeutic control to the treatment in that both the timing and level of IL-12 expression may be controlled by the administration of ligand, and further that the timing of IL-12 expression is expected to be critical to the therapeutic effectiveness of the method.

The invention further supports the therapeutic applications of in vitro engineered cells with conditionally expressed genes of interest as innovative approaches for the effective and efficient treatment of human diseases.

In the event of conflict between any teaching or suggestion of any reference cited herein and the specification, the latter shall prevail, for purposes of the invention.

Specific embodiments according to the methods of the invention will now be described in the following examples, which are provided for the purposes of illustration and are not intended to limit the scope of the prevent invention.

EXAMPLES

Example 1

DC.RheoIL12 Conditionally Produce High Levels of IL-12p70 in Response to Ligand RG-115830 In Vitro 1.1 Materials and Methods 1.1.1 Mice Female 6-8 week old C57BL/6 wild-type and C57BL/6-TgN(ACTbEGFP)1Osb/J EGFP Tg mice were purchased from the Jackson Laboratory (Bar Harbor, Me.) and maintained in micro-isolator cages. Animals were handled in accordance with recommendations for the proper care and use of laboratory animals.

1.1.2 Cell Lines

The B16 melanoma and EL-4 thymoma H-2b cell lines, syngenic to C57BL/6 mice have been described previously (Itoh et al., 1994). Cell lines were maintained in CM (RPMI 1640 supplemented with 10% heat-inactivated fetal bovine serum, 100 units/ml penicillin, 100 µg/ml streptomycin, and 10 mM L-glutamine; all reagents from Invitrogen, Carlsbad, Calif.) in a humidified incubator at 5% $CO_2$ and 37° C.

1.1.3 Generation of Dendritic Cells (DC)

DCs were generated from murine bone marrow as previously described (Tatsumi et al., 2003). Briefly, wild-type or EGFP Tg mouse BM was cultured in CM supplemented with 1000 units/ml recombinant murine granulocyte/macrophage colony-stimulating factor and recombinant mIL-4 (Peprotech, Rocky Hill, N.J.) at 37° C. in a humidified, 5% $CO_2$ incubator for 7 days. $CD11c^+$ DC were then isolated using specific MACSTM beads, per the manufacturer's protocol (Miltenyi Biotec, Auburn, Calif.). $CD11c^+$ DC produced in this manner were >95% pure based on morphology and co-expression of the CD11b, CD40, CD80, and class I and class II MHC antigens.

1.1.4 Viral Vectors

The control adenoviral vector rAd.ψ5 and rAd.cIL12, encoding mIL-12 driven off a CMV promoter (Tatsumi et al., 2003), were produced and provided by the University of Pittsburgh Cancer Institute's Vector Core Facility.

The rAd.RheoIL12 vector was produced in the following manner. The coding sequences for VP16-RXR and Gal4-EcR separated by the EMCV internal ribosome entry site (IBES) sequence were inserted into the adenoviral shuttle vector under the control of the human ubiquitin C promoter. Subsequently, the coding sequences for the p40 and p35 subunits of IL12 separated by an IRES sequence, and placed under the control of a synthetic inducible promoter, were inserted upstream of the ubiquitin C promoter (See FIG. 1). The performance of the system by expressing the two fusion proteins (VP-16 RXR v. Gal4-EcR) under separate promoters of varying strengths showed that a higher VP16-RXR to Gal4-EcR ration gave the best performance. Thus, VP-16 RXR upstream of the IRES and Gal-4 EcR downstream gave optimal performance than the converse design.

The shuttle vector carrying these transcription units for the two fusion proteins and inducible IL12 subunits was recombined with the Adenoviral backbone (AdEasy1, stratagene, La Jolla, Calif.) in *E. coli* BJ5183 cells. After verifying the recombinant clone, the plasmid carrying the rAd.RheoIL12 genome was grown in and purified from XL10-Gold cells, digested off the plasmid backbone and packaged by transfection into HEK 293 cells.

The resulting primary viral stock was amplified by re-infection of HEK 293 cells and was purified by CsCl density-gradient centrifugation.

1.1.5 ELISA

Day 7 cultured DC were untreated, were infected with recombinant Ads encoding murine IL-12p70 driven off a constitutive (rAd.cIL12) or inducible (rAd.RheoIL12) promoter, or were infected with mock, control vector rAd.ψ5, over a range of MOIs. At various time points after this (0-48 h), DC were then cultured in the absence or presence of an activating ligand (10-200 µg/ml) for an additional 24 h prior to analysis of IL-12p70 secretion using a specific ELISA kit (BDPharMingen, San Diego, Calif.; lower level of detection=62.5 pg/ml). In some cases, to discern the stringency of conditional cytokine production, DC infected with rAd.RheoIL12 (i.e. DC.RheoIL12), that had been pretreated with the activating ligand, were washed free of ligand and cultured in control media for an additional 24 h prior to analysis of IL-12p70 secretion. Alternatively, after 48 h, infected DC were harvested and analyzed for phenotype and for production of IL-12p70 using the ELISA kit (BD-PharMingen, San Diego, Calif.), with a lower level of detection of 62.5 pg/ml.

1.1.6 Flow Cytometry

For phenotypic analysis of adenovirus infected DC, PE- or FITC-conjugated mAbs against mouse cell surface molecules (CD11b, CD11c, CD40, CD54, CD80, CD86, H-2 Kd, I-Ad (all from BD-PharMingen)) and appropriate isotype controls were used, and flow cytometric analysis was performed using a FACscan (Becton Dickinson, San Jose, Calif.) flow cytometer.

1.2 Results 1.2.1 Murine BM-Derived DC Infected with Rheo-IL12 Conditionally Produce High Levels of IL-12p70 when Treated with Ligand In Vitro.

Figures 2A, 2B:
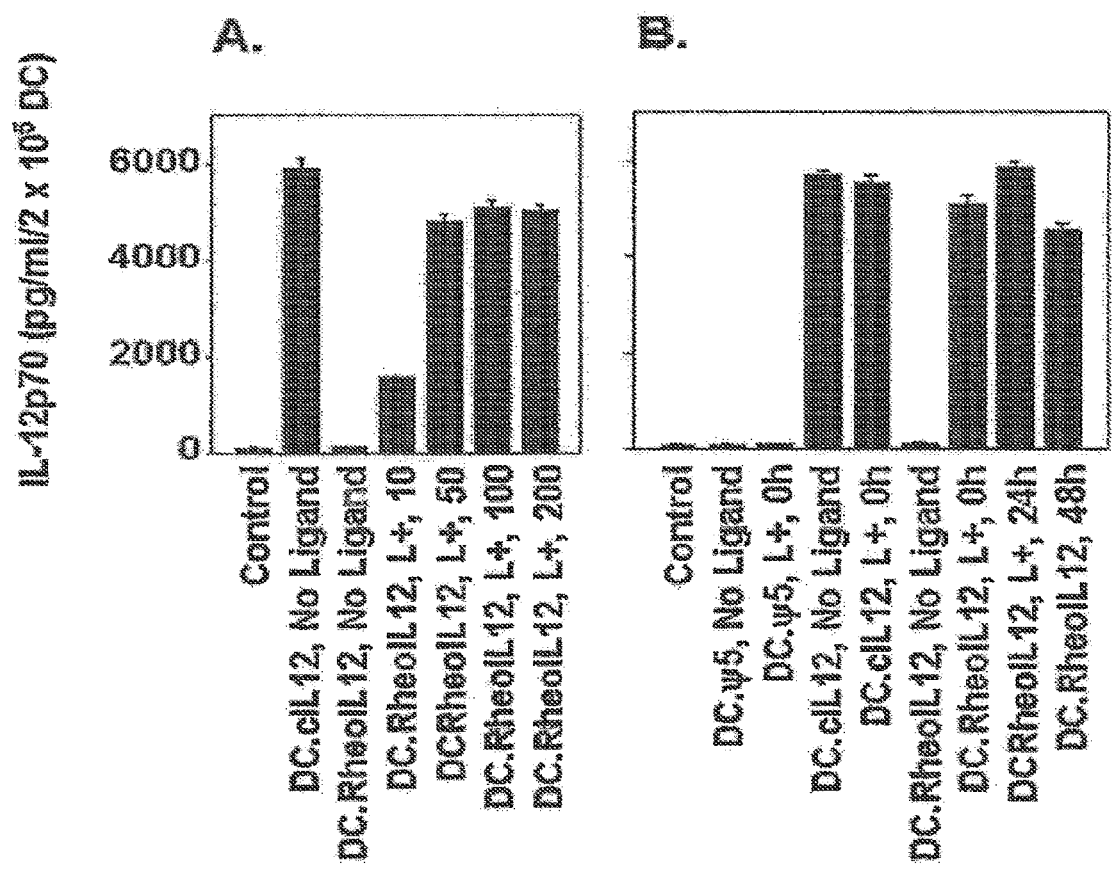
FIGS. 2A-2C show that engineered DCs conditionally express IL-12 protein in the presence of RG-115830.
Figure 2C:
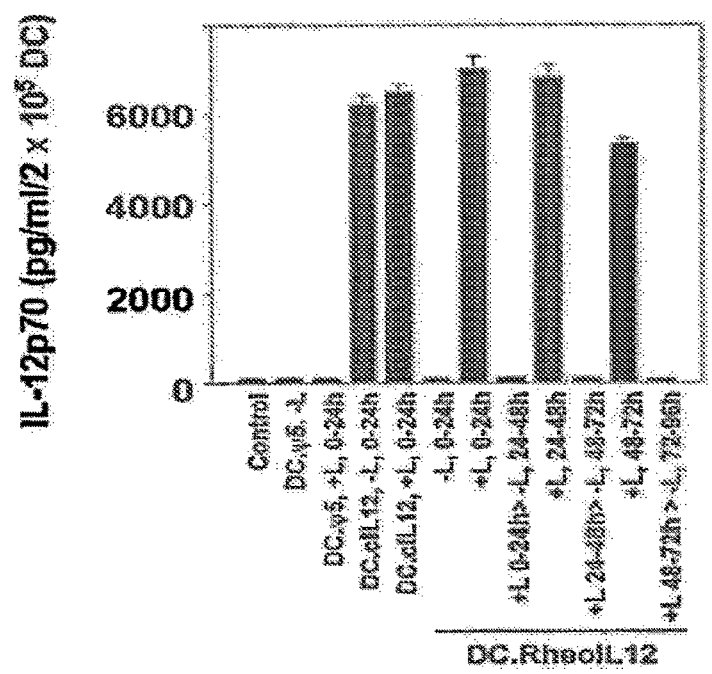

DC cultured from C57BL/6 (B6) mouse BM for 7 days in the presence of rmIL-4 and rmGM-CSF were left untreated, or infected at various MOIs with control rAd.ψ5, rAd.cIL-12 (encoding mIL-12p70 under a constitutive CMV promoter) or rAd.RheoIL12 (encoding IL-12 p70 under a conditional promoter responsive to the small molecule ligand RG-115830). Forty-eight hours after infection, DC were cultured in the absence or presence of RG-115830 for an additional 24 h, at which time, culture supernatants were harvested for quantitation of IL-12p70 production by ELISA. As shown in FIG. 2A, control uninfected DC or DC infected with Ad.ψ5 in the absence or presence of exogenous drug failed to produce elevated levels of IL-12p70 when compared with DC infected with rAd.cIL12 (DC.cIL12). DC infected with rAd.RheoIL-12 (DC.RheoIL12) only produced IL-12p70 when treated with RG-115830 (See FIGS. 2A and 2B). Based on the results of "criss-cross" experiments, optimal infected DC production of IL-12p70 occurred using an MOI of 100, with cells treated with 50-200 µg/ml RG-115830 (FIG. 2A). Delayed provision of RG-115830 to DC.RheoIL12 for up to 48 h did not result in any significantly reduced production of IL-12p70 when compared to addition of this ligand at the 0 h timepoint in vitro (FIG. 2B). Finally, removal of ligand acutely silenced the ability of DC.RheoIL12 (previously activated by ligand) to continue to produce elevated levels of IL-12p70 in vitro (FIG. 2C).

Example 2

Intratumoral Administration of In Vitro Engineered Dendritic Cells to Animals 2.1 Methods and Materials 2.1.1 B16 Tumor Model B6 mice received subcutaneous injection of $1\times10^5$ B16 melanoma cells in the right flank on day 0. On day 7, tumors reached a size of approximately 20-30 mm$^2$ and mice were treated with i.t. injections of PBS or $1\times10^6$ control vs. adenoviral transduced (MOI=100) DC in a total volume of 50 µl of PBS. Mice also received i.p. injections of 200 µg RG-115830 (in 50 µl DMSO) vs. DMSO carrier control that were initiated at 0 h, 24 h or 48 h post-DC administration, as indicated. After initiation, mice received a total of 5 consecutive daily intraperitoneal injections of RG-115830 at this dose. In additional experiments, ligand was administered beginning on the day of DC injection and then terminated 1, 3 or 5 days post-DC injection to discern whether early cessation of IL-12p70 transgene promotion reduced the therapeutic benefits of this approach. In all cases, tumor size was assessed every 3 or 4 days and recorded in mm$^2$ by determining the product of the largest perpendicular diameters measured by vernier calipers. Data are reported as the average tumor area±SD. All animal cohorts contained 5 mice/group.

In indicated experiments, animals rendered tumor-free (45 days) post-therapy were rechallenged with the B16 melanoma ($10^5$ cells injected on the left flank, i.e. contralateral to the original B16 challenge site) and MC38 colon carcinoma ($10^5$ cells on the right flank) cells in order to discern the presence and specificity of memory immunity in these mice. All data are reported as the average tumor area±SD. All animal cohorts contained 5 mice/group.

To assess the fate and function of injected DC, day 7 BM-derived, CD11c$^+$ DC were generated from C57BL/6-TgN(ACTbEGFP)1Osb/J EGFP Tg mice. EGFP$^+$ CD11c$^+$ DC were left uninfected or were infected with rAd viruses, as indicated above. Forty-eight hours after infection, $1\times10^6$ control or virally-infected DC were harvested, washed in PBS, and injected into day 7 B16 tumor lesions established in syngenic B6 mice. Three days after DC injection, tumors and draining inguinal lymph nodes (LN) were resected, fixed for 1 h in 2% paraformaldehyde (in PBS), and then cryoprotected in 30% sucrose in PBS before being shock frozen in liquid nitrogen-cooled isopentane. Five micron frozen sections were then generated and counterstained with 2 mg/ml Hoechst 33258 (Sigma-Aldrich, St. Louis, Mo.) for 3 min. The washed sections were then mounted in Gelvatol (Monsanto Chemical Co., St. Louis, Mo.) and observed using an Olympus BX51 microscope equipped with a cooled charge-coupled device color camera.

2.1.2 Assessment of Specific CM$^+$ T Cell Responses Against B16 Melanoma

Pooled CD8$^+$ T cells were isolated to a purity of >95% from the spleens of 2 treated mice/group 25 days after tumor inoculation using magnetic bead cell sorting (MACSTM; Miltenyi Biotec) and then co-cultured ($1\times10^5$/well) with $1\times10^4$ irradiated (10,000 rads) B16 or EL-4 tumor cells. After 48 h incubation, culture supernatants were collected and analyzed for IFN-γ release using a commercial ELISA (BD-PharMingen) with a lower limit of detection of 31.5 pg/ml. Data are reported as the mean SD of triplicate determinations.

2.1.3 Statistical Analysis

All experiments with three or more groups in which treatment was applied as a completely randomly design were first analyzed by a one-way or two-way factorial ANOVA. If the resulting P was <0.05, specific pairwise contrasts were tested with a T test with Welch's correction for unequal variance as needed. Data were checked for distributional properties, and appropriate transformations were applied. Analyses of IFN-γ production from splenocyte-derived T cells were conducted with the exact Kruskal-Wallis test. If the P for the Kruskal-Wallis test was <0.05, priori contrasts were evaluated with the Wilcoxon test. The analysis of therapeutic single tumor inoculation murine treatment models was conducted with mixed linear models. Data were log transformed, within-mouse covariance was estimated, and fixed effects of treatment were adjusted for random mouse effects. Raw Ps for comparing pairs of groups at a single time were adjusted by bootstrap re-sampling. Tumor rejection rates were fit to a generalized linear model (with binomial link) that incorporated treatment group, day of observation, and their interaction.

Figures 3B, 3C:
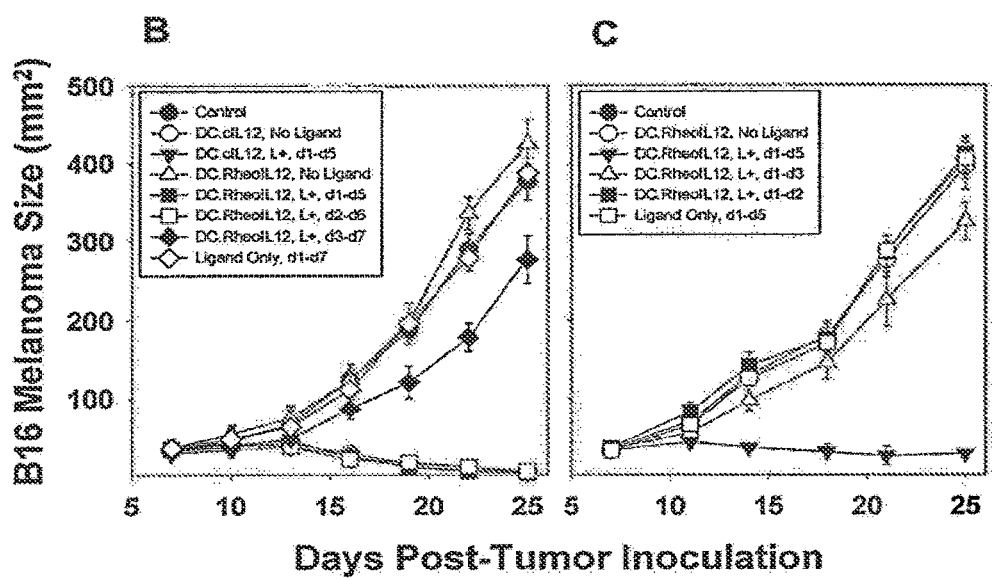

2.2 Results 2.2.1 Intratumoral Administration of DC.cIL12 Alone or DC.RheoIL12 Combined with i.p. Administration of RG-115830 Promotes the Regression of Established s.c. B16 Melanoma Lesions B16 melanoma cells ($1\times10^5$) were injected s.c. in the left flank of syngenic H-2$^b$ B6 mice and allowed to establish. On day 7, mice were randomized into cohorts of 5 animals each, with a mean cohort tumor size of approximately 20-30 mm$^2$. Mice then received intratumoral injections of PBS or $10^6$ DC (pre-infected in vitro for 48 h with rAd.ψ5, rAd.cIL12 or rAd.RheoIL12) in a total volume of 50 µl PBS. Animals also received DMSO or RG-115830 (in DMSO) intraperitoneal injections at the time of DC administration (i.e., day 1 of treatment) or at 24 h or 48 h post-DC administration (i.e., day 2 of treatment). As depicted in FIGS. 3A and 3B, the treatment of mice with RG-115830 alone or DC.RheoIL12 in the absence of RG-115830 failed to yield any therapeutic benefit. In marked contrast, tumors treated with DC.cIL-12 or DC.RheoIL-12+RG-115830 (provided within 24 h of DC injection in concert with a 5 day course of ligand administration) regressed in size over the following 3 weeks. These therapies were statistically indistinguishable based on tumor size measurements, and yielded 100% (5/5 mice) tumor regression rates in each of these instances. Interestingly, if RG-115830 administration was delayed until 48 h after intratumoral DC injection (at a time point when this agent can efficiently promote IL-12p70 production from DC.RheoIL-12 in vitro, See FIG. 2B), DC.RheoIL12-based therapy resulted in a slightly inhibited tumor growth rate (p<0.05 for all time points after day 10), but all animals progressed and required sacrifice by day 30 (FIG. 3A). This suggests that therapeutic benefit of intratumoral DC.IL12 treatment is critically dependent upon IL-12p70 production at predominantly early time points (occurring presumably within the tumor lesion and/or draining lymph nodes).

Additional experiments were performed in which activating ligand (RG-115830) was administered to DC.RheoIL-12 injected mice for 1, 3 or 5 days post-DC injection (FIGS. 3B-3C). The results of these studies suggest that early termination of ligand administration impacts the anti-tumor efficacy of i.t. delivered DC.RheoIL-12, with inhibition of tumor growth limited or ablated if ligand is not provided to mice for approximately 5 or more days after provision of gene-modified DC. These findings are consistent with data provided in FIGS. 2B and 2C, and support the tight (ligand-dependent) regulation of therapeutic impact resulting from injected DC.RheoIL-12 in this model. Furthermore, when taken together, the results depicted in FIG. 3 strongly suggest that optimal anti-melanoma efficacy associated with i.t. delivery of DC.RheoIL12 results from provision of the ligand during the d1-d5 period post-DC injection into B16 tumors.

2.2.2 Delayed Activation of Conditional DC.RheoIL12 Therapy is Ineffective Due to the Apparent Failure of Injected DC to Survive In Vivo.

Our previous report (Tatsumi et al., 2003) suggested that IL-12 gene insertion into DC promotes the enhanced survival of these cells after injection into the tumor microenvironment and the consequent capacity of these cells to cross-prime anti-tumor $CD8^+$ T cells and conceivably recruit circulating effector T cells into the tumor microenvironment in vivo. Hence, the next attempt was to discriminate whether the failure of DC-RheoIL12 therapy initiated (by i.p. RG-115830 administration) 48 h after DC injection was due to the inability of DC to persist in the tumor microenvironment, the inability of these cells to traffic to tumor-draining LN and/or the inability of specific $CD8^+$ T cells to be cross-primed as a result of treatment. Experiments as outlined in FIG. 3A were recapitulated, with 2 mice per cohort sacrificed 72 h after intratumoral injection of DC, with the exception that EGFP Tg ($H-2^b$) mice were used as the source of bone marrow for DC generation. Tumor and LN were resected and tissue sections prepared for analysis of $EGFP^+$ DC by fluorescence microscopy. The remaining 3 animals/cohort were followed until day 25, when they were sacrificed and pooled splenocytes isolated for analysis of B16-specific $CD8^+$ T cell responses.

As depicted in FIG. 4, the ability to resolve $EGFP^+$ DC in tumor or LN 72 h after i.t. injection was strictly dependent on the activation of the 11-12 transgene within 24-48 h of in vivo administration of these cells. $EGFP^+$ DC.cIL12 and DC.RheoIL12 could be readily observed in B16 lesions and were seen more rarely within draining LNs in mice injected i.t. with DC.cIL12 or DC.RheoIL12 (if RG-115830 was provided i.p. at 0 h or 24 h post-DC administration). Very few or no $EGFP^+$ DC were detectable in tissues harvested from mice treated with control (uninfected) DC or DC.RheoIL12 (where RG-115830 administration was delayed for 48 h post-DC injection). When comparing the tissues isolated from mice treated with DC.RheoIL12 and RG-115830 provided at 0 h vs. 24 h, there were more $EGFP^+$ DC in both the tumor (p=0.001) and draining LN (p=0.02) when the activating drug was provided earlier.

2.2.3 Therapeutic Benefits of DC.RheoIL12 Administration are Associated with the Induction of Specific CD8+ T Cells and Durable Anti-Tumor Immunity.

Given the apparent dependency of injected DC vitality on the timing of ligand injection, we would have predicted a superior degree of specific $CD8^4$ T cell cross-priming in the case of mice receiving DC.RheoIL12 activated at 0 h vs. later time points by RG-115830. Interestingly, while this was certainly observed for the 0 h (DC.RheoIL-12, d1-d5) vs. 48 h (DC.RheoIL-12, d3-d7) DC.RheoIL-12 cohorts, it was not the case when comparing the 0 h vs. 24 h (DC.RheoIL-12+L,d2-d6) DC.RheoIL12 groups (FIG. 5A). Indeed, the in vitro splenic $CD8^+$ T cell responses (IFN-γ secretion) against relevant B16 vs. irrelevant EL-4 tumor targets was comparable for both of these cohorts, and these each approximated that detected in mice treated with DC.cIL12. Overall, these $CD8^+$ T cell response profiles appeared to directly correlate with the therapy outcome (FIG. 3A). Similar to FIG. 5A, splenic T cells response to the specific B16 tumor cells vs. unrelated MC38 cells by IFN-gamma production was correlated to the treatment outcome.

To address whether effective DC.RheoIL12-based therapy was associated with the development of durable anti-tumor immunity, tumor-free animals were (re)challenged with relevant B16 melanoma cells or irrelevant MC38 colon carcinoma cells on day 45 (post-initial B16 challenge). As shown in FIG. 5B, all mice previously cured of their melanomas exhibited specific protection against B16 tumor cells, whereas MC38 tumor lesions grew progressively. It shows that the dendritic cells of the invention have additional safety and potential therapeutic control to the treatment modality (in that both the timing and level of IL-12 expression may be controlled by the administration of ligand).

Example 3

Comparison or Ligand Route/Dose of Administration on Therapeutic Effect 3.1 Methods and Materials B16 melanomas were established s.c. for 7 days in the right flanks of syngenic B6 mice. On day 7, $10^6$ DC.SP1-IL12 (optimal switch identified in FIG. 10 comparison) were injected intratumorally (i.t.). Activating ligand (RG-115932) was provided either as an injection i.p., via oral gavage in Labrasol, or via drug-containing chow provided ad libitum beginning on the day preceding DC injection (and daily thereafter for 6 days). Each cohort contained 5 animals, with tumor growth monitored every 3-4 days and reported as mean size ($mm^2$ based on the product of orthogonal measurements). The treatment for each cohort is described below.

| Cohort # | Treatment Description |
| --- | --- |
| 1 | Control, No DC, No ligand |
| 2 | Control, No DC, Ligand i.p., 50 mg/kg/day (Max) |
| 3 | Control, No DC, chow, ad libitum (45 mg/kg/day) |
| 4 | Control, No DC, oral gavage, 30 mg/kg/day |
| 5 | DC.SP1-IL12, No ligand |
| 6 | DC.SP1-IL12, i.p., 1 mg/kg/day |
| 7 | DC.SP1-IL12, i.p., 3 mg/kg/day |
| 8 | DC.SP1-IL12, i.p., 10 mg/kg/day |
| 9 | DC.SP1-IL12, i.p., 30 mg/kg/day |
| 10 | DC.SP1-IL12, i.p., 50 mg/kg/day |
| 11 | DC.SP1-IL12, chow, ad libitum (45 mg/kg/day) |
| 12 | DC.SP1-IL12, oral gavage, 30 mg/kg/day |

3.2 Results

The results show that administration of ligand alone at any dose or via any route had no impact on B16 tumor growth (FIG. 6). DC-SP1 i.t. therapy is effective in controlling B16 growth, but only if ligand is applied, with all routes of ligand administration yielding some degree of efficacy. DC-SP1 i.t. therapy using i.p. administered ligand yielded a clear ligand dose-tumor inhibition response pattern, with optimal anti-tumor effects at ligand doses >30 mg/kg/day. Ligand applied to DC-SP1 i.t. therapy at a dose of 30 mg/kg/day was equally effective if ligand is administered by i.p. injection, oral gavage, or diet admix. An even higher dose of ligand provided in chow was somewhat less effective. Since only the R enantiomer (RG-115932) is capable of activating the RTS, chow containing the racemic mixture provides only c.a. 20-22.5 mg/kg/day of the active enantiomer. In this regard, tumor regression observed in animals receiving racemic mixture AD via chow (i.e., ~20-22.5 mg/kg/day of the active enantiomer RG-115932) was consistent with the i.p. dose response seen with pure RG-115932 in that the anti-tumor effect in the cohort on chow fell between that observed with the 10 and 30 mg/kg/day i.p. RG-115932 dose groups. These data suggest that oral administration of the ligand is effective for inducing a therapeutic effect. The availability of oral administration of the ligand would ease the burden of the treatment on patients.

This Activator Drug dependent effect was associated with (1) transgene expression in the tumor and DLN, (2) prolonged Ad-DCs survival in the tumor microenvironment, (3) migration and persistence of AdDCs in the DLN, and (4) induction of anti B16 CD8+ T cells.

FIG. 10 shows a comparison of the effects of different IL-12-containing adenoviral vectors. The SP1-RheoIL-12 variant was the most effective of the Rheoswitch-containing variants. SP1-RheoIL-12 differs from oldRheoIL-12 in the vector backbone (AdEasy1 vector for the 'oldRheoIL-12 and RAPAd vector of ViraQuest on the Sp1-RheoIL-12). TTR-RheoIL-12 differs from oldRheoIL-12 in that it contains a TTR minimal promoter downstream of the Gal4 response element. As FIG. 10 illustrates, SP1-RheoIL-12 was more effective than TTR-RheoIL-12 in reducing B16 melanoma tumor size.

FIG. 11 shows lack of B16 melanoma tumor formation after rechallenge of mice previously treated with dendritic cells containing recombinant adenoviral Rheoswitch inducible IL-12 (DC-SP1-RheoIL-12). This shows that B16 melanoma tumors were prevented from growing for up to 25 days when B16 immune mice were re-inoculated 45 days after the first inoculation with B16 cells. Murine dendritic cells were generated from bone marrow of B6 mice by 7 day culture in complete media (RPMI-1640, 10% FBS) containing rmIL-4 plus rmGM-CSF. CD11c positive dendritic cells were then isolated using specific MACS beads per manufacturer's protocol (Miltenyi Biotech) and infected at MOI of 100 using rAd.IL-12 (RheoIL-12 vs. SP1 vs. TTR) for 24 hours prior to injection of 10E6 DC into established day 9 s.c. B16 melanoma tumors (5 mice per group, tumor on right flank). Mice were treated or not with daily i.p. injections of the activating ligand RG-115830 (30 mg/kg in 50 microliter DMSO) on days 0-4 post DC injection. Tumor size was monitored every 3-4 days and is reported in mm squared as product of orthogonal diameters. To evaluate the specificity of therapy-associated protection, all tumor-free animals were rechallenged with 10E5 B16 melanoma cells on the left flank versus MC38 colon carcinoma cells on the right flank on day 45 post initial B16 tumor challenge. MC38 tumors formed but B16 tumors did not form.

FIG. 12 shows a comparison among numbers of dendritic cells (DC-SP1-RheoIL-12) injected into the B16 tumor ($10^5$, $10^6$, $10^7$) and length of time of ligand administration and tumor regression in B16 melanoma tumor mouse model (6 days, 13 days). FIG. 12 shows the dependence of the dose of transduced DCs injected into the tumor and the duration of AD administration (i.p. injection, 30 mg/kg/day) on the inhibition of tumor growth. Tumor bearing mice were given a single intratumoral injection of AdDCs at doses of $10^5$, $10^6$, and $10^7$ cells and daily i.p. injection of Activating Ligand at a single dose of 30 mg/kg/day for 6 days or 13 days beginning on the day of the injection of $10^7$ cells. Also, a significantly more robust suppression of tumor growth was observed if the Activating Ligand were provided for 13 days instead of 6 days. Ligand (RG-115932) administered for 13 days in a row in combination with $10^7$ dendritic cells was effective in causing tumor regression over a 25 day period. This suggests that in contrast to the belief that ex vivo transduced DCs survive for only a few days after injection into tumors, the AdDCs expressing IL-12 under the control of the RTS are likely still intact for more than 1 week after intratumoral injection and may even remain alive and responsive to Activating Ligand for as much as 13 days after injection. There was no effect of the Activating Ligand alone (without AdDCs) on tumor growth.

In a similar experiment to FIG. 12, the Activating Ligand was administered by oral gavage for 9 and 12 days. The anti-tumor dose response with an oral formulation of the Activating Ligand at different doses in Labrasol was assessed. A dose dependent anti-tumor effect was observed and the greatest responses seen in animals receiving 50 mg/kg/day orally for 12 days. Indeed, at all doses tested, 13 days of the Activating Ligand treatment was superior to 9 days of the Activating Drug treatment. This suggests that DCs which survive and sustain IL-12 production for at least 9 to 12 days in vivo (either in the tumor microenvironment or lymphoid organs) are important for optimal treatment efficacy.

FIG. 13 shows that the therapy described herein was not associated with untoward loss in animal weight due to wasting. Wasting and weight loss is often associated with high levels of interferon-gamma and TNF-alpha which are known to be upregulated in response to IL-12.

B16 melanomas were established s.c. for 7 days in the right flanks of 5 syngeneic B6 mice. On day 7, DC.SP1-IL-12 (bone marrow derived DC infected at an MOI of 100 using the SP1 optimal switch) were injected intratumorally (i.t.) at doses of 10E5, 10E6 or 10E7. RG-115932 was provided by i.p. injection beginning on the day of DC injection (and daily thereafter for either 6 days or 13 days). Each cohort contained 5 animals, with tumor growth monitored every 3-4 days and reported as mean size (mm squared based on the product of orthogonal measurements). Individual animal weights were also assessed at the time of tumor measurements (FIG. 13). All animals rendered free of disease by any therapy were rechallenged on day 50 (post-initial B16 tumor inoculation) with 10E5 B16 melanoma cells on the opposite flank (left flank) of the original tumor and with 10E5 MC38 colon carcinoma cells on the right flank. Tumor growth was monitored every 3-4 days and compared against growth observed in naïve (untreated) animals (see FIG. 12).

FIG. 14 shows lack of B16 melanoma tumor formation after rechallenge of mice previously treated with dendritic cells containing recombinant adenoviral Rheoswitch inducible IL-12 and activator ligand RG-115932. FIG. 14 therefore shows that B16 melanoma tumors were prevented from growing for up to 24 days when B16 immune mice were re-inoculated with B16 cells. FIG. 14 also illustrates that B16 naïve mice were not protected from tumor formation, as were MC38 immune mice and MC38 naïve mice. MC38 is a colon carcinoma known in the art. This demonstrates the specificity of immunization caused by the original B16 tumor injection with dendritic cells containing recombinant adenoviral Rheoswitch inducible IL-12.

DCs produced by differentiation of CD14+ cells are of immature phenotype and do not produce detectable levels of IL-12 (Cella et al. 1999). FIG. 15 indicates that the murine DCs produced by treatment of bone marrow cells with GM-CSF and IL-4 for 7 days followed by CD11c+ selection also showed absence of detectable IL-12 expression after transeduction with the adenoviral vector harboring IL-12 under control of the RTS. Treatment of the transduced cells with varying doses of the Activator Drug (RG-115932) produced IL-12 in a dose dependent manner.

Adenoviral transduction has been reported to induce some degree of maturation in the DCs by penton-integrin interaction that leads to TNF-alpha production through the NFkB activation pathway. The autocrine action of TNF-alpha is reported to be the maturation-inducing signal for DCs in this case (Philpott et al. 2004). The short adenoviral transduction (2-3 hours) used and choosing the MOI to the minimal required levels are expected to limit this early maturation effect.

Example 4

In this example, dendritic cells were isolated from bone marrow, transduced with the Adenoviral constructs depicted in FIG. 7, and mice bearing syngeneic intracranial GL261 gliomas were intratumorally injected with engineered dendritic cells; and RG-115830 was injected intra-peritoneal. FIG. 7 shows the results of intratumoral injection of mouse intracranial glioma GL261 with dendritic cells transduced with polynucleotides encoding IL-12 and/or IFN-alpha under the control of RTS or lacking RTS. The data reveal that ligand induced expression of IFN-alpha and IL-12 through activation of the RTS with RG-115830 ligand promoted 75 percent survival at 50 days of GL261 glioma mice; as compared to IFN-alpha expression alone. Furthermore, the control provided by the RheoSwitch and ligand promoted enhanced survival.

Example 5

The safety, tolerance, transgene function, and immunological effects of intratumoral injection(s) of adenoviral transduced autologous dendritic cells engineered to express hIL-12 under control of the RTS in subjects with stage III and IV melanoma will be evaluated through procedures such as those described below.

A study involving study subjects with stage III and IV melanoma will be conducted in 4 cohorts (groups) of subjects each subject receiving a single intratumoral injection (into a melanoma tumor) of adenoviral transduced autologous (reinserted into the same subject that they came from) dendritic cells (DCs) engineered to express human interleukin-12 (hIL-12) at a dose of $5 \times 10^7$ in combination with daily oral doses of activator drug (activating ligand). The study will use injections of dendritic cells transduced ex vivo (after the cells are removed from the subjects) with adenoviral vector for inducible expression of human IL-12. The IL-12 production is "turned on" (induced) from the injected DCs through the activation of the RTS by the oral administration of the activator drug (RG-115932). Safety and tolerance will be assessed through physical examinations (including ECOG performance status), vital signs measurements, serum chemistry, urinalysis, hematology, adverse events "side-effects", and antibodies and cellular immune response to the adenovirus, components of RTS, and the Activator Drug. To evaluate progress, single dose and steady-state pharmacokinetics/ADME of oral Activator Drug and its major metabolites, analysis of hIL-12 levels and cellular immune response (T cells) in biopsies of the target tumors, draining lymph nodes, and peripheral circulation, as well as a serum cytokine profile will be measured.

For instance, 16 subjects with stage III and IV melanoma are divided into four cohorts with cohorts 1 and 2 containing three subjects and cohorts 3 and 4 containing 5 subjects. All subjects will receive a single intratumoral injection of $5 \times 10^7$ autologous DC transduced with adenoviral vector encoding human IL-12 under the RTS control. The subjects will receive a single daily oral dose of activator drug (cohort 1: 0.01 mg/kg, cohort 2: 0.1 mg/kg, cohort 3: 1.0 mg/kg or cohort 4: 3 mg/kg) the first does starting approximately 3 hours prior to the DC injection on day 1 and continuing for 13 more consecutive days. Additional injection(s) of adenovirally transduced autologous dendritic cells in combination with 14 single (once) daily oral doses of activator drug may be administered to eligible subjects who meet the criteria for retreatment. Safety, tolerance, and dendritic cell function are assessed for all subjects in each group of cohort 1 for up to one month after injection of the in vitro engineered dendritic cells before enrolling subjects to receive the next highest dose of the activator drug. The safety assessment will continue in all subjects for 3 months after the initial injection of the engineered dendritic cells with the possibility of extending the follow-up period to a total of six months to monitor subject safety if toxicity is observed or the subject receives additional injection(s) of the dendritic cells.

Such a study demonstrates the safety and tolerance of a single or multiple intratumoral injection(s) of adenoviral transduced autologous dendritic cells in combination with an oral activator drug in subjects with melanoma. The study provides steady-state pharmacokinetics/ADME of the oral activator drug. The study demonstrates functionality of the RTS in subjects by measuring hIL-12 expression of adenovirus transduced autologous dendritic cells in target tumor and/or draining lymph nodes in response to the activation of the RTS by the oral administration of the activator drug. Furthermore, the study demonstrates the immunological effects of the adenoviral transduced autologous dendritic cells in terms of the cellular immune response in the target tumor, draining lymph nodes, and peripheral circulation following oral administration of the activator drug.

Melanoma is selected as an exemplary cancer (for use with the RTS) because stage III and IV patients have no viable therapies available, melanoma in particular among solid tumors has been shown to respond to immunotherapy approaches, and melanoma tumors are readily accessible for intratumoral injection and biopsy. The subjects included in the study have unresectable stage III or IV melanoma, which has at least 0.5 cm in diameter, any tumor thickness, any number of lymph node involvement, in-transit metastases, or distant metastases.

5.1. Preparation of Adenovirus Harboring the RheoSwitch Therapeutic System and hIL-12

The recombinant DNA is transferred to dendritic cells (DC) by ex vivo adenoviral vector transduction. The recombinant DNA is used to express human IL-12(p70) from intratumorally injected immature dendritic cells which confers survival and stimulates maturation of DC in the tumor environment resulting in their subsequent migration to the draining lymph nodes. This leads to a bias toward the differentiation of T helper cells to Th1 type and also activation of tumor-specific cytotoxic T cells by cross priming with the tumor antigens.

The recombinant DNA used as the recombinant adenoviral vector allows the expression of human IL-12 under the control of the RheoSwitch® Therapeutic System (RTS). The RTS comprises a bicistronic message expressed from the human Ubiquitin C promoter and codes for two fusion proteins: Gal4-EcR and VP16-RXR. Gal4-EcR is a fusion between the DNA binding domain (amino acids 1-147) of yeast Gal4 and the DEF domains of the ecdysone receptor from the insect *Choristoneura fumiferana*. In another embodiment, the RTS consists of a bicistronic message expressed from the human Ubiquitin C promoter and codes for two fusion proteins: Gal4-EcR and VP16-RXR. Gal4-EcR is a fusion between the DNA binding domain (amino acids 1-147) of yeast Gal4 and the DEF domains of the ecdysone receptor from the insect *Choristoneura fumiferana*. VP16-RXR is a fusion between the transcription activation domain of HSV-VP16 and the EF domains of a chimeric RXR derived from human and locust sequences. These Gal4-EcR and VP16-RXR sequences are separated by an internal ribosome entry site (IRES) from EMCV. These two fusion proteins dimerize when Gal4-EcR binds to a small molecule drug (RG-115932) and activate transcription of hIL-12 from a Gal4 responsive promoter that contains six Gal4-binding sites and a synthetic minimal promoter. The RTS transcription unit described above is placed downstream of the hIL-12 transcription unit. This whole RTS-hIL12 cassette is incorporated into the adenovirus 5 genome at the site where the E1 region has been deleted. The adenoviral backbone also lacks the E3 gene. A map for the adenoviral vector Ad-RTS-hIL-12 is shown in FIG. 8.

The recombinant adenoviral vector used in this study contains the following exemplary regulatory elements in addition to the viral vector sequences: Human Ubiquitin C promoter, Internal ribosome entry site derived from EMCV, an inducible promoter containing 6 copies of Gal4-binding site, 3 copies of SP-1 binding sites, and a synthetic minimal promoter sequence, SV40 polyadenylation sites, and a transcription termination sequence derived from human alpha-globin gene. It should be understood that other regulatory elements could be utilized as alternatives.

An exemplary recombinant adenoviral vector Ad-RTS-hIL-12 has been produced in the following manner. The coding sequences for the receptor fusion proteins, VP16-RXR and Gal4-EcR separated by the EMCV-IRES (internal ribosome entry site), are inserted into the adenoviral shuttle vector under the control of the human ubiquitin C promoter (constitutive promoter). Subsequently, the coding sequences for the p40 and p35 subunits of hIL-12 separated by IRES, placed under the control of a synthetic inducible promoter containing 6 copies of Gal4-binding site are inserted upstream of the ubiquitin C promoter and the receptor sequences. The shuttle vector contains the adenovirus serotype 5 sequences from the left end to map unit 16 (mu16), from which the E1 sequences are deleted and replaced by the RTS and IL-12 sequences (RTS-hIL-12). The shuttle vector carrying the RTS-hIL-12 is tested by transient transfection in HT-1080 cells for Activator Drug-dependent IL-12 expression. The shuttle vector is then recombined with the adenoviral backbone by cotransfection into HEK 293 cells to obtain recombinant adenovirus Ad-RTS-hIL-12. The adenoviral backbone contains sequence deletions of mu 0 to 9.2 at the left end of the genome and the E3 gene. The shuttle vector and the adenoviral backbone contain the overlapping sequence from mu9.2 to mu16 that allows the recombination between them and production of the recombinant adenoviral vector. Since the recombinant adenoviral vector is deficient in the E1 and E3 regions, the virus is replication-deficient in normal mammalian cells. However, the virus can replicate in HEK 293 cells that harbor the adenovirus-5 E1 region and hence provide the E1 function in trans.

An exemplary recombinant adenoviral vector has been produced in the following manner: The linearized shuttle vector carrying the DNA elements for inducible expression of human IL12, and the adenoviral backbone are co-transfected into HEK293 cells. Recombination between the overlapping sequences on the shuttle vector and the viral backbone results in the production of recombinant adenovirus and is packaged into viral particles in the HEK293 cells. The HEK293 cells are grown in DMEM containing fetal bovine serum.

The virus used for the proposed study was purified by CsCl density gradient centrifugation. The recombinant adenovirus undergoes two rounds of plaque purification and the resulting seed stock is used to produce a master viral bank (MVB) by amplification in HEK293 cells from a fully characterized master cell bank. The MVB undergoes extensive cGMP/GLP release tests including replication competent adenovirus (RCA), sterility, mycoplasma, adventitious viruses, retrovirus, human viruses HIV1/2, HTLV1/2, HAV, HBV, HCV, EBV, B19, CMV, 7 and 8, bovine and porcine virus, complete vector sequencing and functional testing by AD-induced IL12 expression in human cell lines.

The virus from MVB may be used for production of the purified virus in a cGMP facility and may again undergo release tests including identity, RCA, sterility, mycoplasma, adventitious viruses, viral particle-to-infectious units ratio, contamination of host cell DNA, endotoxin and proteins and functional testing by AD-induced IL12 expression in human cell lines.

6.2. Transduction of Autologous Dendritic Cells by Adenovirus Containing hIL-12 Transgene and RheoSwitch® Therapeutic System (RTS)

Dendritic cells derived from the human subjects are transduced ex vivo and injected into the tumor. The DC will be characterized before viral transduction for viability, purity (typically >80% cells showing DC phenotype), sterility, mycoplasma and endotoxin. After viral transduction, the cells are washed repeatedly to remove any unabsorbed virus. Supernatant from the last wash will be tested for the content of residual virus by PCR. Since the DCs are transduced ex vivo by adenoviral vector (non-integrating virus) and the life span of DCs after intratumoral injection and the subsequent migration to draining lymph nodes is short, it is not expected that the viral DNA will be incorporated into any non-target cells. The protocol used for adenoviral transduction of DCs is expected to yield 80-90% transduction and is considered very efficient.

Harvesting of PBMC by Leukapheresis: Subjects undergo a standard 90 to 120 minutes leukapheresis at the Apheresis Unit of the UPCI Outpatient. The leukapheresis procedure involves the removal of blood from a vein in one arm; the passage of blood through a centrifuge (cell separator), where its components are separated and one or more components are removed; and the return of the remaining components to the subject's vein in the same or other arm. No more than 15% of the subject's total blood volume is withdrawn at any one time as blood is processed through the cell separator device. In the cell separator, blood is separated into plasma, platelets, white cells and red blood cells. White blood cells (WBC) are removed and all the other components are returned into the subject's circulation. Every attempt is made to use two peripheral IV lines for this procedure. If that is not possible, a central line may be necessary. The subject has to be cleared by physician to undergo leukapheresis, and is routinely screened for vital signs (including blood pressure) prior to the procedure.

Processing: After collection, the leukapack is delivered by hand to the CPL, and is immediately processed by centrifugal elutriation in ELUTRAT™. This is a closed system validated for clinical use. The monocyte fraction is recovered, and after the recovery and viability of cells are established, they are transferred to an Aastrom cartridge for 6-day culture in the presence of IL-4 and GM-CSF. All processing and washing procedures are performed under sterile conditions.

Initial Plating: Monocytes recovered from a single leukapack are counted in the presence of a trypan blue dye to determine the number of viable cells. Monocytes are evaluated for purity by flow cytometry. Monocytes are resuspended at 5 to $10 \times 10^6$ cells/mL in serum-free and antibiotic-free CellGenix medium, containing 1,000 TU/mL of IL-4 and 1,000 IU/mL of GM-CSF per SOP-CPL-0166, and placed in an Aastrom cartridge. A minimum loading volume of 50 ml and a minimum cell number are required for cassette inoculation.

Culture: The Aastrom cartridge is placed in the incubator in the Replicell System, a fully closed, cGMP-compatible automated culture device for immature DC generation.

Immature DC Harvest: On day 6, the Aastrom cartridge is removed from the incubator and immature DCs are harvested. The cells are recovered by centrifugation at 1,500 rpm, washed in CellGenix medium, counted in the presence of a trypan blue dye and checked for morphologic and phenotypic characteristics.

Viability: This is determined by performing hemocytometer cell counts in the presence of trypan blue. Generally, >95% of harvested cells are viable, i.e., exclude a trypan blue dye. If viability is less than 70% the immature DCs will be discarded.

Phenotyping: The cells generated in culture are counted by microscopic observation on a hemocytometer, and a preliminary differential count (DC vs. lymphocytes) is obtained using a trypan blue dye. Confirmation of the differential count is made by flow cytometry, gating on DC vs. lymphocytes and using high forward and side scatter properties of immature DC as the criterion for their identification. Immature DCs routinely contain >80% of cells with dendritic cell morphology and have DC phenotype.

IL-12p70 Potency Assay: It has been established that mature DCs (mDCs) have the ability to produce IL-12p70 spontaneously or upon activation with CD40L with or without addition of innate immunity signals (e.g., LPS). A standardized IL-12p70 production assay was recently established and is applicable to small samples or large lots of DC vaccines generated under a variety of conditions. The current potency assay consists of two distinct steps, the first involving co-incubation of responder DCs with J588 lymphoma cells stably transfected with the human CD40 ligand gene as stimulators. The second step involves testing of supernatants from these co-cultures for levels of IL-12p70 secreted by DCs stimulated with J558/CD40L+/−LPS in the Luminex system. This potency assay has an inter-assay CV of 18.5% (n=30) and a broad dynamic range, which facilitates evaluation of various DC products characterized by vastly different levels of IL-12p70 production. The normal range for the assay established using DC products generated from monocytes of 13 normal donors was 8-999 pg/mL, with a mean of 270 pg/mL Production and Release Criteria for Dendritic Cells Each lot of the in vitro generated dendritic cells is tested for the presence of microbial contaminants (aerobic and anaerobic bacteria, fungi and mycoplasma), as well as endotoxin and are phenotypically and functionally characterized. All dendritic cells to be injected into subjects will be fresh and will not undergo cryopreservation.

Quality Assurance Testing of DC: DC generated as described above are evaluated for sterility, viability, purity, potency and stability. Criteria for release of the cellular product are established and rigorously followed.

Viability: The cells generated in culture are counted by microscopic observation on a hemacytometer, and a differential count (DC vs. lymphocytes) is obtained using a trypan blue dye. This count provides the percentage of viable cells in the tested culture. More than 70% cell viability by trypan blue exclusion and minimum 70% cells expressing HLA-DR and CD86 as the monocyte-derived DC markers are required for passing the release criteria. Additional markers may be included for exploratory analysis such as CD83 and CCR7 for assessing the DC maturation status, and CD3 and CD19 to assess the lymphocytes contamination.

Purity: Two-color flow cytometry analysis of cells stained with FITC- and PE-conjugated mAbs is used to determine that the DC population identified morphologicallly expresses the surface antigens defined for DC and lack the monocyte and T and B cell lineage antigens. For vaccine preparation, the DC generated must express HLA-DR and CD86 and must not express CD3, CD19, or CD14. To be considered as mDC, the cells must express CD83+ and CCR7+.

Potency: To define a measure of potency for the DC, we determined their ability to produce IL-12p70 as described above.

Sterility: DC are tested by bacterial (Aerobic and anaerobic) and fungal cultures using the BD Bactec system (Becton Dickinson Co., Sparks, Md.) at the University of Pittsburgh Medical Center Microbiology Laboratory. Final results of the microbial cultures are available in 14 days. Prior to release of the DC for vaccine use, a gram stain is performed and must be negative for the presence of microorganisms.

The IMCPL tests for mycoplasma by the use of the Gen-Probe Mycoplasma Tissue Culture Rapid Detection System (Gen-Probe, Inc. San Diego, Calif.), which is based on nucleic acid hybridization technology. Endotoxin testing is performed using the Limulus Amoebocyte Lysate Pyrogen Plus assay (Bio Whittaker, Inc., Walkerville, Md.). Endotoxin testing is performed on the cell culture at the time of harvest and prior to release of the final product. The acceptable endotoxin level is <5 EU/kg body weight. Untransduced and transduced dendritic cells will be cryopreserved for future analysis.

It is expected that all the transduced cells will express the transgene. More than 80% of the DCs are expected to be transduced. The product will be biologically active since the native coding sequence is maintained in the transgene. The viral-transduced DCs injected into the tumor are of immature DC phenotype and do not express IL-12 till they undergo maturation, and hence at this stage, the IL-12 expression is mostly from the transgene. Since the expression of the IL-12 transgene is induced by the small molecule activator drug RG-115932 in a dose dependent way, we can control the level of transgene expression in the transduced DCs to the desired levels. A small portion of the transduced DCs prepared for administration to the human subjects may be tested in vitro for the activator drug-dependent induction of IL12 expression. IL-12 expression may be assayed by ELISA with a sensitivity of 4 ng/ml.

The in vivo mouse tumor model is similar to the human studies in that mice bearing subcutaneous melanoma (B16) tumor were treated in the same way as the proposed human study by the injection of adenoviral transduced DCs and induction of murine 11,12 transgene. After tumor regression was observed, rechallenge with the same tumor cells did not result in tumor growth, indicating systemic tumor immunity.

It is expected that in vitro induction of IL-12 from cells transduced by the vector used in the proposed study yields about 500 ng IL-12 per $10^6$ cells in 24 hours, determined by ELISA. In preclinical studies using mouse model of melanoma, intratumoral injection of $10^6$ or more transduced DCs showed efficacy. However, it is expected that the required intratumoral injection may show efficacy at levels below this amount and therefore injections of $5 \times 10^7$ transduced DCs may be utilized as a starting point to determine if less or greater amounts are required.

For instance, in vitro, human and mouse cell lines and primary dendritic cells transduced with recombinant adenoviral vector carrying the genes for IL12 show induction of IL12 expression in response to the activator drug in a dose dependent way.

Adenoviral transduction of human DCs at different MOI and for different duration of viral adsorption showed efficient transduction of these cells by 3 hour viral adsorption at MOI of 500. The activator drug induced IL-12 expression in these transduced human DCs (FIG. 9).

For in vivo experiments on a mouse melanoma model described above, C57/BL6 mice were given subcutaneous injections of B16 cells to form tumors. Intratumoral injection of DCs transduced with adenoviral vector carrying the murine IL-12 genes under the control of the RTS, along with administration of the activator drug resulted in systemic immunity specific to the tumor. The treatment resulted in tumor regression. Rechallenge of the cured mice after 50 days with B16 cells showed that the B16 cells did not form tumors. This induction of tumor immunity was dependent on the administration of the activator drug, and hence IL-12 expression, in the transduced DCs injected. The activator drug was effective in intraperitoneal and oral routes. See FIG. 11 and FIG. 14.

6.3. Formulation of Activator Drug

The activator drug used herein is formulated in any one of the following formulations:
(1) 100% Labrasol;
(2) Listerine flavored Labrasol (Latitude Pharmaceuticals Inc., USA) comprising (a) menthol, (b) thymol, (c) eucalyptol, (d) aspartame, (e) sodium saccharine, (f) citric acid, (g) peppermint flavor, (h) cream flavor, (i) labrasol;
(3) Miglyol 812 and phospholipon 90G (Latitude Pharmaceuticals Inc., USA); or
(4) Miglyol 812, phospholipon 90G and Vitamin E tocopheryl polyethylene glycol succinate (Latitude Pharmaceuticals Inc., USA).

6.4. Delivery

While a variety of concentrations and specific protocols may be imagined, one example for treating patients would include patients receiving intratumoral injection(s) of transduced autologous dendritic cells (AdDCs) at a concentration of $5 \times 10^7$ suspended in sterile saline engineered to express hIL-12 (human interleukin 12) under control of the RTS in combination with the oral activator drug (RG-115932).

6.4.1. Initial Treatment

Day 1 Inpatient Visit: On day 1, a baseline physical examination (including vital signs, weight, and ECOG status) is performed. Urine is collected and blood drawn for baseline serum chemistry, urinanalysis, and hematology (safety profile). Approximately 3 hours before the intratumoral injection of the in vitro engineered dendritic cells, each subject is dosed with an activator drug (cohort 1-0.01 mg/kg, 0.3 mg/kg, 1.0 mg/kg, and 3 mg/kg) immediately after a meal. Blood is drawn at specified time intervals (predose, 0.5, 1, 1.5, 2, 4, 6, 8, 12, 16, and 24 hours after the AD dose) on day 1 for evaluation of single dose pharmacokinetics of the activator drug and its major metabolites. Each subject receives a single intratumoral injection of adenoviral transduced autologous dendritic cells at a concentration of $5 \times 10^7$ cells, engineered to express hIL-12 under the control of the RTS. The subjects are carefully monitored for local injection site reactions and/or hypersensitivity reactions. Day 2 through 14 Inpatient Visit: On days 2 through 14, each subject is dosed with the activator drug immediately after a meal. Vital signs and adverse events are collected daily on days 2 through 14. On day 4±24 hours, biopsies of the tumor and/or draining lymph nodes are removed from approximately 50% of the subjects for measurement of hIL-12 and cellular immune response. On day 8, weight is measured. On day 8±24 hours, biopsies of the tumor and/or draining lymph nodes are removed from subjects who did not have a biopsy performed on day 4 for measurement of hIL-12 and cellular immune response. Blood is drawn on day 4±24 hours and day 8±24 hours for assay of potential antibodies and cellular immune response against the adenovirus and/or the RTS components. A serum cytokine profile is also obtained to determine if the expression of other cytokines is affected by treatment with the hIL-12 transgene. On day 8, urine is collected and blood is drawn for baseline serum chemistry, urine analysis, and hematology (safety profile). On Day 8, blood is drawn at specified time intervals (predose, 0.5, 1, 2, 4, 6, 8, 12, 16, and 24 hours after the AD dose) for evaluation of steady-state pharmacokinetics/ADME of the activator drug and its major metabolites.

Day 14 Inpatient Visit: On day 14, each subject is dosed with the Activator Drug immediately after a meal. Each subject receives a physical examination (including vital signs, height, weight and ECOG status). Urine is collected and blood is drawn for serum chemistry, urinalysis, and hematology (safety profile). Blood is drawn on day 14±24 hours for assay of potential antibodies and cellular immune response against the adenovirus and/or the RTS components. A serum cytokine profile is also obtained to determine if the expression of other cytokines is affected.

Blood is collected from the subjects at specified inpatient and outpatient visits to measure potential antibodies and cellular immune response to the adenovirus and components of the RTS. Blood is obtained for a baseline serum cytokine profile. The AdVeGFP infectivity blocking type assay is used to detect an antibody response to the adenoviral vector (Gambotto, Robins et al. 2004). Antibody response to the RTS components will be assessed by western blot and/or ELISA using serum from the patient and the RTS proteins produced from an expression vector. In addition, multiplex cytokine testing will be done in the serum by Luminex for IL-12, IFN-gamma, IP-10, and other Th1/Th2 cytokines such as IL-2, TNF-alpha, IL-4, IL-5, and IL-10. These antibody and cytokine assays will need about 10 ml of blood.

The cellular immune response assays use about 50-60 ml blood and CD4 and CD8 T cell subsets are separated from it. The separated T cells are mixed with autologous DCs transduced with empty AdV vector, AdV-RTS, or AdV-RTS-hIL12 vectors in an ELISPOT assay for INF-gamma production by the T cells activated by the AdV- and RTS-derived antigens, if any. Similar assays are performed using the tumor cells as such and/or DCs expressing shared melanoma antigens to assess the early response to the tumor. Additional assays are also performed as necessary.

On day 14±24 hours, biopsies of the tumor and/or draining lymph nodes are removed from all subjects that have tissue available for measurement of hIL-12 and cellular immune response. Adverse events are recorded. After completion of the day 14 procedures, each subject are discharged from the inpatient clinic and asked to return in approximately 3 weeks for the 1 month follow-up outpatient visit.

Early Termination Visit: If a subject cannot complete the inpatient treatment phase, the following early termination visit procedures will be conducted prior to discharge from the clinic. Each subject receives a physical examination (including vital signs, height, weight and ECOG status). Urine is collected and blood is drawn for serum chemistry, urinalysis, and hematology (safety profile). Blood will be drawn for assay of potential antibodies and cellular immune response against the adenovirus and/or the RTS components as described above. A serum cytokine profile will also be obtained as described above to determine if the expression of other cytokines is affected. Biopsies of the tumor and/or draining lymph nodes are removed from all subjects that have tissue available for measurement of hIL-12 and cellular immune response. Adverse events are recorded. After completion of the early termination visit procedures, each subject is discharged from the inpatient clinic and asked to return in approximately 3 weeks for the 1 month follow-up outpatient visit.

Month 1 Through 4 Follow-Up Visits: Adverse events will be collected during the month 1 through 4 follow-up period. At the month 1, 2, and 3 visits, follow-up physical examinations (including vital signs, weight and ECOG status) will be conducted. Urine and blood will be collected at the month 1, 2, and 3 visits for serum chemistry, urinalysis, and hematology (safety profile). Blood will be collected at the month 1 and 3 visit for assay of potential antibodies and cellular immune response against the adenovirus and/or the RTS components. Blood will be obtained at the month 1 visit for serum cytokine profiling. At the month 1 visit, biopsies of the tumor and/or draining lymph nodes will be performed on subjects with available tissue, for measurement of hIL-12 and cellular immune response. CT/PET scans will be performed at the month 2 and 4 visits to assess overall disease progression or regression.

Month 5 Through 6 Follow-Up Visits: If drug-related toxicity is observed at month 3 or month 4, month 5 through month 6 follow-up visits will be conducted. Adverse events will be collected during the month 5 through month 6 follow-up period. Subject safety will be monitored by a telephone call from clinic personnel to each subject during month 5 and through an outpatient visit at month 6. Should a drug-related toxicity occur or continue through month 5 and be deemed by the investigator to be serious, not stabilized, or warrant further evaluation; clinic personnel will not only telephone the subject but will ask that the subject visit the clinic. At the month 6 visit, follow-up physical examinations (including vital signs, weight and ECOG status) will be conducted. Urine and blood will be collected for serum chemistry, urinalysis, and hematology (safety profile). Blood will also be collected at the month 6 visit for assay of potential antibodies and cellular immune response against the adenovirus and/or the RTS components. CT/PET scans will be performed at the month 6 visit to assess overall disease progression or regression.

Activator Drug Dosing & Stopping Criteria: If a dose-limiting toxicity (DLTs; i.e., a total of >2 of 3 subjects enrolled in a group in cohort 1 experience a >grade 3 toxicity according to CTCAE v3.0) is determined, at a given dose level the next group of 3 subjects will be administered the same dose level of Activator Drug. If DLT are observed in 1 or more subjects in the additional dose group, dose escalation will be discontinued and the next lower dose is considered maximum tolerated dose (MTD), otherwise dose escalation resumes until MTD is reached or to a maximum dose of 10 mg/kg (whichever occurs first).

Safety, tolerance, and transgene function will be assessed for all subjects in each group of cohort 1 up to one month after injection of AdDCs before enrolling subjects to receive the next highest dose of Activator Drug.

If a subject experiences a >grade 3 toxicity according to CTCAE v3.0 that is deemed possibly, probably or definitely related to study drug treatment, dosing with the Activator Drug will be discontinued for that subject and the subject will undergo early termination visit procedures.

Study Stopping Criteria: If >70% of subjects in a cohort experience a >grade 3 toxicity according to CTCAE v3.0 that is deemed probably or definitely related to study drug treatment, dosing with the Activator Drug will be discontinued for all subjects and all subjects will undergo early termination visit procedures.

Investigational Trial Medication: A combination of two investigational medications will be evaluated for safety, tolerance, transgene function, and immunological effects in this trial. The small molecule Activator Drug will be administered as an oral solution at doses of 0.01 mg/kg, 0.1 mg/kg, 1.0 mg/kg and 10.0 mg/kg to subjects with Stage III or IV melanoma once daily for fourteen consecutive days in combination with a single intratumoral injection of adenoviral transduced autologous dendritic cells at a concentration of $5 \times 10^7$, engineered to express hIL-12. There is an option for subjects to receive an additional intratumoral injection of AdDCs in combination with treatment for 14 consecutive days with the Activator Drug.

6.5. Assessment of Safety to Assessment of Transgene Function and Immunological Effects Endotoxin testing is performed on the cell culture at the time of harvest and prior to release of the final product. The acceptable endotoxin level is <5 EU/kg body weight. Untransduced and transduced dendritic cells will be cryopreserved for future analysis.

Assessment of Safety: The safety of a single intratumoral injection of adenoviral transduced autologous dendritic cells in combination with the oral Activator Drug will be evaluated by physical examinations, vital signs, serum chemistry, urinalysis, hematology, adverse events, and antibodies and cellular immune response to adenovirus and components of the RTS during the trial and 12 month follow-up. Pregnancy tests will be done on females of childbearing potential at screening. A list of concurrent medications will also be obtained from subjects at screening and day 0 of the retreatment period to determine if there is any relationship between concurrent medications and potential adverse events. An approximate total of 89 teaspoons (439 ml) of blood plus leukapheresis will be collected from subjects during the screening phase and initial inpatient treatment phase (26 day period). An approximate total of 75 teaspoons (370 ml) of blood plus leukapheresis will be collected from subjects during the inpatient retreatment phase (26 day period, 5-6 weeks from previous inpatient visits). An approximate total of 46 teaspoons (227 ml) of blood will be collected from subjects during the outpatient follow-up phase (Month 1-6).

Physical Examinations: Complete physical examinations (including ECOG performance status) will be conducted at specified inpatient and outpatient visits. Medical history and demographics of each subject will also be recorded at the screening visit.

Vital Signs: Vital signs of each subject will be included in each scheduled physical examination but will also be taken at all inpatient and outpatient visits. Vital signs will include blood pressure, pulse, temperature, and respirations. Weight and height will also he recorded at specified visits. Vital signs (minus height and weight) will be recorded every hour for the first two hours and then every 8 hours after dosing of the Activator Drug has occurred.

Blood Chemistry: A random, non-fasted blood sample will be drawn from each subject at specified inpatient and outpatient visits and serum harvested for chemistry. The following serum tests will be performed: AST (aspartate transaminase), ALT (alanine transaminase), GGT (gamma-glutamyl transpeptidase), LDH (lactic dehydrogenase), LAP (leucine aminopeptidase), alkaline phosphatase, creatinine, total bilirubin, total protein, albumin, blood urea nitrogen, total cholesterol, glucose, and electrolytes.

Urinanalysis: A random, mid-stream urine sample will be collected from each subject at specified inpatient and outpatient visits and is analyzed. The following tests will be performed: description of color and appearance, specific gravity, pH, glucose, ketone bodies, protein, red and white blood cell number, and pyroluria.

Hematology: A random, non-fasted blood sample will be drawn from each subject at specified inpatient and outpatient visits and hematologic tests will be run as follows: complete blood count (CBC) including white blood cell count, differential white blood cell count, red blood cell count, hematocrit, hemoglobin, red blood cell indices, and platelet count. PTT (partial thromboplastin time) and PT (prothrombin time) will also be evaluated.

Adverse Events: The NCI Common Terminology Criteria for Adverse Events (CTCAE version 3.0) will be utilized to evaluate toxicity in the trial and 3-6 month follow-up period. An adverse event/experience is any reaction, side effect, or other untoward event (signs, symptoms, changes in laboratory data) associated with the use of a test article (drug, biologic, or device), whether or not the event is considered related to the test article. A serious adverse event/experience is any adverse event or experience that results in any of the following outcomes: death, a life-threatening adverse experience, a congenital anomaly/birth defect, inpatient hospitalization or prolongation of existing hospitalization, or a persistent or significant disability/incapacity. Important medical events/experiences that may not result in death, be life-threatening, or require hospitalization may be considered serious adverse experiences when, based upon appropriate medical judgment, they may jeopardize the subject or may require medical or surgical intervention to prevent one of the outcomes listed in this definition.

The severity of adverse events will be graded as follows: Grade I (mild), Grade 2 (moderate), Grade 3 (severe), Grade 4 (life-threatening or disabling), Grade 5 (death related to adverse event). The relationship between an adverse event and study medication will be determined on the basis of clinical judgment and the following definitions:

a. definitely related is an adverse event that follows a reasonable temporal sequence from administration of the study medication, follows a known response pattern to the study medication, and, when appropriate to the protocol, is confirmed by improvement after stopping the study medication (positive dechallenge) and by reappearance of the reaction after repeat exposure (positive rechallenge) and cannot be reasonably explained by known characteristics of the subject's clinical state or by other therapies, b. probably related is an adverse event that follows a temporal sequence from administration of the study medication, follows a known response pattern to the study medication and, when appropriate to the protocol, is confirmed by improvement after dechallenge, and cannot be reasonably explained by the known characteristics of the subject's clinical state or by other therapies, c. possibly related is an adverse event that follows a reasonable temporal sequence from administration of the study medication and follows a known response pattern to the study medication but could have been produced by the subject's clinical state or by other therapies, d. unrelated is an adverse event for which sufficient information exists to indicate that the etiology is unrelated to the study medication. Two or more of the following variables apply to an unrelated adverse event: 1. The adverse event does not follow a reasonable temporal sequence after administration of the study medication, 2. The adverse event is readily explained by the subject's clinical state or other therapies, 3. The adverse event does not abate upon dose reduction or cessation of therapy (assuming that it is reasonable to expect abatement of the adverse event within the observed interval).

All observed or reported adverse events subsequent to enrollment of subjects will be recorded. Any condition that is present at time of enrollment that worsens will be recorded as an adverse event. Adverse events will be determined on the basis of volunteered symptoms and clinical observation and assessment at trial visits. At each inpatient and outpatient visit, enrolled subjects will be asked to volunteer information concerning adverse events with non-leading questions such as "How are you feeling?" Changes in laboratory values will be recorded as adverse events if considered clinically significant and if clinical changes or action are required such as initiating a treatment.

Potential Antibody and Cellular Immune Response to Adenovirus and/or Components of the RTS: Blood will be collected from the subjects at specified inpatient and outpatient visits to evaluate the potential antibody and cellular immune response to the adenovirus and components of the RTS and tumor antigens. The AdVeGFP infectivity blocking type assay will be used to detect an antibody response to the adenoviral vector (Nwanegbo, et al. 2004). Antibody response to the RTS components will be assessed by western blot and/or ELISA using serum from the subjects and the RTS proteins produced from an expression vector. In addition, multiplex cytokine testing will be done in the serum by Luminex for IL-12, IFN-gamma, IP-10, and other Th1/Th2 cytokines such as IL-2, TNFa, IL-4, IL-5 and IL-10. These antibody and cytokine assays will need about 10 ml of blood.

The cellular immune response assays use about 50-60 ml blood and CD4 and CD8 T cell subsets will be separated from it. The separated T cells will be mixed with autologous DCs transduced with empty AdV vector, AdV-RTS, or AdV-RTS-hIL12 vectors in an ELISPOT assay for IFN-gamma production by the T cells activated by the AdV- and RTS-derived antigens, if any. Similar assays will be performed using the tumor cells as such and/or DCs expressing shared melanoma antigens to assess the early immune response to the tumor. Additional assays may also be performed as necessary.

PREGNANCY TESTING: Females of childbearing potential is administered a urine pregnancy test at the screening visit and before the first inpatient visit of the retreatment phase. The testing is performed at least 72, 48, 24, or 12 hours prior to the administration of Activator Drug during both the initial treatment and all retreatment periods. If the urine pregnancy test is positive, then confirmation will be obtained with a serum pregnancy test. If pregnancy is confirmed, the subject will not be allowed to enter the trial or continue into the retreatment phase. The pregnancy testing may be reperformed as many as necessary.

CONCOMITANT MEDICATION INQUIRY: At screening, and before the first inpatient visit of the retreatment phase, each subject will be asked to provide a list of concurrent medications to determine any possible relationship to adverse events that occur during the trial and follow-up phase.

RETREATMENT CRITERIA: If a subject has tolerated prior AdDC inoculation without adverse reactions that are limiting, and has shown no progression of disease or symptomatic decline at the time of potential retreatment, they will be considered for retreatment. If, in the opinion of the principal investigator, and treating physician there is a potential clinical benefit for additional intratumoral injection(s) of AdDCs in combination with Activator Drug (maximum tolerated dose from cohort 1) for 14 consecutive days, retreatment will be offered to the subject, provided the following criteria are met:
1. There have been no limiting toxicities,
2. The subject's disease is stable or showing clinical or subjective signs of improvement, and
3. There is no evidence of antibody or cellular immune response to adenovirus components of RheoSwitch® Therapeutic System.

ASSESSMENT OF TRANSGENE FUNCTION AND IMMUNOLOGICAL EFFECTS: Punch or excisional biopsies of the tumor and associated draining lymph nodes will be collected during screening (day −12 to day −7), day 4, day 8 and day 14 of the trial and at month 1 of the follow-up (see Tables 3-5) for in vivo assessment of transgene expression of hIL-12 and cellular immune response. Fine needle aspiration biopsies of the tumor and associated draining lymph nodes will be collected on day −12 to −7 and day 14 of the retreatment period for in vivo assessment of transgene expression of hIL-12 and cellular immune response. Biopsies will be evaluated by standard light microscopy and immunohistochemistry to assess cellular infiltration of T cells into the tumor and draining lymph nodes. Biopsy sections will be read by a pathologist unaware of study subject background. To distinguish between endogenous and induced IL-12 expression by DCs in the tumor and draining lymph nodes, RT-PCR on RNA will be used with appropriately designed primers. Blood will be drawn for a serum cytokine profile at screening, day 4, day 8 and day 14 of the trial, at month 1 of the follow-up and on day −12 to −7, day 8 and day 14 of the retreatment period (see Tables 3-5). A serum cytokine profile will be obtained to determine if the expression of other cytokines is affected by treatment with the hIL-12 transgene. Multiplex cytokine testing will be done in the serum by Luminex for IL-12, IFN-gamma, IP-10, and other Th1/Th2 cytokines such as IL-2, TNFa, IL-4, IL-5 and IL-10. These antibody and cytokine assays will need about 10 ml of blood.

SINGLE DOSE AND STEADY-STATE PHARMACOKINETICS OF ACTIVATOR DRUG: Blood will be drawn at specified time intervals (predose, 0.5, 1, 1.5, 2, 4, 6, 8, 12, 16, and 24 hours after the morning dose) on day 1 of the trial for evaluation of single dose pharmacokinetics and on day 8 of the trial for measurement of steady state pharmacokinetics/ADME of the Activator Drug and its major metabolites. Plasma will be evaluated by HPLC to obtain the following steady-state pharmacokinetic endpoints of the Activator Drug and major metabolites: Cmax (maximum observed plasma concentration), Tmax (time to maximum observed plasma concentration), Ctrough (minimum observed plasma concentration computed as the average of the concentrations at 0 and 24 hours), C24h (plasma concentration at 24 hours), AUC24h (area under plasma concentration-time curve from time 0 to 24 hours), Ke (apparent elimination rate), and T112 (apparent half-life).

It is to be understood that the foregoing described embodiments and exemplifications are not intended to be limiting in any respect to the scope of the invention, and that the claims presented herein are intended to encompass all embodiments and exemplifications whether or not explicitly presented herein.

LITERATURE

Abdi K., et al. (2006). T-cell control of IL-12p75 production. *Scand J Immunol* 64: 83-92.

Adorini, L. (1999). Interleukin-12, a key cytokine in Th1-mediated autoimmune diseases. *Cell Mol Life Sci* 55: 1610-25.

Adorini, L., (2001). Interleukin 12 and autoimmune diabetes. *Nat Genet* 27: 131-2.

Adorini, L., et al. (2002). Understanding autoimmune diabetes: insights from mouse models. *Trends Mol Med* 8: 31-8.

Adorini, L., et al. (1996). The role of IL-12 in the pathogenesis of Th1 cell-mediated autoimmune diseases. *Ann NY Acad Sci* 795: 208-15.

Akhtar, N., et al. (2004). Interleukin-12 inhibits tumor growth in a novel angiogenesis canine hemangiosarcoma xenograft model. *Neoplasia* 6: 106-16.

Akiyama, Y., et al. (2000). Enhancement of antitumor immunity against B16 melanoma tumor using genetically modified dendritic cells to produce cytokines. *Gene Ther* 7: 2113-21.

Al-Mohanna, F., et al. (2002). IL-12-dependent nuclear factor-kappaB activation leads to de novo synthesis and release of IL-8 and TNF-alpha in human neutrophils. *J Leukoc Biol* 72: 995-1002.

Aliberti, J. C., et al. (1996). Interleukin-12 mediates resistance to *Trypanosoma cruzi* in mice and is produced by murine macrophages in response to live trypomastigotes. *Infect Immun* 64: 1961-7.

Allavena, P., et al. (1994). Interleukin-12 is chemotactic for natural killer cells and stimulates their interaction with vascular endothelium. *Blood* 84: 2261-8.

Alli, R. S. and Khar, A. (2004). Interleukin-12 secreted by mature dendritic cells mediates activation of NK cell function. *FEBS Lett* 559: 71-6.

Alzona, M., et al. (1996). Interleukin-12 activates interferon-gamma production by targeted activation of CD30+ T cells. *Ann NY Acad Sci* 795: 127-36.

Amemiya, K., et al. (2006). Interleukin-12 induces a Th1-like response to *Burkholderia mallei* and limited protection in BALB/c mice. *Vaccine* 24: 1413-20.

Anderson, R. D., et al. (2000). Ad-RTS-hIL-1. A simple method for the rapid generation of recombinant adenovirus vectors. *Gene Therapy,* 4, 1034-1038.

Araujo, M. I., et al. (2001). Interleukin-12 promotes pathologic liver changes and death in mice coinfected with *Schistosoma mansoni* and *Toxoplasma gondii*. *Infect Immun* 69: 1454-62.

Arthur, F. F., et al. (1997). A comparison of gene transfer methods in human dendritic cells. *Cancer Gene Therapy*, 4, 17-25.

Arulanandam, B. P., et al. (1999). IL-12 is a potent neonatal vaccine adjuvant. *Eur J Immunol* 29: 256-64.

Athie, M. V., et al. (2000). IL-12 selectively regulates STAT4 via phosphatidylinositol 3-kinase and Ras-independent signal transduction pathways. *Eur J Immunol* 30: 1425-34.

Athie-Morales, V., et al. (2004). Sustained IL-12 signaling is required for Th1 development. *J Immunol* 172: 61-9.

Atkins, M. B., et al. (1999). High-dose recombinant interleukin 2 therapy for patients with metastatic melanoma: analysis of 270 patients treated between 1985 and 1993. *J Clin Oncol;* 17: 2105-2116.

Atkins, M. B., et al. (1997). Phase I evaluation of intravenous recombinant human interleukin 12 in patients with advanced malignancies. *Clin Cancer Res* 3: 409-17.

Balch, C. M., et al. (2001). Final version of the american, joint committee on cancer staging system for cutaneous melanoma. *Journal of Clinical Oncology*, 19: 3635-3648, 2001.

Berard, F., et al. (2000). Cross-priming of naive CD8 T cells against melanoma antigens using dendritic cells loaded with killed allogeneic melanoma cells. *J Exp Med* 192: 1535-44.

Bertagnolli, M. M., et al. (1992). IL-12 augments antigen-dependent proliferation of activated T lymphocytes. *J Immunol* 149: 3778-83.

Bhardwaj, N., et al. (1996). IL-12 in conjunction with dendritic cells enhances antiviral CD8+ CTL responses in vitro. *J Clin Invest* 98: 715-22.

Biedermann, T., et al. (2006). IL-12 instructs skin homing of human Th2 cells. *J Immunol* 177: 3763-70.

Brunda, M. J, and Gately, M. K. (1994). Antitumor activity of interleukin-12. *Clin Immunol immunopathol* 71: 253-5.

Buchanan, J. M., et al. (1995). Interleukin 12 alters the isotype-restricted antibody response of mice to hen eggwhite lysozyme. *Int Immunol* 7: 1519-28.

Butterfield, L., et al. (2003). Determinant spreading associated with clinical response in dendritic cell-based immunotherapy for malignant melanoma. *Clinical Cancer Research*, 9, 998-1008.

Cella M., et al., (1999) Maturation, Activation, and Protection of Dendritic Cells Induced by Double stranded RNA. *J. Exp. Med.* 189, 821-829.

Chada, S., et al. (2003). Cytokine- and chemokine-based gene therapy for cancer. Curr Opin Mot Ther, 5: 463-474.

Faure, F., et al. (1998). Tumor-specific immune response: current in vitro analyses may not reflect the in vivo immune status. *Crit Rev Immunol* 18: 77-86.

Gambotto, Robins et al. 2004

Gilboa, E. (2007). DC-based Clinical Vaccines. *J. Clinic. Invest.* 117: 1195-1203.

Gogas, H., et al. (2006). Prognostic significance of autoimmunity during treatment of melanoma with interferon. *New England Journal of Medicine*, 354, 709-718.

Heinzerling, L., et al. (2005). Intratumoral injection of DNA encoding human interleukin 12 into patients with metastatic melanoma: clinical efficacy. *Hum Gene Ther* 16: 35-48.

Itoh, T., et al. (1994). Partial purification of murine tumor-associated peptide epitopes common to histologically distinct tumors, melanoma and sarcoma, that are presented by H-2 Kb molecules and recognized by CD8+ tumor-infiltrating lymphocytes. *J Immunol* 153: 1202-15.

Kaka, K. S., et al. (2008). Using Dendritic Cell Maturation and IL-12 PRoducing Capacity as Markers of Function; A Cautionary Tale. *J. Immunother,* 31 (4): 359-

Kalinski, P., et al. (2005). Natural killer-dendritic cell cross-talk in cancer immunotherapy. *Expert Opinion Biological Therapy*, 1303-1315.

Kang, W. K., et al. (2001). Interleukin 12 gene therapy of cancer by peritumoral injection of transduced autologous fibroblasts: outcome of a phase I study. *Hum Gene Ther* 12: 671-84.

Karzenowski, D., et al. (2005). Inducible control of transgene expression with ecdysone receptor: gene switches with high sensitivity, robust expression, and reduced size. *Biotechniques* 39, 191-192.

Kikuchi, T. (2006). Genetically modified dendritic cells for therapeutic immunity. *Journal of Experimental Medicine*, 208, 1-8.

Kumar, P., and Katakam. A. (2007). RheoSwitch® System: a highly sensitive ecdysone receptor-based gene regulation system induced by synthetic small-molecule ligands. In Gene Transfer: Delivery and Expression of DNA and RNA b Ed. Friedmann, T. and Rossi, J., Cold Spring Harbor Laboratory Press, 643-651.

Liu, Y., et al. (2002). In situ adenoviral interleukin 12 gene transfer confers potent and long-lasting cytotoxic in glioma. *Cancer Gene Therapy*, 9, 9-15.

Mazzolini, G., et al. (2005). Intratumoral injection of dendritic cells engineered to secrete interleukin-12 by recombinant adenovirus in patients with metastic gastrointestinal carcinomas. *Journal of Clinical Oncology*, 23, 999-1010.

Murphy, A., et al. (2005). Gene modification strategies to induce tumor immunity. *Immunity,* 22, 409-414.

Nagayama, H., et al. (2000). IL-12 Responsiveness and Expression of IL-12 Receptor in Human Peripheral Blood Monocyte-derived Dendritic Cells. *J. Immunol.* 165: 59-66.

Nwanegbo E., et al. (2004). Prevalence of neutralizing antibodies to adenoviral serotypes 5 and 35 in the adult populations of The Gambia, South Africa, and the United States. *Clinical Diagnostic Lab Immunology*. March, 11(2), 351-357.

Palli, S. R., et al. (2003). Improved ecdysone receptor-based inducible gene regulation system. *European Journal of Biochemistry*, 270, 1308-1315.

Philpott, N. J., et al. (2004). Adenovirus-induced maturation of Dendritic Cells through a PI3 kinase-mediated TNF-alpha induction pathway. *PNAS* 101, 6200-6205.

Ranieri, E., et al. (1999). Dendritic cells transduced with an adenovirus vector encoding epstein-barr virus latent membrane protein 2B: a new modality for vaccination. *Journal of Virology*, 73, 10416-10425.

Ribas, A., et al. (2002). Cancer immunotherapy using gene-modified dendritic cells. *Cancer Gene Therapy*, 2, 57-78.

Romani, N., et al. (1994). Proliferating dendritic cell progenitors in human blood. *Journal of Experimental Medicine,* 180, 83-93.

Romani L, et al. (1997). Interleukin-12 in infectious diseases. *Clin Microbiol Rev* 10: 611-36.

Rothe, H., et al. (1996). Interleukin-12 gene expression mediates the accelerating effect of cyclophosphamide in autoimmune disease. *Ann NY Acad Sci* 795: 397-9.

Sangro, B., et al. (2004). Phase I trial of intratumoral injection of an adenovirus encoding interleukin-12 for advanced digestive tumors. *J Clin Oncol* 22: 1389-97.

Sangro, B., et al. (2005). Gene therapy of cancer based on interleukin 12. *Curr Gene Ther* 5: 573-81.

Satoh, Y., et al. (2002). Local administration of IL-12-transfected dendritic cells induces antitumor immune responses to colon adenocarcinoma in the liver in mice. *J Exp Ther Oncol* 2: 337-49.

Satoskar, A. R., et al. (2000). IL-12 gene-deficient C57BL/6 mice are susceptible to *Leishmania donovani* but have diminished hepatic immunopathology. *Eur J Immunol* 30: 834-9.

Schopf, L. R., et al. (1999). Interleukin-12 is capable of generating an antigen-specific Th1-type response in the presence of an ongoing infection-driven Th2-type response. *Infect Immun* 67: 2166-71.

Spatz, M., et al., (2000). Immune response to the Herpes Simplex Type I regulatory Proteins ICP8 and VP16 in Infected Persons. *J. Med. Virol.* 62, 29-36.

Svane, I. M., et al. (1999). The role of cytotoxic T-lymphocytes in the prevention and immune surveillance of tumors—lessons from normal and immunodeficient mice. *Med Oncol* 16: 223-38.

Tang, H. L. and Cyster, J. G., (1999). Chemokine up-regulation and activated T cell attraction by maturing dendritic cells. *Science*, 284, 819-822.

Tatsumi, T., et al. (2003). Intratumoral delivery of dendritic cells engineered to secrete both interleukin (IL)-12 and IL-18 effectively treats local and distant disease in association with broadly reactive Tc1-type immunity. *Cancer Res* 63: 6378-86.

Thomas, G. R., et al. (2000). IL-12- and IL-2-induced tumor regression in a new murine model of oral squamous-cell carcinoma is promoted by expression of the CD80 co-stimulatory molecule and interferon-gamma. *Int J Cancer* 86: 368-74.

Trinchieri, G. (2003). Interleukin-12 and the regulation of innate resistance and adaptive immunity. *Nat Rev Immunol* 3: 133-46.

Triozzi, P. L., et al. (2005). Phase I study of the intratumoral administration of recombinant canarypox viruses expressing B7.1 and interleukin 12 in patients with metastatic melanoma. *Clin Cancer Res* 11: 4168-75.

Tsugawa, T., et al. (2004). Sequential delivery of interferon-gene and DCs to intracranial gliomas promotes an effective anti-tumor response. *Gene Therapy*, 11, 1551-1558.

Tsung, K., et al. (1997). IL-12 induces T helper 1-directed antitumor response. *J Immunol* 158: 3359-65.

Vujanovic, L., et al. (2006). IL-12p70 and IL-18 gene-modified dendritic cells loaded with tumor antigen-derived peptides o recombinant protein effectively stimulate specific Type-1 CD4(+) T-cell responses from normal donors and melanoma patients in vitro. *Cancer Gene Therapy*, 13, 798-805.

Wigginton, J. M. and Wiltrout, R. H. (2002). IL-12/IL-2 combination cytokine therapy for solid tumours: translation from bench to bedside. *Expert Opin Biol Ther*, 2: 513-524.

Wolf, S. F., et al. (1994). Interleukin 12: a key modulator of immune function. *Stem Cells* 12: 154-68.

Yamanaka, R., et al. (2002). Marked enhancement of antitumor immune responses in mouse brain tumor models by genetically modified dendritic cells producing Semliki Forest virus-mediated interleukin-12. *J Neurosurg* 97: 611-8.

Yuminamochi, E., et al. (2007). Interleukin-12- and interferon-gamma-mediated natural killer cell activation by *Agaricus blazei* Murill. *Immunology*.

What is claimed is:

1. In vitro engineered dendritic cells for prevention of tumor progression in a mammal, the cells comprising a vector comprising a polynucleotide sequence at least 95% identical to SEQ ID NO:13, wherein the polynucleotide sequence encodes a gene switch, said gene switch comprising:

(1) (a) a first transcription factor sequence encoding a VP-16 transactivation domain and a chimeric RXR ligand binding domain, and (b) a second transcription factor sequence encoding a GAL4 DNA-binding domain and a *Choristoneura fumiferana* ligand binding domain comprising a substitution mutation, wherein the protein encoded by the first transcription factor sequence and the protein encoded by the second transcription factor sequence interact to form a ligand-dependent transcription factor complex, and (2) a first polynucleotide encoding a polypeptide at least 85% identical to SEQ ID NO: 7, and a second polynucleotide encoding a polypeptide at least 85% identical to SEQ ID NO: 8, the first and second polynucleotides operably linked to a promoter and response element which are activated by said ligand-dependent transcription factor complex, wherein the response element comprises a GAL4-binding site.

2. The in vitro engineered dendritic cells of claim 1, wherein the polynucleotide sequence is 100% identical to SEQ ID NO:13.

3. A pharmaceutical composition comprising the in vitro engineered dendritic cells of claim 1.

4. A kit comprising the in vitro engineered dendritic cells of claim 1.

5. The in vitro engineered dendritic cells of claim 1, wherein said dendritic cells are human dendritic cells.

6. The in vitro engineered dendritic cells of claim 1, wherein said dendritic cells are autologous dendritic cells.

7. The in vitro engineered dendritic cells of claim 1, wherein said dendritic cells are bone marrow dendritic cells.

* * * * *

SEQUENCE LISTING

```
<160> NUMBER OF SEQ ID NOS: 13

<210> SEQ ID NO 1
<211> LENGTH: 648
<212> TYPE: DNA
<213> ORGANISM: Mus sp.
<220> FEATURE:
<223> OTHER INFORMATION: IL-12 p35

<400> SEQUENCE: 1
atgtgtcaat cacgctacct cctcttttg gccaccttg ccctcctaaa ccacctcagt      60
ttggccaggg tcattccagt ctctggacct gccaggtgtc ttagccagtc ccgaaacctg     120
ctgaagacca cagatgacat ggtgaagacg gccagagaaa aactgaaaca ttattcctgc    180
actgctgaag acatcgatca tgaagacatc acacgggacc aaaccagcac attgaagacc    240
tgtttaccac tggaactaca caagaacgag agttgcctgg ctactagaga gacttcttcc    300
acaacaagag ggagctgcct gcccccacag aagacgtctt tgatgatgac cctgtgcctt    360
ggtagcatct atgaggactt gaagatgtac cagacagagt tccaggccat caacgcagca   420
cttcagaatc acaaccatca gcagatcatt ctagacaagg gcatgctggt ggccatcgat    480
gagctgatgc agtctctgaa tcataatggc gagactctgc gccagaaacc tcctgtggga    540
gaagcagacc cttacagagt gaaaatgaag ctctgcatcc tgcttcacgc cttcagcacc    600
cgcgtcgtga ccatcaacag ggtgatgggc tatctgagct ccgcctga               648

<210> SEQ ID NO 2
<211> LENGTH: 1008
<212> TYPE: DNA
```

<213> ORGANISM: Mus sp.
<220> FEATURE:
<223> OTHER INFORMATION: IL-12 p40

<400> SEQUENCE: 2

```
atgtgtcctc agaagctaac catctcctgg tttgccatcg ttttgctggt gtctccactc     60
atggccatgt gggagctgga aaagacgtt tatgttgtag aggtggactg gactcccgat    120
gcccctggag aaacagtgaa cctcacctgt gacacgcctg aagaagatga catcacctgg    180
acctcagacc agagacatgg agtcataggc tctggaaaga ccctgaccat cactgtcaaa    240
gagtttctag atgctggcca gtacacctgc cacaaaggag cgagactct gagccactca    300
catctgctgc tccacaagaa ggaaaatgga atttggtcca ctgaaatttt aaaaaatttc    360
aaaaacaaga cttccctgaa gtgtgaagca ccaaattact ccggacggtt cacgtgctca    420
tggctggtgc aaagaaacat ggacttgaag ttcaacatca gagcagtag cagttcccct    480
gactctcggg cagtgacatg tggaatggcg tctctgtctg cagagaaggt cacactggac    540
caaagggact atgagaagta ttcagtgtcc tgccaggaga atgtcacctg cccaactgcc    600
gaggagaccc tgcccattga actggcgttg aagcacggc agcagaataa atatgagaac    660
tacagcacca gcttcttcat cagggacatc atcaaaccag accgcccaa gaacttgcag    720
atgaagcctt tgaagaactc acaggtggag gtcagctggg agtaccctga ctcctggagc    780
actccccatt cctacttctc cctcaagttc tttgttcgaa tccagcgcaa gaaagaaaag    840
atgaaggaga cagaggaggg gtgtaaccag aaaggtgcgt tcctcgtaga aagacatct    900
accgaagtcc aatgcaaagg cgggaatgtc tgcgtgcaag ctcaggatcg ctattacaat    960
tcctcatgca gcaagtgggc atgtgttccc tgcagggtcc gatcctag              1008
```

<210> SEQ ID NO 3
<211> LENGTH: 660
<212> TYPE: DNA
<213> ORGANISM: Homo sapiens
<220> FEATURE:
<223> OTHER INFORMATION: IL-12 p35

<400> SEQUENCE: 3

```
atgtgtccag cgcgcagcct cctccttgtg gctaccctgg tcctcctgga ccacctcagt     60
ttggccagaa cctccccgt ggccactcca gacccaggaa tgttcccatg ccttcaccac    120
tcccaaaacc tgctgagggc cgtcagcaac atgctccaga aggccagaca aactctagaa    180
ttttaccctt gcacttctga agagattgat catgaagata tcacaaaaga taaaccagc    240
acagtggagg cctgttacc attggaatta ccaagaatg agagttgcct aaattccaga    300
gagacctctt tcataactaa tgggagttgc ctggcctcca aaagacctc ttttatgatg    360
gccctgtgcc ttagtagtat ttatgaagac ttgaagatgt accaggtgga gttcaagacc    420
atgaatgcaa agcttctgat ggatcctaag aggcagatct ttctagatca aaacatgctg    480
gcagttattg atgagctgat gcaggccctg aatttcaaca gtgagactgt gccacaaaaa    540
tcctcccttg aagaaccgga ttttataaa actaaaatca agctctgcat acttcttcat    600
gctttcagaa ttcgggcagt gactattgac agagtgacga gctatctgaa tgcttcctaa    660
```

<210> SEQ ID NO 4
<211> LENGTH: 987
<212> TYPE: DNA
<213> ORGANISM: Homo sapiens
<220> FEATURE:
<223> OTHER INFORMATION: IL-12 p40

-continued

<400> SEQUENCE: 4

```
atgtgtcacc agcagttggt catctcttgg ttttccctgg tttttctggc atctcccctc     60
gtggccatat gggaactgaa gaaagatgtt tatgtcgtag aattggattg gtatccggat    120
gcccctggag aaatggtggt cctcacctgt gacacccctg aagaagatgg tatcacctgg    180
accttggacc agagcagtga ggtcttaggc tctggcaaaa ccctgaccat ccaagtcaaa    240
gagtttggag atgctggcca gtacacctgt cacaaaggag cgaggttcta agccattcg     300
ctcctgctgc ttcacaaaaa ggaagatgga atttggtcca ctgatatttt aaaggaccag    360
aaagaaccca aaataagac ctttctaaga tgcgaggcca gaattattc tggacgtttc     420
acctgctggt ggctgacgac aatcagtact gatttgacat tcagtgtcaa aagcagcaga    480
ggctcttctg acccccaagg ggtgacgtgc ggagctgcta cactctctgc agagagagtc    540
agagggaca acaaggagta tgagtactca gtggagtgcc aggaggacag tgcctgccca     600
gctgctgagg agagtctgcc cattgaggtc atggtggatg ccgttcacaa gctcaagtat    660
gaaaactaca ccagcagctt cttcatcagg gacatcatca aacctgaccc acccaagaac    720
ttgcagctga agccattaaa gaattctcgg caggtggagg tcagctggga gtaccctgac    780
acctggagta ctccacattc ctacttctcc ctgacattct gcgttcaggt ccagggcaag    840
agcaagagag aaaagaaaga tagagtcttc acgacaagac cctcagccac ggtcatctgc    900
cgcaaaaatg ccagcattag cgtgcgggcc caggaccgct actatagctc atcttggagc    960
gaatgggcat ctgtgccctg cagttag                                        987
```

```
<210> SEQ ID NO 5
<211> LENGTH: 215
<212> TYPE: PRT
<213> ORGANISM: Mus sp.
<220> FEATURE:
<223> OTHER INFORMATION: IL-12 p35
```

<400> SEQUENCE: 5

```
Met Cys Gln Ser Arg Tyr Leu Leu Phe Leu Ala Thr Leu Ala Leu Leu
1               5                   10                  15

Asn His Leu Ser Leu Ala Arg Val Ile Pro Val Ser Gly Pro Ala Arg
            20                  25                  30

Cys Leu Ser Gln Ser Arg Asn Leu Leu Lys Thr Thr Asp Asp Met Val
        35                  40                  45

Lys Thr Ala Arg Glu Lys Leu Lys His Tyr Ser Cys Thr Ala Glu Asp
    50                  55                  60

Ile Asp His Glu Asp Ile Thr Arg Asp Gln Thr Ser Thr Leu Lys Thr
65                  70                  75                  80

Cys Leu Pro Leu Glu Leu His Lys Asn Glu Ser Cys Leu Ala Thr Arg
                85                  90                  95

Glu Thr Ser Ser Thr Thr Arg Gly Ser Cys Leu Pro Pro Gln Lys Thr
            100                 105                 110

Ser Leu Met Met Thr Leu Cys Leu Gly Ser Ile Tyr Glu Asp Leu Lys
        115                 120                 125

Met Tyr Gln Thr Glu Phe Gln Ala Ile Asn Ala Ala Leu Gln Asn His
    130                 135                 140

Asn His Gln Gln Ile Ile Leu Asp Lys Gly Met Leu Val Ala Ile Asp
145                 150                 155                 160

Glu Leu Met Gln Ser Leu Asn His Asn Gly Glu Thr Leu Arg Gln Lys
                165                 170                 175
```

-continued

```
Pro Pro Val Gly Glu Ala Asp Pro Tyr Arg Val Lys Met Lys Leu Cys
            180                 185                 190

Ile Leu Leu His Ala Phe Ser Thr Arg Val Val Thr Ile Asn Arg Val
        195                 200                 205

Met Gly Tyr Leu Ser Ser Ala
    210                 215

<210> SEQ ID NO 6
<211> LENGTH: 335
<212> TYPE: PRT
<213> ORGANISM: Mus sp.
<220> FEATURE:
<223> OTHER INFORMATION: IL-12 p40

<400> SEQUENCE: 6

Met Cys Pro Gln Lys Leu Thr Ile Ser Trp Phe Ala Ile Val Leu Leu
1               5                   10                  15

Val Ser Pro Leu Met Ala Met Trp Glu Leu Glu Lys Asp Val Tyr Val
            20                  25                  30

Val Glu Val Asp Trp Thr Pro Asp Ala Pro Gly Glu Thr Val Asn Leu
        35                  40                  45

Thr Cys Asp Thr Pro Glu Glu Asp Ile Thr Trp Thr Ser Asp Gln
    50                  55                  60

Arg His Gly Val Ile Gly Ser Gly Lys Thr Leu Thr Ile Thr Val Lys
65                  70                  75                  80

Glu Phe Leu Asp Ala Gly Gln Tyr Thr Cys His Lys Gly Gly Glu Thr
                85                  90                  95

Leu Ser His Ser His Leu Leu Leu His Lys Lys Glu Asn Gly Ile Trp
            100                 105                 110

Ser Thr Glu Ile Leu Lys Asn Phe Lys Asn Lys Thr Phe Leu Lys Cys
        115                 120                 125

Glu Ala Pro Asn Tyr Ser Gly Arg Phe Thr Cys Ser Trp Leu Val Gln
    130                 135                 140

Arg Asn Met Asp Leu Lys Phe Asn Ile Lys Ser Ser Ser Ser Ser Pro
145                 150                 155                 160

Asp Ser Arg Ala Val Thr Cys Gly Met Ala Ser Leu Ser Ala Glu Lys
                165                 170                 175

Val Thr Leu Asp Gln Arg Asp Tyr Glu Lys Tyr Ser Val Ser Cys Gln
            180                 185                 190

Glu Asp Val Thr Cys Pro Thr Ala Glu Glu Thr Leu Pro Ile Glu Leu
        195                 200                 205

Ala Leu Glu Ala Arg Gln Gln Asn Lys Tyr Glu Asn Tyr Ser Thr Ser
    210                 215                 220

Phe Phe Ile Arg Asp Ile Ile Lys Pro Asp Pro Lys Asn Leu Gln
225                 230                 235                 240

Met Lys Pro Leu Lys Asn Ser Gln Val Glu Val Ser Trp Glu Tyr Pro
                245                 250                 255

Asp Ser Trp Ser Thr Pro His Ser Tyr Phe Ser Leu Lys Phe Phe Val
            260                 265                 270

Arg Ile Gln Arg Lys Lys Glu Lys Met Lys Glu Thr Glu Glu Gly Cys
        275                 280                 285

Asn Gln Lys Gly Ala Phe Leu Val Glu Lys Thr Ser Thr Glu Val Gln
    290                 295                 300

Cys Lys Gly Gly Asn Val Cys Val Gln Ala Gln Asp Arg Tyr Tyr Asn
305                 310                 315                 320
```

```
Ser Ser Cys Ser Lys Trp Ala Cys Val Pro Cys Arg Val Arg Ser
            325                 330                 335

<210> SEQ ID NO 7
<211> LENGTH: 219
<212> TYPE: PRT
<213> ORGANISM: Homo sapiens
<220> FEATURE:
<223> OTHER INFORMATION: IL-12 p35

<400> SEQUENCE: 7

Met Cys Pro Ala Arg Ser Leu Leu Leu Val Ala Thr Leu Val Leu Leu
1               5                   10                  15

Asp His Leu Ser Leu Ala Arg Asn Leu Pro Val Ala Thr Pro Asp Pro
            20                  25                  30

Gly Met Phe Pro Cys Leu His His Ser Gln Asn Leu Leu Arg Ala Val
        35                  40                  45

Ser Asn Met Leu Gln Lys Ala Arg Gln Thr Leu Glu Phe Tyr Pro Cys
50                  55                  60

Thr Ser Glu Glu Ile Asp His Glu Asp Ile Thr Lys Asp Lys Thr Ser
65                  70                  75                  80

Thr Val Glu Ala Cys Leu Pro Leu Glu Leu Thr Lys Asn Glu Ser Cys
                85                  90                  95

Leu Asn Ser Arg Glu Thr Ser Phe Ile Thr Asn Gly Ser Cys Leu Ala
            100                 105                 110

Ser Arg Lys Thr Ser Phe Met Met Ala Leu Cys Leu Ser Ser Ile Tyr
        115                 120                 125

Glu Asp Leu Lys Met Tyr Gln Val Glu Phe Lys Thr Met Asn Ala Lys
130                 135                 140

Leu Leu Met Asp Pro Lys Arg Gln Ile Phe Leu Asp Gln Asn Met Leu
145                 150                 155                 160

Ala Val Ile Asp Glu Leu Met Gln Ala Leu Asn Phe Asn Ser Glu Thr
                165                 170                 175

Val Pro Gln Lys Ser Ser Leu Glu Glu Pro Asp Phe Tyr Lys Thr Lys
            180                 185                 190

Ile Lys Leu Cys Ile Leu Leu His Ala Phe Arg Ile Arg Ala Val Thr
        195                 200                 205

Ile Asp Arg Val Met Ser Tyr Leu Asn Ala Ser
210                 215

<210> SEQ ID NO 8
<211> LENGTH: 328
<212> TYPE: PRT
<213> ORGANISM: Homo sapiens
<220> FEATURE:
<223> OTHER INFORMATION: IL-12 p40

<400> SEQUENCE: 8

Met Cys His Gln Gln Leu Val Ile Ser Trp Phe Ser Leu Val Phe Leu
1               5                   10                  15

Ala Ser Pro Leu Val Ala Ile Trp Glu Leu Lys Lys Asp Val Tyr Val
            20                  25                  30

Val Glu Leu Asp Trp Tyr Pro Asp Ala Pro Gly Glu Met Val Val Leu
        35                  40                  45

Thr Cys Asp Thr Pro Glu Glu Asp Gly Ile Thr Trp Thr Leu Asp Gln
50                  55                  60

Ser Ser Glu Val Leu Gly Ser Gly Lys Thr Leu Thr Ile Gln Val Lys
```

```
                65                  70                  75                  80

Glu Phe Gly Asp Ala Gly Gln Tyr Thr Cys His Lys Gly Gly Glu Val
                85                  90                  95

Leu Ser His Ser Leu Leu Leu His Lys Lys Glu Asp Gly Ile Trp
            100                 105                 110

Ser Thr Asp Ile Leu Lys Asp Gln Lys Glu Pro Lys Asn Lys Thr Phe
            115                 120                 125

Leu Arg Cys Glu Ala Lys Asn Tyr Ser Gly Arg Phe Thr Cys Trp Trp
        130                 135                 140

Leu Thr Thr Ile Ser Thr Asp Leu Thr Phe Ser Val Lys Ser Ser Arg
145                 150                 155                 160

Gly Ser Ser Asp Pro Gln Gly Val Thr Cys Gly Ala Ala Thr Leu Ser
                165                 170                 175

Ala Glu Arg Val Arg Gly Asp Asn Lys Glu Tyr Glu Tyr Ser Val Glu
            180                 185                 190

Cys Gln Glu Asp Ser Ala Cys Pro Ala Ala Glu Glu Ser Leu Pro Ile
            195                 200                 205

Glu Val Met Val Asp Ala Val His Lys Leu Lys Tyr Glu Asn Tyr Thr
        210                 215                 220

Ser Ser Phe Phe Ile Arg Asp Ile Ile Lys Pro Asp Pro Pro Lys Asn
225                 230                 235                 240

Leu Gln Leu Lys Pro Leu Lys Asn Ser Arg Gln Val Glu Val Ser Trp
                245                 250                 255

Glu Tyr Pro Asp Thr Trp Ser Thr Pro His Ser Tyr Phe Ser Leu Thr
            260                 265                 270

Phe Cys Val Gln Val Gln Gly Lys Ser Lys Arg Glu Lys Lys Asp Arg
        275                 280                 285

Val Phe Thr Asp Lys Thr Ser Ala Thr Val Ile Cys Arg Lys Asn Ala
        290                 295                 300

Ser Ile Ser Val Arg Ala Gln Asp Arg Tyr Tyr Ser Ser Ser Trp Ser
305                 310                 315                 320

Glu Trp Ala Ser Val Pro Cys Ser
                325

<210> SEQ ID NO 9
<211> LENGTH: 17
<212> TYPE: DNA
<213> ORGANISM: Artificial Sequence
<220> FEATURE:
<223> OTHER INFORMATION: Synthetic ecdysone receptor response element
<220> FEATURE:
<221> NAME/KEY: misc_feature
<222> LOCATION: (9)..(9)
<223> OTHER INFORMATION: n is a,c,t,g, or t

<400> SEQUENCE: 9
rrggttcant gacacyy                                                        17

<210> SEQ ID NO 10
<211> LENGTH: 13
<212> TYPE: DNA
<213> ORGANISM: Artificial Sequence
<220> FEATURE:
<223> OTHER INFORMATION: Synthetic ecdysone receptor response element
<220> FEATURE:
<221> NAME/KEY: misc_feature
<222> LOCATION: (7)..(7)
<223> OTHER INFORMATION: n is a, c, g, or t

<400> SEQUENCE: 10
```
aggtcanagg tca                                                           13

<210> SEQ ID NO 11
<211> LENGTH: 15
<212> TYPE: DNA
<213> ORGANISM: Artifical Sequence
<220> FEATURE:
<223> OTHER INFORMATION: Synthetic ecdysone receptor response element

<400> SEQUENCE: 11
gggttgaatg aattt                                                         15

<210> SEQ ID NO 12
<211> LENGTH: 18
<212> TYPE: DNA
<213> ORGANISM: Artificial
<220> FEATURE:
<223> OTHER INFORMATION: Synthetic I-SceI homing endonuclease
      restriction site

<400> SEQUENCE: 12
tagggataac agggtaat                                                      18

<210> SEQ ID NO 13
<211> LENGTH: 37323
<212> TYPE: DNA
<213> ORGANISM: Artificial Sequence
<220> FEATURE:
<223> OTHER INFORMATION: Synthetic Ad-RTS-hIL-12 (SP1-RheoIL-12)

<400> SEQUENCE: 13
catcatcaat aatatacctt attttggatt gaagccaata tgataatgag ggggtggagt         60

ttgtgacgtg gcgcggggcg tgggaacggg gcgggtgacg tagtagtgtg gcggaagtgt        120
gatgttgcaa gtgtggcgga acacatgtaa gcgacggatg tggcaaaagt gacgtttttg        180
gtgtgcgccg gtgtacacag gaagtgacaa ttttcgcgcg gttttaggcg gatgttgtag        240

taaatttggg cgtaaccgag taagatttgg ccatttcgc gggaaaactg aataagagga        300
agtgaaatct gaaтaaттттт gtgttactca tagcgcgtaa tattt gtcta gggagatccg        360 gtaccggcgc gcgcgccgtt tggccgcctc gagtctagag atccggtgag tattaggcgc        420
gcaccaggtg ccgcaataaa atatctttat ттттcaттaca tctgtgtgtt ggтттттттgт        480 gtgaatcgat agtactaaca tacgctctcc atcaaaacaa aacgaaacaa aacaaactag        540
caaaataggc tgtccccagt gcaagtgcag gtgccagaac atttctctat cgataatgca        600
ggtcggagta ctgtcctccg agcggagtac tgtcctccga gcggagtact gtcctccgag        660
cggagtactg tcctccgagc ggagtactgt cctccgagcg gagtactgtc ctccgagcgg        720
agactcttcg aaggaagagg ggcggggtcg atcgaccccg ccctcttcc ttcgaaggaa        780 gaggggcggg gtcgaagacc tagagggtat ataatgggtg ccttagctgg tgtgtgagct        840
catcttcctg tagatcacgc gtgccaccat gggtcaccag cagttggtca tctcttggtt        900

ttccctggtt ттттcтggcaт ctcccctcgt ggccatatgg gaactgaaga aagatgttta        960

tgtcgtagaa ttggattggt atccggatgc ccctggagaa atggtggtcc тcaccстgтga       1020 cacccctgaa gaagatggta tcacctggac cttggaccag agcagtgagg tcttaggctc       1080

tggcaaaacc ctgaccatcc aagtcaaaga gtttggagat gctggccagt acacctgtca       1140
caaaggaggc gagttctaa gccattcgct cctgctgctt cacaaaaagg aagatggaat       1200

ttggtccact gaтaтттттaa aggaccagaa agaacccaaa aataagacct tctaagatg       1260

```
cgaggccaag aattattctg gacgtttcac ctgctggtgg ctgacgacaa tcagtactga    1320
tttgacattc agtgtcaaaa gcagcagagg ctcttctgac ccccaagggg tgacgtgcgg    1380
agctgctaca ctctctgcag agagagtcag aggggacaac aaggagtatg agtactcagt    1440
ggagtgccag gaggacagtg cctgcccagc tgctgaggag agtctgccca ttgaggtcat    1500
ggtggatgcc gttcacaagc tcaagtatga aaactacacc agcagcttct tcatcaggga    1560
catcatcaaa cctgacccac ccaagaactt gcagctgaag ccattaaaga attctcggca    1620
ggtggaggtc agctgggagt accctgacac ctggagtact ccacattcct acttctccct    1680
gacattctgc gttcaggtcc agggcaagag caagagagaa aagaaagata gagtcttcac    1740
ggacaagacc tcagccacgg tcatctgccg caaaaatgcc agcattagcg tgcgggccca    1800
ggaccgctac tatagctcat cttggagcga atgggcatct gtgccctgca gttaggttgg    1860
gcgagctcga attcattgat cccccgggct gcaggaattc gatatcaagc tcgggatccg    1920
aattccgccc ccccccccc cccccccta acgttactgg ccgaagccgc ttggaataag    1980
gccggtgtgc gtttgtctat atgttatttt ccaccatatt gccgtctttt ggcaatgtga    2040
gggcccggaa acctggccct gtcttcttga cgagcattcc tagggtgtct tccctctcg    2100
ccaaaggaat gcaaggtctg ttgaatgtcg tgaaggaagc agttcctctg gaagcttctt    2160
gaagacaaac aacgtctgta gcgacccttt gcaggcagcg gaacccccca cctggcgaca    2220
ggtgcctctg cggccaaaag ccacgtgtat aagatacacc tgcaaaggcg gcacaacccc    2280
agtgccacgt tgtgagttgg atagttgtgg aaagagtcaa atggctctcc tcaagcgtat    2340
tcaacaaggg gctgaaggat gcccagaagg tacccccattg tatgggatct gatctggggc    2400
ctcggtgcac atgctttaca tgtgtttagt cgaggttaaa aaaacgtcta ggccccccga    2460
accacgggga cgtggttttc cttttgaaaaa cacgatgata atatggccac aaccatgggt    2520
ccagcgcgca gcctcctcct tgtggctacc ctggtcctcc tggaccacct cagtttggcc    2580
agaaacctcc ccgtggccac tccagaccca ggaatgttcc catgccttca ccactcccaa    2640
aacctgctga gggccgtcag caacatgctc cagaaggcca gacaaactct agaattttac    2700
ccttgcactt ctgaagagat tgatcatgaa gatatcacaa aagataaaac cagcacagtg    2760
gaggcctgtt taccattgga attaaccaag aatgagagtt gcctaaattc cagagagacc    2820
tctttcataa ctaatgggag ttgcctggcc tccagaaaga cctcttttat gatggccctg    2880
tgccttagta gtatttatga agacttgaag atgtaccagg tggagttcaa gaccatgaat    2940
gcaaagcttc tgatggatcc taagaggcag atctttctag atcaaaacat gctggcagtt    3000
attgatgagc tgatgcaggc cctgaatttc aacagtgaga ctgtgccaca aaaatcctcc    3060
cttgaagaac cggatttta taaaactaaa atcaagctct gcatacttct tcatgctttc    3120
agaattcggg cagtgactat tgatagagtg atgagctatc tgaatgcttc ctaacgtacg    3180
tcgacatcga gaacttgttt attgcagctt ataatggtta caaataaagc aatagcatca    3240
caaatttcac aaataaagca ttttttttcac tgcattctag ttgtggtttg tccaaactca    3300
tcaatgtatc ttatcatgtc tgggcgcgcc ggcctccgcg ccgggttttg gcgcctcccg    3360
cgggcgcccc cctcctcacg gcgagcgctg ccacgtcaga cgaagggcgc agcgagcgtc    3420
ctgatccttc cgcccggacg ctcaggacag cggcccgctg ctcataagac tcggccttag    3480
aaccccagta tcagcagaag gacatttag gacgggactt gggtgactct agggcactgg    3540
ttttctttcc agagagcgga acaggcgagg aaaagtagtc ccttctcggc gattctgcgg    3600
```

```
agggatctcc gtggggcggt gaacgccgat gattatataa ggacgcgccg ggtgtggcac   3660
agctagttcc gtcgcagccg ggatttgggt cgcggttctt gtttgtggat cgctgtgatc   3720
gtcacttggt gagtagcggg ctgctgggct gggtacgtgc gctcggggtt ggcgagtgtg   3780
ttttgtgaag ttttttaggc accttttgaa atgtaatcat ttgggtcaat atgtaatttt   3840
cagtgttaga ctagtaaatt gtccgctaaa ttctggccgt ttttggcttt tttgttagac   3900
gagctagcgc cgccaccatg ggccctaaaa agaagcgtaa agtcgccccc ccgaccgatg   3960
tcagcctggg ggacgagctc cacttagacg gcgaggacgt ggcgatggcg catgccgacg   4020
cgctagacga tttcgatctg gacatgttgg gggacgggga ttccccgggt ccgggattta   4080 cccccacga ctccgccccc tacggcgctc tggatatggc cgacttcgag tttgagcaga   4140
tgtttaccga tgcccttgga attgacgagt acggtgggga attcgagatg cctgtggaca   4200
ggatcctgga ggcagagctt gctgtggaac agaagagtga ccagggcgtt gagggtcctg   4260
ggggaaccgg gggtagcggc agcagcccaa atgaccctgt gactaacatc tgtcaggcag   4320
ctgacaaaca gctattcacg cttgttgagt gggcgaagag gatcccacac ttttcctcct   4380
tgcctctgga tgatcaggtc atattgctgc gggcaggctg gaatgaactc ctcattgcct   4440
ccttttcaca ccgatccatt gatgttcgag atggcatcct ccttgccaca ggtcttcacg   4500
tgcaccgcaa ctcagcccat tcagcaggag taggagccat ctttgatcgg gtgctgacag   4560
agctagtgtc caaaatgcgt gacatgagga tggacaagac agagcttggc tgcctgaggg   4620
caatcattct gtttaatcca gaggtgaggg gtttgaaatc cgcccaggaa gttgaacttc   4680
tacgtgaaaa agtatatgcc gctttggaag aatatactag aacaacacat cccgatgaac   4740
caggaagatt tgcaaaactt ttgcttcgtc tgccttcttt acgttccata ggccttaagt   4800
gtttggagca tttgtttttc tttcgcctta ttggagatgt tccaattgat acgttcctga   4860
tggagatgct tgaatcacct tctgattcat aatctagcct agccccccctc tccctccccc   4920 cccccctaacg ttactggccg aagccgcttg gaataaggcc ggtgtgcgtt tgtctatatg   4980 ttatttttcca ccatattgcc gtcttttggc aatgtgaggg cccggaaacc tggccctgtc   5040
ttcttgacga gcattcctag gggtctttcc cctctcgcca aggaatgca aggtctgttg   5100 aatgtcgtga aggaagcagt tcctctggaa gcttcttgaa gacaaacaac gtctgtagcg   5160
accctttgca ggcagcggaa ccccccacct ggcgacaggt gcctctgcgg ccaaaagcca   5220
cgtgtataag atacacctgc aaaggcggca caaccccagt gccacgttgt gagttggata   5280
gttgtggaaa gagtcaaatg gctctcctca agcgtattca acaagggct gaaggatgcc   5340 cagaaggtac cccattgtat gggatctgat ctggggcctc ggtgcacatg ctttacatgt   5400
gtttagtcga ggttaaaaaa cgtctaggcc ccccgaacca cggggacgtg gttttccttt   5460
gaaaaacacg atctctaggc gccaccatga agctactgtc ttctatcgaa caagcatgcg   5520
atatttgccg acttaaaaag ctcaagtgct ccaaagaaaa accgaagtgc gccaagtgtc   5580
tgaagaacaa ctgggagtgt cgctactctc ccaaaaccaa aggtctccg ctgactaggg   5640 cacatctgac agaagtggaa tcaaggctag aaagactgga acagctattt ctactgattt   5700
ttcctcgaga agaccttgac atgattttga aaatggattc tttacaggat ataaaagcat   5760
tgttaacagg attatttgta caagataatg tgaataaaga tgccgtcaca gatagattgg   5820
cttcagtgga gactgatatg cctctaacat tgagacagca tagaataagt gcgacatcat   5880
catcggaaga gagtagtaac aaaggtcaaa gacagttgac tgtatcgccg gaattcccgg   5940
ggatccggcc tgagtgcgta gtacccgaga ctcagtgcgc catgaagcgg aaagagaaga   6000
```

```
aagcacagaa ggagaaggac aaactgcctg tcagcacgac gacggtggac gaccacatgc  6060
cgcccattat gcagtgtgaa cctccacctc ctgaagcagc aaggattcac gaagtggtcc  6120
caaggtttct ctccgacaag ctgttggtga caaaccggca gaaaaacatc ccccagttga  6180
cagccaacca gcagttcctt atcgccaggc tcatctggta ccaggacggg tacgagcagc  6240
cttctgatga agatttgaag aggattacgc agacgtggca gcaagcggac gatgaaaacg  6300
aagagtcgga cactcccttc cgccagatca cagagatgac tatcctcacg gtccaactta  6360
tcgtggagtt cgcgaaggga ttgccagggt cgccaagat ctcgcagcct gatcaaatta  6420
cgctgcttaa ggcttgctca agtgaggtaa tgatgctccg agtcgcgcga cgatacgatg  6480
cggcctcaga cagtattctg ttcgcgaaca accaagcgta cactcgcgac aactaccgca  6540
aggctggcat ggccgaggtc atcgaggatc tactgcactt ctgccggtgc atgtactcta  6600
tggcgttgga caacatccat tacgcgctgc tcacggctgt cgtcatcttt tctgaccggc  6660
cagggttgga gcagccgcaa ctggtggaag agatccagcg gtactacctg aatacgctcc  6720
gcatctatat cctgaaccag ctgagcgggt cggcgcgttc gtccgtcata tacggcaaga  6780
tcctctcaat cctctctgag ctacgcacgc tcggcatgca aaactccaac atgtgcatct  6840
ccctcaagct caagaacaga aagctgccgc cttttcctcga ggagatctgg gatgtggcgg  6900
acatgtcgca cacccaaccg ccgcctatcc tcgagtcccc cacgaatctc taggcggcct  6960
ctagagcggc cgccaccgcg gggagatcca gacatgataa gatacattga tgagtttgga  7020
caaaccacaa ctagaatgca gtgaaaaaaa tgctttattt gtgaaatttg tgatgctatt  7080
gctttatttg taaccattat aagctgcaat aaacaagtta acaacaacaa ttgcattcat  7140
tttatgtttc aggttcaggg ggaggtgtgg gaggtttttt aaagcaagta aaacctctac  7200
aaatgtggta tggctgatta tgatccggct gcctcgcgcg tttcggtgat gacggtgaaa  7260
acctctgaca catgcagctc ccggagacgg tcacagcttg tctgtaagcg gatgccggga  7320
gcagacaagc ccgtcagggc gcgtcagcgg gtgttggcgg gtgtcggggc gcagccatga  7380
ggtcgactct agtccccgcg gtggcagatc tggaaggtgc tgaggtacga tgagacccgc  7440
accaggtgca gaccctgcga gtgtggcggt aaacatatta ggaaccagcc tgtgatgctg  7500
gatgtgaccg aggagctgag gcccgatcac ttggtgctgg cctgcacccg cgctgagttt  7560
ggctctagcg atgaagatac agattgaggt actgaaatgt gtgggcgtgg cttaagggtg  7620
ggaaagaata tataaggtgg gggtcttatg tagttttgta tctgttttgc agcagccgcc  7680
gccgccatga gcaccaactc gtttgatgga agcattgtga gctcatattt gacaacgcgc  7740
atgccccat gggccggggt gcgtcagaat gtgatgggct ccagcattga tggtcgcccc  7800
gtcctgcccg caaactctac taccttgacc tacgagaccg tgtctggaac gccgttggag  7860
actgcagcct ccgccgccgc ttcagccgct gcagccaccg cccgcgggat tgtgactgac  7920
tttgcttttcc tgagcccgct tgcaagcagt gcagcttccc gttcatccgc ccgcgatgac  7980
aagttgacgg ctcttttggc acaattggat tctttgaccc gggaacttaa tgtcgtttct  8040
cagcagctgt tggatctgcg ccagcaggtt tctgccctga aggcttcctc ccctcccaat  8100
gcggtttaaa acataaataa aaaaccagac tctgtttgga tttggatcaa gcaagtgtct  8160
tgctgtcttt atttaggggt tttgcgcgcg cggtaggccc gggaccagcg gtctcggtcg  8220
ttgagggtcc tgtgtatttt ttccaggacg tggtaaaggt gactctggat gttcagatac  8280
atgggcataa gcccgtctct ggggtggagg tagcaccact gcagagcttc atgctgcggg  8340
```

```
gtggtgttgt agatgatcca gtcgtagcag gagcgctggg cgtggtgcct aaaaatgtct    8400
ttcagtagca agctgattgc caggggcagg cccttggtgt aagtgtttac aaagcggtta    8460
agctgggatg ggtgcatacg tggggatatg agatgcatct tggactgtat ttttaggttg    8520
gctatgttcc cagccatatc cctccgggga ttcatgttgt gcagaaccac cagcacagtg    8580
tatccggtgc acttgggaaa tttgtcatgt agcttagaag gaaatgcgtg gaagaacttg    8640
gagacgccct tgtgacctcc aagatttttcc atgcattcgt ccataatgat ggcaatgggc    8700
ccacgggcgg cggcctgggc gaagatattt ctgggatcac taacgtcata gttgtgttcc    8760
aggatgagat cgtcataggc cattttaca aagcgcgggc ggagggtgcc agactgcggt    8820
ataatggttc catccggccc aggggcgtag ttaccctcac agatttgcat ttcccacgct    8880
ttgagttcag atgggggat catgtctacc tgcgggcga tgaagaaaac ggtttccggg    8940
gtaggggaga tcagctggga agaaagcagg ttcctgagca gctgcgactt accgcagccg    9000
gtgggcccgt aaatcacacc tattaccggc tgcaactggt agttaagaga gctgcagctg    9060
ccgtcatccc tgagcagggg ggccacttcg ttaagcatgt ccctgactcg catgttttcc    9120
ctgaccaaat ccgccagaag gcgctcgccg cccagcgata gcagttcttg caaggaagca    9180
aagttttca acggtttgag accgtccgcc gtaggcatgc ttttgagcgt ttgaccaagc    9240
agttccaggc ggtcccacag ctcggtcacc tgctctacgg catctcgatc cagcatatct    9300
cctcgtttcg cgggttgggg cggctttcgc tgtacggcag tagtcggtgc tcgtccagac    9360
gggccagggt catgtctttc cacgggcgca gggtcctcgt cagcgtagtc tgggtcacgg    9420
tgaaggggtg cgctccgggc tgcgcgctgg ccagggtgcg cttgaggctg gtcctgctgg    9480
tgctgaagcg ctgccggtct tcgccctgcg cgtcggccag gtagcatttg accatggtgt    9540
catagtccag cccctccgcg gcgtggccct tggcgcgcag cttgcccttg gaggaggcgc    9600
cgcacgaggg gcagtgcaga cttttgaggg cgtagagctt gggcgcgaga aataccgatt    9660
ccggggagta ggcatccgcg ccgcaggccc cgcagacggt ctcgcattcc acgagccagg    9720
tgagctctgg ccgttcgggg tcaaaaacca ggtttccccc atgcttttg atgcgtttct    9780
tacctctggt ttccatgagc cggtgtccac gctcggtgac gaaaaggctg tccgtgtccc    9840
cgtatacaga cttgagaggc ctgtcctcga gcggtgttcc gcggtcctcc tcgtatagaa    9900
actcggacca ctctgagaca aaggctcgcg tccaggccag cacgaaggag gctaagtggg    9960
aggggtagcg gtcgttgtcc actagggggt ccactcgctc cagggtgtga agacacatgt    10020
cgccctcttc ggcatcaagg aaggtgattg gtttgtaggt gtaggccacg tgaccgggtg    10080
ttcctgaagg ggggctataa aaggggtgg gggcgcgttc gtcctcactc tcttccgcat    10140
cgctgtctgc gagggccagc tgttgggtg agtactccct ctgaaaagcg ggcatgactt    10200
ctgcgctaag attgtcagtt tccaaaaacg aggaggattt gatattcacc tggcccgcgg    10260
tgatgccttt gagggtggcc gcatccatct ggtcagaaaa gacaatcttt tgttgtcaa    10320
gcttggtggc aaacgacccg tagagggcgt tggacagcaa cttggcgatg gagcgcaggg    10380
tttggttttt gtcgcgatcg gcgcgctcct tggccgcgat gtttagctgc acgtattcgc    10440
gcgcaacgca ccgccattcg ggaaagacgg tggtgcgctc gtcgggcacc aggtgcacgc    10500
gccaaccgcg gttgtgcagg gtgacaaggt caacgctggt ggctacctct ccgcgtaggc    10560
gctcgttggt ccagcagagg cggccgccct tgcgcgagca gaatggcggt agggggtcta    10620
gctgcgtctc gtccggggg tctgcgtcca cggtaaagac cccgggcagc aggcgcgcgt    10680
cgaagtagtc tatcttgcat ccttgcaagt ctagcgcctg ctgccatgcg cgggcggcaa    10740
```

```
gcgcgcgctc gtatgggttg agtgggggac cccatggcat ggggtgggtg agcgcggagg   10800
cgtacatgcc gcaaatgtcg taaacgtaga ggggctctct gagtattcca agatatgtag   10860
ggtagcatct tccaccgcgg atgctggcgc gcacgtaatc gtatagttcg tgcgagggag   10920
cgaggaggtc gggaccgagg ttgctacggg cgggctgctc tgctcggaag actatctgcc   10980
tgaagatggc atgtgagttg gatgatatgg ttggacgctg gaagacgttg aagctggcgt   11040
ctgtgagacc taccgcgtca cgcacgaagg aggcgtagga gtcgcgcagc ttgttgacca   11100
gctcggcggt gacctgcacg tctagggcgc agtagtccag ggtttccttg atgatgtcat   11160
acttatcctg tcccttttt ttccacagct cgcggttgag gacaaactct tcgcggtctt   11220
tccagtactc ttggatcgga aacccgtcgg cctccgaacg gtaagagcct agcatgtaga   11280
actggttgac ggcctggtag gcgcagcatc ccttttctac gggtagcgcg tatgcctgcg   11340
cggccttccg gagcgaggtg tgggtgagcg caaaggtgtc cctgaccatg actttgaggt   11400
actggtattt gaagtcagtg tcgtcgcatc cgccctgctc ccagagcaaa aagtccgtgc   11460
gcttttggga acgcggattt ggcagggcga aggtgacatc gttgaagagt atctttcccg   11520
cgcgaggcat aaagttgcgt gtgatgcgga agggtcccgg cacctcggaa cggttgttaa   11580
ttacctgggc ggcgagcacg atctcgtcaa agccgttgat gttgtggccc acaatgtaaa   11640
gttccaagaa gcgcgggatg cccttgatgg aaggcaattt tttaagttcc tcgtaggtga   11700
gctcttcagg ggagctgagc ccgtgctctg aaagggccca gtctgcaaga tgagggttgg   11760
aagcgacgaa tgagctccac aggtcacggg ccattagcat ttgcaggtgg tcgcgaaagg   11820
tcctaaactg gcgacctatg gccattttt ctggggtgat gcagtagaag gtaagcgggt   11880
cttgttccca gcggtcccat ccaaggttcg cggctaggtc tcgcgcggca gtcactagag   11940
gctcatctcc gccgaacttc atgaccagca tgaagggcac gagctgcttc ccaaaggccc   12000
ccatccaagt ataggtctct acatcgtagg tgacaaagag acgctcggtg cgaggatgcg   12060
agccgatcgg gaagaactgg atctcccgcc accaattgga ggagtggcta ttgatgtggt   12120
gaaagtagaa gtccctgcga cgggccgaac actcgtgctg gcttttgtaa aaacgtgcgc   12180
agtactggca gcggtgcacg ggctgtacat cctgcacgag gttgacctga cgaccgcgca   12240
caaggaagca gagtgggaat ttgagcccct cgcctggcgg gtttggctgg tggtcttcta   12300
cttcggctgc ttgtccttga ccgtctggct gctcgagggg agttacgtg gatcggacca   12360 ccacgccgcg cgagcccaaa gtccagatgt ccgcgcgcgg cggtcggagc ttgatgacaa   12420
catcgcgcag atgggagctg tccatggtct ggagctcccg cggcgtcagg tcaggcggga   12480
gctcctgcag gtttacctcg catagacggg tcagggcgcg ggctagatcc aggtgatacc   12540
taatttccag gggctggttg gtggcggcgt cgatggcttg caagaggccg catcccgcg   12600 gcgcgactac ggtaccgcgc ggcgggcggt gggccgcggg ggtgtccttg atgatgcat    12660 ctaaaagcgt tgacgcgggc gagccccgg aggtaggggg ggctccggac ccgccggag    12720 aggggggcagg ggcacgtcgg cgccgcgcgc gggcaggagc tggtgctgcg cgcgtaggtt   12780
gctggcgaac gcgacgacgc ggcggttgat ctcctgaatc tggcgcctct gcgtgaagac   12840
gacgggcccg gtgagcttga acctgaaaga gagttcgaca gaatcaattt cggtgtcgtt   12900
gacggcggcc tggcgcaaaa tctcctgcac gtctcctgag ttgtcttgat aggcgatctc   12960
ggccatgaac tgctcgatct cttcctcctg gagatctccg cgtccggctc gctccacggt   13020
ggcggcgagg tcgttggaaa tgcgggccat gagctgcgag aaggcgttga ggcctccctc   13080
```

```
gttccagacg cggctgtaga ccacgccccc ttcggcatcg cgggcgcgca tgaccacctg   13140
cgcgagattg agctccacgt gccgggcgaa gacggcgtag tttcgcaggc gctgaaagag   13200
gtagttgagg gtggtggcgg tgtgttctgc cacgaagaag tacataaccc agcgtcgcaa   13260
cgtggattcg ttgatatccc ccaaggcctc aaggcgctcc atggcctcgt agaagtccac   13320
ggcgaagttg aaaaactggg agttgcgcgc cgacacggtt aactcctcct ccagaagacg   13380
gatgagctcg gcgacagtgt cgcgcacctc gcgctcaaag gctacagggg cctcttcttc   13440
ttcttcaatc tcctcttcca taagggcctc cccttcttct tcttctggcg gcggtggggg   13500 agggggggaca cggcggcgac gacggcgcac cgggaggcgg tcgacaaagc gctcgatcat   13560
ctccccgcgg cgacggcgca tggtctcggt gacggcgcgg ccgttctcgc gggggcgcag   13620
ttggaagacg ccgcccgtca tgtcccggtt atgggttggc gggggggctgc catgcggcag   13680 ggatacggcg ctaacgatgc atctcaacaa ttgttgtgta ggtactccgc cgccgaggga   13740
cctgagcgag tccgcatcga ccggatcgga aaacctctcg agaaaggcgt ctaaccagtc   13800
acagtcgcaa ggtaggctga gcaccgtggc gggcggcagc gggcggcggt cggggttgtt   13860
tctggcggag gtgctgctga tgatgtaatt aaagtaggcg tcttgagac ggcggatggt   13920 cgacagaagc accatgtcct tgggtccggc ctgctgaatg cgcaggcggt cggccatgcc   13980
ccaggcttcg ttttgacatc ggcgcaggtc tttgtagtag tcttgcatga gcctttctac   14040
cggcacttct tcttctcctt cctcttgtcc tgcatctctt gcatctatcg ctgcggcggc   14100
ggcggagttt ggccgtaggt ggcgccctct tcctcccatg cgtgtgaccc cgaagcccct   14160
catcggctga agcagggcta ggtcggcgac aacgcgctcg gctaatatgg cctgctgcac   14220
ctgcgtgagg gtagactgga agtcatccat gtccacaaag cggtggtatg cgcccgtgtt   14280
gatggtgtaa gtgcagttgg ccataacgga ccagttaacg gtctggtgac ccggctgcga   14340
gagctcggtg tacctgagac gcgagtaagc cctcgagtca aatacgtagt cgttgcaagt   14400
ccgcaccagg tactggtatc ccaccaaaaa gtgcggcggc ggctggcggt agaggggcca   14460
gcgtagggtg gccggggctc cgggggcgag atcttccaac ataaggcgat gatatccgta   14520
gatgtacctg gacatccagg tgatgccggc ggcggtggtg gaggcgcgcg gaaagtcgcg   14580
gacgcggttc cagatgttgc gcagcggcaa aaagtgctcc atggtcggga cgctctggcc   14640
ggtcaggcgc gcgcaatcgt tgacgctcta gcgtgcaaaa ggagagcctg taagcgggca   14700
ctcttccgtg gtctggtgga taaattcgca agggtatcat ggcggacgac cggggttcga   14760
gccccgtatc cggccgtccg ccgtgatcca tgcggttacc gcccgcgtgt cgaacccagg   14820
tgtgcgacgt cagacaacgg gggagtgctc cttttggctt ccttccaggc gcggcggctg   14880
ctgcgctagc ttttttggcc actggccgcg cgcagcgtaa gcggttaggc tggaaagcga   14940
aagcattaag tggctcgctc cctgtagccg gagggttatt ttccaagggt tgagtcgcgg   15000 gaccccggt tcgagtctcg gaccggccgg actgcggcga acgggggttt gcctccccgt   15060
catgcaagac cccgcttgca aattcctccg gaaacaggga cgagcccctt ttttgctttt   15120
cccagatgca tccggtgctg cggcagatgc gcccccctcc tcagcagcgg caagagcaag   15180
agcagcggca gacatgcagg gcaccctccc ctcctcctac cgcgtcagga ggggcgacat   15240
ccgcggttga cgcggcagca gatggtgatt acgaaccccc gcggcgccgg gcccggcact   15300
acctggactt ggaggagggc gagggcctgg cgcggctagg agcgccctct cctgagcggc   15360
acccaagggt gcagctgaag cgtgatacgc gtgaggcgta cgtgccgcgg cagaacctgt   15420
ttcgcgaccg cgagggagag gagcccgagg agatgcggga tcgaaagttc cacgcagggc   15480
```

```
gcgagctgcg gcatggcctg aatcgcgagc ggttgctgcg cgaggaggac tttgagcccg   15540
acgcgcgaac cgggattagt cccgcgcgcg cacacgtggc ggccgccgac ctggtaaccg   15600
catacgagca gacggtgaac caggagatta actttcaaaa aagctttaac aaccacgtgc   15660
gtacgcttgt ggcgcgcgag gaggtggcta taggactgat gcatctgtgg gactttgtaa   15720
gcgcgctgga gcaaaaccca aatagcaagc cgctcatggc gcagctgttc cttatagtgc   15780
agcacagcag ggacaacgag gcattcaggg atgcgctgct aaacatagta gagcccgagg   15840
gccgctggct gctcgatttg ataaacatcc tgcagagcat agtggtgcag gagcgcagct   15900
tgagcctggc tgacaaggtg gccgccatca actattccat gcttagcctg ggcaagtttt   15960
acgcccgcaa gatataccat acccettacg ttcccataga caaggaggta agatcgagg    16020 ggttctacat gcgcatggcg ctgaaggtgc ttaccttgag cgacgacctg ggcgtttatc   16080
gcaacgagcg catccacaag gccgtgagcg tgagccggcg gcgcgagctc agcgaccgcg   16140
agctgatgca cagcctgcaa agggccctgg ctggcacggg cagcggcgat agagaggcc    16200 agtcctactt tgacgcgggc gctgacctgc gctgggcccc aagccgacgc gccctggagg   16260
cagctggggc cggacctggg ctggcggtgg cacccgcgcg cgctggcaac gtcggcggcg   16320
tggaggaata tgacgaggac gatgagtacg agccagagga cggcgagtac taagcggtga   16380
tgtttctgat cagatgatgc aagacgcaac ggacccggcg gtgcgggcgg cgctgcagag   16440
ccagccgtcc ggccttaact ccacggacga ctggcgccag gtcatggacc gcatcatgtc   16500
gctgactgcg cgcaatcctg acgcgttccg gcagcagccg caggccaacc ggctctccgc   16560
aattctggaa gcggtggtcc cggcgcgcgc aaaccccacg cacgagaagg tgctggcgat   16620
cgtaaacgcg ctggccgaaa acagggccat ccggcccgac gaggccggcc tggtctacga   16680
cgcgctgctt cagcgcgtgg ctcgttacaa cagcggcaac gtgcagacca acctggaccg   16740
gctggtgggg gatgtgcgcg aggccgtggc gcagcgtgag cgcgcgcagc agcagggcaa   16800
cctgggctcc atggttgcac taaacgcctt cctgagtaca cagcccgcca acgtgccgcg   16860
gggacaggag gactacacca actttgtgag cgcactgcgg ctaatggtga ctgagacacc   16920
gcaaagtgag gtgtaccagt ctgggccaga ctattttttc cagaccagta gacaaggcct   16980
gcagaccgta aacctgagcc aggctttcaa aaacttgcag gggctgtggg gggtgcgggc   17040
tcccacaggc gaccgcgcga ccgtgtctag cttgctgacg cccaactcgc gcctgttgct   17100
gctgctaata gcgcccttca cggacagtgg cagcgtgtcc cgggacacat acctaggtca   17160
cttgctgaca ctgtaccgcg aggccatagg tcaggcgcat gtggacgagc atactttcca   17220
ggagattaca agtgtcagcc gcgcgctggg gcaggaggac acgggcagcc tggaggcaac   17280
cctaaactac ctgctgacca accggcggca gaagatcccc tcgttgcaca gtttaaacag   17340
cgaggaggag cgcattttgc gctacgtgca gcagagcgtg agccttaacc tgatgcgcga   17400
cggggtaacg cccagcgtgg cgctggacat gaccgcgcgc aacatggaac gggcatgta    17460 tgcctcaaac cggccgttta tcaaccgcct aatggactac ttgcatcgcg cggccgccgt   17520 gaacccgag  tatttcacca atgccatctt gaacccgcac tggctaccgc ccctggttt    17580 ctacaccggg ggattcgagg tgcccgaggg taacgatgga ttcctctggg acgacataga   17640
cgacagcgtg ttttccccgc aaccgcagac cctgctagag ttgcaacagc gcgagcaggc   17700
agaggcggcc ctgcgaaagg aaagcttccg caggccaagc agcttgtccg atctaggcgc   17760
tgcggccccg cggtcagatg ctagtagccc atttccaagc ttgataggt  ctcttaccag   17820
```

```
cactcgcacc acccgcccgc gcctgctggg cgaggaggag tacctaaaca actcgctgct   17880
gcagccgcag cgcgaaaaaa acctgcctcc ggcatttccc aacaacggga tagagagcct   17940
agtggacaag atgagtagat ggaagacgta cgcgcaggag cacagggacg tgccaggccc   18000
gcgcccgccc acccgtcgtc aaaggcacga ccgtcagcgg ggtctggtgt gggaggacga   18060
tgactcggca gacgacagca gcgtcctgga tttggggagg agtggcaacc cgtttgcgca   18120
ccttcgcccc aggctgggga gaatgtttta aaaaaaaaa aagcatgatg caaaataaaa    18180
aactcaccaa ggccatggca ccgagcgttg gtttcttgt attcccctta gtatgcggcg    18240
cgcggcgatg tatgaggaag gtcctcctcc ctcctacgag agtgtggtga gcgcggcgcc   18300
agtggcggcg gcgctgggtt ctcccttcga tgctcccctg acccgccgt ttgtgcctcc    18360
gcggtacctg cggcctaccg gggggagaaa cagcatccgt tactctgagt tggcacccct   18420
attcgacacc acccgtgtgt acctggtgga caacaagtca acggatgtgg catccctgaa   18480
ctaccagaac gaccacagca actttctgac cacggtcatt caaaacaatg actacagccc   18540
gggggaggca agcacacaga ccatcaatct tgacgaccgg tcgcactggg gcggcgacct   18600
gaaaaccatc ctgcatacca acatgccaaa tgtgaacgag ttcatgttta ccaataagtt   18660
taaggcgcgg gtgatggtgt cgcgcttgcc tactaaggac aatcaggtgg agctgaaata   18720
cgagtgggtg gagttcacgc tgcccgaggg caactactcc gagaccatga ccatagacct   18780
tatgaacaac gcgatcgtgg agcactactt gaaagtgggc agacagaacg gggttctgga   18840
aagcgacatc ggggtaaagt ttgacacccg caacttcaga ctggggtttg accccgtcac   18900
tggtcttgtc atgcctgggg tatatacaaa cgaagccttc catccagaca tcattttgct   18960
gccaggatgc ggggtggact tcacccacag ccgcctgagc aacttgttgg gcatccgcaa   19020
gcggcaaccc ttccaggagg gctttaggat cacctacgat gatctggagg gtggtaacat   19080
tcccgcactg ttggatgtgg acgcctacca ggcgagcttg aaagatgaca ccgaacaggg   19140
cgggggtggc gcaggcggca gcaacagcag tggcagcggc gcggaagaga actccaacgc   19200
ggcagccgcg gcaatgcagc cggtggagga catgaacgat catgccattc gcggcgacac   19260
ctttgccaca cgggctgagg agaagcgcgc tgaggccgaa gcagcggccg aagctgccgc   19320
ccccgctgcg caacccgagg tcgagaagcc tcagaagaaa ccggtgatca aaccccctgac  19380
agaggacagc aagaaacgca gttacaacct aataagcaat gacagcacct tcacccagta   19440
ccgcagctgg taccttgcat acaactacgg cgaccctcag accggaatcc gctcatggac   19500
cctgctttgc actcctgacg taacctgcgg ctcggagcag gtctactggt cgttgccaga   19560
catgatgcaa gaccccgtga ccttccgctc cacgcgccag atcagcaact ttccggtggt   19620
gggcgccgag ctgttgcccg tgcactccaa gagcttctac aacgaccagg ccgtctactc   19680
ccaactcatc cgccagtttta cctctctgac ccacgtgttc aatcgctttc ccgagaacca   19740
gattttggcg cgcccgccag cccccaccat caccaccgtc agtgaaaacg ttcctgctct   19800
cacagatcac gggacgctac cgctgcgcaa cagcatcgga ggagtccagc gagtgaccat   19860
tactgacgcc agacgccgca cctgccccta cgtttacaag gccctgggca tagtctcgcc   19920
gcgcgtccta tcgagccgca cttttttgagc aagcatgtcc atccttatat cgcccagcaa   19980
taacacaggc tggggcctgc gcttcccaag caagatgttt ggcggggcca agaagcgctc   20040
cgaccaacac ccagtgcgcg tgcgcgggca ctaccgcgcg ccctgggggcg cgcacaaacg   20100
cggccgcact gggcgcacca ccgtcgatga cgccatcgac gcggtggtgg aggaggcgcg   20160
caactacacg cccacgccgc accagtgtc cacagtggac gcggccattc agaccgtggt   20220
```

```
gcgcggagcc cggcgctatg ctaaaatgaa gagacggcgg aggcgcgtag cacgtcgcca   20280
ccgccgccga cccggcactg ccgcccaacg cgcggcggcg gccctgctta accgcgcacg   20340
tcgcaccggc cgacgggcgg ccatgcgggc cgctcgaagg ctggccgcgg gtattgtcac   20400
tgtgcccccc aggtccaggc gacgagcggc cgccgcagca gccgcggcca ttagtgctat   20460
gactcagggt cgcaggggca acgtgtattg ggtgcgcgac tcggttagcg gcctgcgcgt   20520
gcccgtgcgc acccgccccc cgcgcaacta gattgcaaga aaaaactact tagactcgta   20580
ctgttgtatg tatccagcgg cggcggcgcg caacgaagct atgtccaagc gcaaaatcaa   20640
agaagagatg ctccaggtca tcgcgccgga gatctatggc cccccgaaga aggaagagca   20700
ggattacaag ccccgaaagc taaagcgggt caaaagaaa aagaagatg atgatgatga   20760
acttgacgac gaggtggaac tgctgcacgc taccgcgccc aggcgacggg tacagtggaa   20820
aggtcgacgc gtaaaacgtg ttttgcgacc cggcaccacc gtagtcttta cgcccggtga   20880
gcgctccacc cgcacctaca agcgcgtgta tgatgaggtg tacggcgacg aggacctgct   20940
tgagcaggcc aacgagcgcc tcggggagtt tgcctacgga aagcggcata aggacatgct   21000
ggcgttgccg ctggacgagg gcaacccaac acctagccta aagcccgtaa cactgcagca   21060
ggtgctgccc gcgcttgcac cgtccgaaga aaagcgcggc ctaaagcgcg agtctggtga   21120
cttggcaccc accgtgcagc tgatggtacc caagcgccag cgactggaag atgtcttgga   21180
aaaaatgacc gtggaacctg gcctggagcc cgaggtccgc gtgcggccaa tcaagcaggt   21240
ggcgccggga ctgggcgtgc agaccgtgga cgttcagata cccactacca gtagcaccag   21300
tattgccacc gccacagagg gcatggagac acaaacgtcc ccggttgcct cagcggtggc   21360
ggatgccgcg gtgcaggcgg tcgctgcggc cgcgtccaag acctctacgg aggtgcaaac   21420
ggacccgtgg atgtttcgcg tttcagcccc ccggcgcccg cgccgttcga ggaagtacgg   21480
cgccgccagc gcgctactgc ccgaatatgc cctacatcct tccattgcgc ctaccccgg   21540
ctatcgtggc tacacctacc gccccagaag acgagcaact acccgacgcc gaaccaccac   21600
tggaacccgc cgccgccgtc gccgtcgcca gccgtgctg gccccgattt ccgtgcgcag   21660
ggtggctcgc gaaggaggca ggaccctggt gctgccaaca gcgcgctacc accccagcat   21720
cgtttaaaag ccggtctttg tggttcttgc agatatggcc ctcacctgcc gcctccgttt   21780
cccgtgccg ggattccgag gaagaatgca ccgtaggagg gcatggccg ccacggcct   21840
gacgggcggc atgcgtcgtg cgcaccaccg gcggcggcgc gcgtcgcacc gtcgcatgcg   21900
cggcggtatc ctgcccctcc ttattccact gatcgccgcg gcgattggcg ccgtgcccgg   21960
aattgcatcc gtggccttgc aggcgcagag acactgatta aaaacaagtt gcatgtggaa   22020
aaatcaaaat aaaagtctg gactctcacg ctcgcttggt cctgtaacta ttttgtagaa   22080
tggaagacat caactttgcg tctctggccc cgcgacacgg ctcgcgcccg ttcatgggaa   22140
actggcaaga tatcggcacc agcaatatga gcggtgcgc cttcagctgg ggctcgctgt   22200
ggagcggcat taaaaatttc ggttccaccg ttaagaacta tggcagcaag gcctggaaca   22260
gcagcacagg ccagatgctg agggataagt tgaaagagca aaatttccaa caaaaggtgg   22320
tagatggcct ggcctctggc attagcgggg tggtggacct ggccaaccag gcagtgcaaa   22380
ataagattaa cagtaagctt gatccccgcc ctcccgtaga ggagcctcca ccggccgtgg   22440
agacagtgtc tccagagggg cgtggcgaaa agcgtccgcg ccccgacagg aagaaactc   22500
tggtgacgca aatagacgag cctccctcgt acgaggaggc actaaagcaa ggcctgccca   22560
```

```
ccacccgtcc catcgcgccc atggctaccg gagtgctggg ccagcacaca cccgtaacgc    22620
tggacctgcc tcccccgcc gacacccagc agaaacctgt gctgccaggc ccgaccgccg     22680
ttgttgtaac ccgtcctagc cgcgcgtccc tgcgccgcgc cgccagcggt ccgcgatcgt    22740
tgcggcccgt agccagtggc aactggcaaa gcacactgaa cagcatcgtg ggtctggggg    22800
tgcaatccct gaagcgccga cgatgcttct gatagctaac gtgtcgtatg tgtgtcatgt    22860
atgcgtccat gtcgccgcca gaggagctgc tgagccgccg cgcgcccgct ttccaagatg    22920 gctaccccctt cgatgatgcc gcagtggtct tacatgcaca tctcgggcca ggacgcctcg   22980
gagtacctga gccccgggct ggtgcagttt gcccgcgcca ccgagacgta cttcagcctg    23040
aataacaagt ttagaaaccc cacggtggcg cctacgcacg acgtgaccac agaccggtcc    23100
cagcgtttga cgctgcggtt catccctgtg gaccgtgagg atactgcgta ctcgtacaag    23160
gcgcggttca ccctagctgt gggtgataac cgtgtgctgg acatggcttc cacgtacttt    23220
gacatccgcg gcgtgctgga caggggcccct acttttaagc cctactctgg cactgcctac   23280
aacgccctgg ctcccaaggg tgccccaaat ccttgcgaat gggatgaagc tgctactgct    23340
cttgaaataa acctagaaga agaggacgat gacaacgaag acgaagtaga cgagcaagct    23400
gagcagcaaa aaactcacgt atttgggcag gcgccttatt ctggtataaa tattacaaag    23460
gagggtattc aaataggtgt cgaaggtcaa cacctaaat atgccgataa acatttcaa     23520 cctgaacctc aaataggaga atctcagtgg tacgaaacag aaattaatca tgcagctggg    23580
agagtcctaa aaaagactac cccaatgaaa ccatgttacg gttcatatgc aaaacccaca    23640
aatgaaaatg gagggcaagg cattcttgta aagcaacaaa atgaaaagct agaaagtcaa    23700
gtggaaatgc aattttctc aactactgag gcagccgcag gcaatggtga taacttgact     23760
cctaaagtgg tattgtacag tgaagatgta gatatagaaa ccccagacac tcatatttct    23820
tacatgccca ctattaagga aggtaactca cgagaactaa tgggccaaca atctatgccc    23880
aacaggccta attacattgc ttttagggac aatttattg gtctaatgta ttacaacagc     23940
acgggtaata tgggtgttct ggcgggccaa gcatcgcagt tgaatgctgt tgtagatttg    24000
caagacagaa acacagagct ttcataccag cttttgcttg attccattgg tgatagaacc    24060
aggtactttt ctatgtggaa tcaggctgtt gacagctatg atccagatgt tagaattatt    24120
gaaaatcatg gaactgaaga tgaacttcca aattactgct ttccactggg aggtgtgatt    24180
aatacagaga ctcttaccaa ggtaaaacct aaaacaggtc aggaaaatgg atgggaaaaa    24240
gatgctacag aatttttcaga taaaaatgaa ataagagttg gaaataattt tgccatggaa    24300
atcaatctaa atgccaacct gtggagaaat ttcctgtact ccaacatagc gctgtatttg   24360
cccgacaagc taaagtacag tccttccaac gtaaaaattt ctgataaccc aaacacctac    24420
gactacatga acaagcgagt ggtggctccc gggctagtgg actgctacat taaccttgga    24480
gcacgctggt cccttgacta tatgacaac gtcaacccat taaccacca ccgcaatgct      24540 ggcctgcgct accgctcaat gttgctgggc aatggtcgct atgtgccctt ccacatccag    24600
gtgcctcaga agttctttgc cattaaaaac ctccttctcc tgccgggctc atacacctac    24660
gagtggaact tcaggaagga tgttaacatg gttctgcaga gctccctagg aaatgaccta    24720
agggttgacg gagccagcat taagtttgat agcatttgcc tttacgccac cttcttcccc    24780
atggcccaca caccgcctc cacgcttgag gccatgctta aaacgacac caacgaccag     24840 tcctttaacg actatctctc cgccgccaac atgctctacc ctataccgcc caacgctacc    24900
aacgtgccca tatccatccc ctcccgcaac tgggcggctt tccgcggctg ggccttcacg    24960
```

```
cgccttaaga ctaaggaaac cccatcactg ggctcgggct acgacccctta ttacacctac    25020 tctggctcta taccctacct agatggaacc ttttacctca accacacctt taagaaggtg    25080
gccattacct ttgactcttc tgtcagctgg cctggcaatg accgcctgct tacccccaac    25140
gagtttgaaa ttaagcgctc agttgacggg gagggttaca acgttgccca gtgtaacatg    25200
accaaagact ggttcctggt acaaatgcta gctaactata acattggcta ccagggcttc    25260
tatatcccag agagctacaa ggaccgcatg tactccttct ttagaaactt ccagcccatg    25320
agccgtcagg tggtggatga tactaaatac aaggactacc aacaggtggg catcctacac    25380
caacacaaca actctggatt tgttggctac cttgccccca ccatgcgcga aggacaggcc    25440
taccctgcta acttcccta tccgcttata ggcaagaccg cagttgacag cattacccag    25500
aaaaagtttc tttgcgatcg cacccttggg cgcatcccat tctccagtaa ctttatgtcc    25560
atgggcgcac tcacagacct gggccaaaac cttctctacg ccaactccgc ccacgcgcta    25620
gacatgactt tgaggtgga tcccatggac gagcccaccc ttctttatgt tttgtttgaa    25680
gtctttgacg tggtccgtgt gcaccagccg caccgcggcg tcatcgaaac cgtgtacctg    25740
cgcacgccct tctcggccgg caacgccaca acataaagaa gcaagcaaca tcaacaacag    25800
ctgccgccat gggctccagt gagcaggaac tgaaagccat tgtcaaagat cttggttgtg    25860
ggccatattt ttttgggcacc tatgacaagc gctttccagg ctttgtttct ccacacaagc    25920
tcgcctgcgc catagtcaat acggccggtc gcgagactgg gggcgtacac tggatggcct    25980
ttgcctggaa cccgcactca aaaacatgct acctctttga gccctttggc ttttctgacc    26040
agcgactcaa gcaggtttac cagtttgagt acgagtcact cctgcgccgt agcgccattg    26100
cttcttcccc cgaccgctgt ataacgctgg aaaagtccac ccaaagcgta caggggccca    26160
actcggccgc ctgtggacta ttctgctgca tgtttctcca cgccttttgcc aactggcccc    26220 aaactcccat ggatcacaac cccaccatga accttattac cggggtaccc aactccatgc    26280
tcaacagtcc ccaggtacag cccaccctgc gtcgcaacca ggaacagctc tacagcttcc    26340
tggagcgcca ctcgccctac ttccgcagcc acagtgcgca gattaggagc gccacttctt    26400
tttgtcactt gaaaaacatg taaaaataat gtactagaga cactttcaat aaaggcaaat    26460
gcttttattt gtacactctc gggtgattat ttaccccac ccttgccgtc tgcgccgttt    26520
aaaaatcaaa ggggttctgc cgcgcatcgc tatgcgccac tggcagggac acgttgcgat    26580
actggtgttt agtgctccac ttaaactcag gcacaaccat ccgcggcagc tcggtgaagt    26640
tttcactcca caggctgcgc accatcacca acgcgtttag caggtcgggc gccgatatct    26700
tgaagtcgca gttggggcct ccgccctgcg cgcgcgagtt gcgatacaca gggttgcagc    26760
actggaacac tatcagcgcc gggtggtgca cgctggccag cacgctcttg tcggagatca    26820
gatccgcgtc caggtcctcc gcgttgctca gggcgaacgg agtcaacttt ggtagctgcc    26880
ttcccaaaaa gggcgcgtgc ccaggctttg agttgcactc gcaccgtagt ggcatcaaaa    26940
ggtgaccgtg cccggtctgg gcgttaggat acagcgcctg cataaaagcc ttgatctgct    27000
taaaagccac ctgagccttt gcgccttcag agaagaacat gccgcaagac ttgccggaaa    27060
actgattggc cggacaggcc gcgtcgtgca cgcagcacct tgcgtcggtg ttggagatct    27120
gcaccacatt tcggccccac cggttcttca cgatcttggc cttgctagac tgctccttca    27180
gcgcgcgctg cccgttttcg ctcgtcacat ccatttcaat cacgtgctcc ttatttatca    27240
taatgcttcc gtgtagacac ttaagctcgc cttcgatctc agcgcagcgg tgcagccaca    27300
```

```
acgcgcagcc cgtgggctcg tgatgcttgt aggtcacctc tgcaaacgac tgcaggtacg   27360
cctgcaggaa tcgccccatc atcgtcacaa aggtcttgtt gctggtgaag gtcagctgca   27420
acccgcggtg ctcctcgttc agccaggtct tgcatacggc cgccagagct tccacttggt   27480
caggcagtag tttgaagttc gcctttagat cgttatccac gtggtacttg tccatcagcg   27540
cgcgcgcagc ctccatgccc ttctcccacg cagacacgat cggcacactc agcgggttca   27600
tcaccgtaat ttcactttcc gcttcgctgg gctcttcctc ttcctcttgc gtccgcatac   27660
cacgcgccac tgggtcgtct tcattcagcc gccgcactgt gcgcttacct cctttgccat   27720
gcttgattag caccggtggg ttgctgaaac ccaccatttg tagcgccaca tcttctcttt   27780
cttcctcgct gtccacgatt acctctggtg atggcgggcg ctcgggcttg ggagaagggc   27840
gcttcttttt cttcttgggc gcaatggcca aatccgccgc cgaggtcgat ggccgcgggc   27900
tgggtgtgcg cggcaccagc gcgtcttgtg atgagtcttc ctcgtcctcg gactcgatac   27960
gccgcctcat ccgcttttt gggggcgccc ggggaggcgg cggcgacggg gacggggacg   28020
acacgtcctc catggttggg ggacgtcgcg ccgcaccgcg tccgcgctcg ggggtggttt   28080
cgcgctgctc ctcttcccga ctggccattt ccttctccta taggcagaaa aagatcatgg   28140
agtcagtcga gaagaaggac agcctaaccg ccccctctga gttcgccacc accgcctcca   28200
ccgatgccgc caacgcgcct accaccttcc ccgtcgaggc accccgcctt gaggaggagg   28260
aagtgattat cgagcaggac ccaggttttg taagcgaaga cgacgaggac cgctcagtac   28320
caacagagga taaaaagcaa gaccaggaca acgcagaggc aaacgaggaa caagtcgggc   28380
ggggggacga aaggcatggc gactacctag atgtgggaga cgacgtgctg ttgaagcatc   28440
tgcagcgcca gtgcgccatt atctgcgacg cgttgcaaga gcgcagcgat gtgcccctcg   28500
ccatagcgga tgtcagcctt gcctacgaac gccacctatt ctcaccgcgc gtaccccca   28560
aacgccaaga aaacggcaca tgcgagccca acccgcgcct caacttctac cccgtatttg   28620
ccgtgccaga ggtgcttgcc acctatcaca tcttttttcca aaactgcaag ataccctat   28680
cctgccgtgc caaccgcagc cgagcggaca agcagctggc cttgcggcag ggcgctgtca   28740
tacctgatat cgcctcgctc aacgaagtgc caaaaatctt tgagggtctt ggacgcgacg   28800
agaagcgcgc ggcaaacgct ctgcaacagg aaaacagcga aaatgaaagt cactctggag   28860
tgttggtgga actcgagggt gacaacgcgc gcctagccgt actaaaacgc agcatcgagg   28920
tcacccactt tgcctacccg gcacttaacc tacccccaa ggtcatgagc acagtcatga   28980
gtgagctgat cgtgcgccgt gcgcagcccc tggagaggga tgcaaatttg caagaacaaa   29040
cagaggaggg cctacccgca gttggcgacg agcagctagc gcgctggctt caaacgcgcg   29100
agcctgccga cttggaggag cgacgcaaac taatgatggc cgcagtgctc gttaccgtgg   29160
agcttgagtg catgcagcgg ttctttgctg acccggagat gcagcgcaag ctagaggaaa   29220
cattgcacta caccttttcga cagggctacg tacgccaggc ctgcaagatc tccaacgtgg   29280
agctctgcaa cctggtctcc taccttggaa ttttgcacga aaaccgcctt gggcaaaacg   29340
tgcttcattc cacgctcaag ggcgaggcgc gccgcgacta cgtccgcgac tgcgtttact   29400
tatttctatg ctacacctgg cagacggcca tgggcgtttg gcagcagtgc ttggaggagt   29460
gcaacctcaa ggagctgcag aaactgctaa agcaaaactt gaaggaccta tggacggcct   29520
tcaacgagcg ctccgtggcc gcgcacctgg cggacatcat tttccccgaa cgcctgctta   29580
aaaccctgca acagggtctg ccagacttca ccagtcaaag catgttgcag aactttttagga   29640
actttatcct agagcgctca ggaatcttgc ccgccacctg ctgtgcactt cctagcgact   29700
```

```
ttgtgcccat taagtaccgc gaatgccctc cgccgctttg gggccactgc taccttctgc    29760
agctagccaa ctaccttgcc taccactctg acataatgga agacgtgagc ggtgacggtc    29820
tactggagtg tcactgtcgc tgcaacctat gcaccccgca ccgctccctg gtttgcaatt    29880
cgcagctgct taacgaaagt caaattatcg gtacctttga gctgcagggt ccctcgcctg    29940
acgaaaagtc cgcggctccg gggttgaaac tcactccggg gctgtggacg tcggcttacc    30000
ttcgcaaatt tgtacctgag gactaccacg cccacgagat taggttctac gaagaccaat    30060
cccgcccgcc taatgcggag cttaccgcct gcgtcattac ccagggccac attcttggcc    30120
aattgcaagc catcaacaaa gcccgccaag agtttctgct acgaaaggga cgggggttt     30180 acttggaccc ccagtccggc gaggagctca acccaatccc ccgccgccg cagccctatc     30240 agcagcagcc gcgggccctt gcttcccagg atggcaccca aaagaagct gcagctgccg     30300 ccgccaccca cggacgagga ggaatactgg gacagtcagg cagaggaggt tttggacgag    30360
gaggaggagg acatgatgga agactgggag agcctagacg aggaagcttc cgaggtcgaa    30420
gaggtgtcag acgaaacacc gtcaccctcg gtcgcattcc cctcgccggc gccccagaaa    30480
tcggcaaccg gttccagcat ggctacaacc tccgctcctc aggcgccgcc ggcactgccc    30540
gttcgccgac ccaaccgtag atgggacacc actggaacca gggccggtaa gtccaagcag    30600
ccgccgccgt tagcccaaga gcaacaacag cgccaaggct accgctcatg gcgcgggcac    30660
aagaacgcca tagttgcttg cttgcaagac tgtgggggca acatctcctt cgcccgccgc    30720
tttcttctct accatcacgg cgtggccttc ccccgtaaca tcctgcatta ctaccgtcat    30780
ctctacagcc catactgcac cggcggcagc ggcagcaaca gcagcggcca cacagaagca    30840
aaggcgaccg gatagcaaga ctctgacaaa gcccaagaaa tccacagcgg cggcagcagc    30900
aggaggagga gcgctgcgtc tggcgcccaa cgaacccgta tcgacccgcg agcttagaaa    30960
caggattttt cccactctgt atgctatatt tcaacagagc aggggccaag aacaagagct    31020
gaaaataaaa aacaggtctc tgcgatccct cacccgcagc tgcctgtatc acaaaagcga    31080
agatcagctt cggcgcacgc tggaagacgc ggaggctctc ttcagtaaat actgcgcgct    31140
gactcttaag gactagtttc gcgcccttc tcaaatttaa gcgcgaaaac tacgtcatct     31200
ccagcggcca caccccggcgc cagcaccctgt tgtcagcgcc attatgagca aggaaattcc    31260
cacgccctac atgtggagtt accagccaca aatgggactt gcggctggag ctgcccaaga    31320
ctactcaacc cgaataaact acatgagcgc gggaccccac atgatatccc gggtcaacgg    31380
aatacgcgcc caccgaaacc gaattctcct ggaacaggcg gctattacca ccacacctcg    31440
taataacctt aatccccgta gttggcccgc tgccctggtg taccaggaaa gtcccgctcc    31500
caccactgtg gtacttccca gagacgccca ggccgaagtt cagatgacta actcagggc     31560 gcagcttgcg ggcggctttc gtcacagggt gcggtcgccc gggcagggta taactcacct    31620
gacaatcaga gggcgaggta ttcagctcaa cgacgagtcg gtgagctcct cgcttggtct    31680
ccgtccggac gggacatttc agatcggcgg cgccggccgc tcttcattca cgcctcgtca    31740
ggcaatccta actctgcaga cctcgtcctc tgagccgcgc tctggaggca ttggaactct    31800
gcaatttatt gaggagtttg tgccatcggt ctactttaac cccttctcgg gacctccgg     31860 ccactatccg gatcaattta ttcctaactt tgacgcggta aaggactcgg cggacggcta    31920
cgactgaatg ttaagtggag aggcagagca actgcgcctg aaacacctgg tccactgtcg    31980
ccgccacaag tgctttgccc gcgactccgg tgagtttgc tactttgaat tgcccgagga     32040
```

```
tcatatcgag ggcccggcgc acggcgtccg gcttaccgcc cagggagagc ttgcccgtag    32100
cctgattcgg gagtttaccc agcgcccct gctagttgag cgggacaggg gaccctgtgt    32160
tctcactgtg atttgcaact gtcctaaccc tggattacat caagatctta ttcccttaa    32220 ctaataaaaa aaaataataa agcatcactt acttaaaatc agttagcaaa tttctgtcca    32280
gtttattcag cagcacctcc ttgccctcct cccagctctg gtattgcagc ttcctcctgg    32340
ctgcaaactt tctccacaat ctaaatggaa tgtcagtttc ctcctgttcc tgtccatccg    32400
cacccactat cttcatgttg ttgcagatga agcgcgcaag accgtctgaa gataccttca    32460
accccgtgta tccatatgac acggaaaccg gtcctccaac tgtgcctttt cttactcctc    32520
cctttgtatc ccccaatggg tttcaagaga gtcccctgg ggtactctct ttgcgcctat    32580
ccgaacctct agttacctcc aatggcatgc ttgcgctcaa atgggcaac ggcctctctc    32640 tggacgaggc cggcaacctt acctcccaaa atgtaaccac tgtgagccca cctctcaaaa    32700
aaaccaagtc aaacataaac ctggaaatat ctgcaccct cacagttacc tcagaagccc    32760
taactgtggc tgccgccgca cctctaatgg tcgcgggcaa cacactcacc atgcaatcac    32820 aggcccccgct aaccgtgcac gactccaaac ttagcattgc cacccaagga cccctcacag    32880
tgtcagaagg aaagctagcc ctgcaaacat caggcccct caccaccacc gatagcagta    32940
cccttactat cactgcctca cccccctctaa ctactgccac tggtagcttg ggcattgact    33000
tgaaagagcc catttataca caaaatggaa actaggact aaagtacggg gctcctttgc    33060
atgtaacaga cgacctaaac actttgaccg tagcaactgg tccaggtgtg actattaata    33120
atacttcctt gcaaactaaa gttactggag ccttgggttt tgattcacaa ggcaatatgc    33180
aacttaatgt agcaggagga ctaaggattg attctcaaaa cagacgcctt atacttgatg    33240
ttagttatcc gtttgatgct caaaaccaac taaatctaag actaggacag ggccctcttt    33300
ttataaactc agcccacaac ttggatatta actacaacaa aggcctttac ttgtttacag    33360
cttcaaacaa ttccaaaaag cttgaggtta acctaagcac tgccaagggg ttgatgtttg    33420
acgctacagc catagccatt aatgcaggag atgggcttga atttggttca cctaatgcac    33480
caaacacaaa tcccctcaaa acaaaaattg gccatggcct agaatttgat tcaaacaagg    33540
ctatggttcc taaactagga actggcctta gttttgacag cacaggtgcc attacagtag    33600
gaaacaaaaa taatgataag ctaactttgt ggaccacacc agctccatct cctaactgta    33660
gactaaatgc agagaaagat gctaaactca ctttggtctt aacaaaatgt ggcagtcaaa    33720
tacttgctac agtttcagtt ttggctgtta aaggcagttt ggctccaata tctggaacag    33780
ttcaaagtgc tcatcttatt ataagatttg acgaaaatgg agtgctacta acaattcct    33840 tcctggaccc agaatattgg aactttagaa atggagatct tactgaaggc acagcctata    33900
caaacgctgt tggatttatg cctaacctat cagcttatcc aaaatctcac ggtaaaactg    33960
ccaaaagtaa cattgtcagt caagtttact taaacggaga caaaactaaa cctgtaacac    34020
taaccattac actaaacggt acacaggaaa caggagacac aactccaagt gcatactcta    34080
tgtcattttc atgggactgg tctggccaca actacattaa tgaaatattt gccacatcct    34140
cttacacttt ttcatacatt gcccaagaat aaagaatcgt ttgtgttatg tttcaacgtg    34200 tttattttc aattgcagaa aatttcaagt catttttcat tcagtagtat agccccacca    34260
ccacatagct tatacagatc accgtacctt aatcaaactc acagaaccct agtattcaac    34320
ctgccacctc cctcccaaca cacagagtac acagtccttt ctccccggct ggccttaaaa    34380
agcatcatat catgggtaac agacatattc ttaggtgtta tattccacac ggtttcctgt    34440
```

```
cgagccaaac gctcatcagt gatattaata aactccccgg gcagctcact taagttcatg   34500
tcgctgtcca gctgctgagc cacaggctgc tgtccaactt gcggttgctt aacgggcggc   34560
gaaggagaag tccacgccta catgggggta gagtcataat cgtgcatcag gatagggcgg   34620
tggtgctgca gcagcgcgcg aataaactgc tgccgccgcc gctccgtcct gcaggaatac   34680
aacatggcag tggtctcctc agcgatgatt cgcaccgccc gcagcataag gcgccttgtc   34740
ctccgggcac agcagcgcac cctgatctca cttaaatcag cacagtaact gcagcacagc   34800
accacaatat tgttcaaaat cccacagtgc aaggcgctgt atccaaagct catggcgggg   34860
accacagaac ccacgtggcc atcataccac aagcgcaggt agattaagtg gcgacccctc   34920
ataaacacgc tggacataaa cattacctct tttggcatgt tgtaattcac cacctcccgg   34980
taccatataa acctctgatt aaacatggcg ccatccacca ccatcctaaa ccagctggcc   35040
aaaacctgcc cgccggctat acactgcagg gaaccgggac tggaacaatg acagtggaga   35100
gcccaggact cgtaaccatg gatcatcatg ctcgtcatga tatcaatgtt ggcacaacac   35160
aggcacacgt gcatacactt cctcaggatt acaagctcct cccgcgttag aaccatatcc   35220
cagggaacaa cccattcctg aatcagcgta aatcccacac tgcagggaag acctcgcacg   35280
taactcacgt tgtgcattgt caaagtgtta cattcgggca gcagcggatg atcctccagt   35340
atggtagcgc gggtttctgt ctcaaaagga ggtagacgat ccctactgta cggagtgcgc   35400
cgagacaacc gagatcgtgt tggtcgtagt gtcatgccaa atggaacgcc ggacgtagtc   35460
atatttcctg aagcaaaacc aggtgcgggc gtgacaaaca gatctgcgtc tccggtctcg   35520
ccgcttagat cgctctgtgt agtagttgta gtatatccac tctctcaaag catccaggcg   35580 cccctggct tcgggttcta tgtaaactcc ttcatgcgcc gctgccctga taacatccac   35640
caccgcagaa taagccacac ccagccaacc tacacattcg ttctgcgagt cacacacggg   35700
aggagcggga agagctggaa gaaccatgtt tttttttta ttccaaaaga ttatccaaaa   35760
cctcaaaatg aagatctatt aagtgaacgc gctcccctcc ggtggcgtgg tcaaactcta   35820
cagccaaaga acagataatg gcatttgtaa gatgttgcac aatggcttcc aaaaggcaaa   35880
cggccctcac gtccaagtgg acgtaaaggc taaaccccttc agggtgaatc tcctctataa   35940
acattccagc accttcaacc atgcccaaat aattctcatc tcgccacctt ctcaatatat   36000
ctctaagcaa atcccgaata ttaagtccgg ccattgtaaa aatctgctcc agagcgccct   36060
ccaccttcag cctcaagcag cgaatcatga ttgcaaaaat tcaggttcct cacagacctg   36120
tataagattc aaaagcggaa cattaacaaa aataccgcga tcccgtaggt cccttcgcag   36180
ggccagctga acataatcgt gcaggtctgc acggaccagc gcggccactt ccccgccagg   36240
aaccatgaca aaagaaccca cactgattat gacacgcata ctcggagcta tgctaaccag   36300
cgtagccccg atgtaagctt gttgcatggg cggcgatata aaatgcaagg tgctgctcaa   36360
aaaatcaggc aaagcctcgc gcaaaaaaga aagcacatcg tagtcatgct catgcagata   36420
aaggcaggta agctccggaa ccaccacaga aaaagacacc attttctct caaacatgtc   36480 tgcgggtttc tgcataaaca caaaataaaa taacaaaaaa acatttaaac attagaagcc   36540
tgtcttacaa caggaaaaac aacccttata agcataagac ggactacggc catgccggcg   36600
tgaccgtaaa aaaactggtc accgtgatta aaaagcacca ccgacagctc ctcggtcatg   36660
tccggagtca taatgtaaga ctcggtaaac acatcaggtt gattcacatc ggtcagtgct   36720
aaaaagcgac cgaaatagcc cgggggaata catacccgca ggcgtagaga caacattaca   36780
```

-continued

```
gcccccatag gaggtataac aaaattaata ggagagaaaa acacataaac acctgaaaaa  36840
ccctcctgcc taggcaaaat agcaccctcc cgctccagaa caacatacag cgcttccaca  36900
gcggcagcca taacagtcag ccttaccagt aaaaaagaaa acctattaaa aaaacaccac  36960
tcgacacggc accagctcaa tcagtcacag tgtaaaaaag ggccaagtgc agagcgagta  37020
tatataggac taaaaaatga cgtaacggtt aaagtccaca aaaaacaccc agaaaaccgc  37080
acgcgaacct acgcccagaa acgaaagcca aaaaacccac aacttcctca aatcgtcact  37140
tccgttttcc cacgttacgt cacttcccat tttaagaaaa ctacaattcc caacacatac  37200
aagttactcc gccctaaaac ctacgtcacc cgccccgttc ccacgccccg cgccacgtca  37260
caaactccac cccctcatta tcatattggc ttcaatccaa aataaggtat attattgatg  37320
atg                                                                37323
```